United States Patent
Mitsui et al.

(10) Patent No.: US 10,025,180 B2
(45) Date of Patent: Jul. 17, 2018

(54) SULFONIUM COMPOUND, RESIST COMPOSITION, AND PATTERNING PROCESS

(71) Applicant: Shin-Etsu Chemical Co., Ltd., Tokyo (JP)

(72) Inventors: Ryo Mitsui, Joetsu (JP); Takayuki Fujiwara, Joetsu (JP); Ryosuke Taniguchi, Joetsu (JP); Koji Hasegawa, Joetsu (JP); Masaki Ohashi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/690,846

(22) Filed: Aug. 30, 2017

(65) Prior Publication Data

US 2018/0059543 A1    Mar. 1, 2018

(30) Foreign Application Priority Data

Aug. 31, 2016 (JP) ................. 2016-169793

(51) Int. Cl.
| | | |
|---|---|---|
| G03F 7/004 | (2006.01) | |
| G03F 7/16 | (2006.01) | |
| G03F 7/20 | (2006.01) | |
| G03F 7/32 | (2006.01) | |
| C07C 309/20 | (2006.01) | |
| C07C 309/02 | (2006.01) | |
| C07C 381/12 | (2006.01) | |
| G03F 7/38 | (2006.01) | |

(52) U.S. Cl.
CPC .......... *G03F 7/0045* (2013.01); *C07C 309/02* (2013.01); *C07C 309/20* (2013.01); *C07C 381/12* (2013.01); *G03F 7/16* (2013.01); *G03F 7/2004* (2013.01); *G03F 7/2041* (2013.01); *G03F 7/2053* (2013.01); *G03F 7/322* (2013.01); *G03F 7/38* (2013.01)

(58) Field of Classification Search
CPC ........................ C07C 309/02; C07C 309/20
See application file for complete search history.

(56) References Cited

U.S. PATENT DOCUMENTS

| | | | | |
|---|---|---|---|---|
| 8,173,354 | B2 * | 5/2012 | Ohsawa | C07C 381/12 430/270.1 |
| 2014/0349221 | A1 * | 11/2014 | Takizawa | G03F 7/0045 430/9 |
| 2017/0205709 | A1 * | 7/2017 | Hatakeyama | G03F 7/0045 |

FOREIGN PATENT DOCUMENTS

| | | | |
|---|---|---|---|
| EP | 1710230 A1 | * | 4/2006 |
| EP | 1980911 A2 | * | 4/2008 |
| EP | 1939691 A2 | * | 7/2008 |
| EP | 2950143 A1 | * | 12/2015 |
| JP | 2007-145797 A | | 6/2007 |
| JP | 2008-281974 A | | 11/2008 |
| JP | 2008-281975 A | | 11/2008 |
| JP | 4554665 B2 | | 9/2010 |
| JP | 2013-167826 A | | 8/2013 |

OTHER PUBLICATIONS

Dammel et al., "193 nm Immersion Lithography—Taking the Plunge", Journal of Photopolymer Science and Technology, vol. 17, No. 4, pp. 587-602, (2004).

* cited by examiner

*Primary Examiner* — Cynthia Hamilton
(74) *Attorney, Agent, or Firm* — Westerman, Hattori, Daniels & Adrian, LLP

(57) ABSTRACT

A sulfonium salt containing an acid-eliminatable substituent group which is effective for improving contrast is highly soluble and uniformly dispersible. A resist composition comprising the sulfonium salt as photoacid generator forms a pattern with a high resolution, rectangularity, and reduced LWR.

19 Claims, 10 Drawing Sheets

SULFONIUM COMPOUND, RESIST COMPOSITION, AND PATTERNING PROCESS

CROSS-REFERENCE TO RELATED APPLICATION

This non-provisional application claims priority under 35 U.S.C. § 119(a) on Patent Application No. 2016-169793 filed in Japan on Aug. 31, 2016, the entire contents of which are hereby incorporated by reference.

TECHNICAL FIELD

This invention relates to a sulfonium compound, a resist composition comprising the same, and a pattern forming process using the resist composition.

BACKGROUND ART

While a number of recent efforts are being made to achieve a finer pattern rule in the drive for higher integration and operating speeds in LSI devices, DUV and EUV lithography processes are thought to hold particular promise as the next generation in microfabrication technology. In particular, photolithography using ArF excimer laser is requisite to the micropatterning technique capable of achieving a feature size of 0.13 μm or less.

The ArF lithography started partial use from the fabrication of 130-nm node devices and became the main lithography since 90-nm node devices. Although lithography using $F_2$ laser (157 nm) was initially thought promising as the next lithography for 45-nm node devices, its development was retarded by several problems. A highlight was suddenly placed on the ArF immersion lithography that introduces a liquid having a higher refractive index than air (e.g., water, ethylene glycol, glycerol) between the projection lens and the wafer, allowing the projection lens to be designed to a numerical aperture (NA) of 1.0 or higher and achieving a higher resolution. See Non-Patent Document 1. The ArF immersion lithography is now implemented on the commercial stage. The immersion lithography requires a resist composition which is substantially insoluble in water.

In the ArF (193 nm) lithography, a high sensitivity resist composition capable of achieving a high resolution at a small dose of exposure is needed to prevent the degradation of precise and expensive optical system materials. Among several measures for providing high sensitivity resist compositions, the most common is to select each component which is highly transparent at the wavelength of 193 nm. For example, polymers of acrylic acid and derivatives thereof, norbornene-maleic anhydride alternating copolymers, polynorbonene, ring-opening metathesis polymerization (ROMP) polymers, and hydrogenated ROMP polymers have been proposed as the base resin. This choice is effective to some extent in that the transparency of a resin alone is increased.

Recently a highlight is put on the negative tone resist adapted for organic solvent development as well as the positive tone resist adapted for aqueous alkaline development. It would be desirable if a very fine hole pattern, which is not achievable with the positive tone, is resolvable through negative tone exposure. To this end, a positive resist composition featuring a high resolution is subjected to organic solvent development to form a negative pattern. An attempt to double a resolution by combining two developments, aqueous alkaline development and organic solvent development is under study.

As the ArF resist composition for negative tone development with organic solvent, positive ArF resist compositions of the prior art design may be used. Such pattern forming processes are described in Patent Documents 1 to 3.

To meet the current rapid progress of microfabrication technology, development efforts are put on not only the process, but also the resist composition. Studies have also been made on photoacid generators (PAGs). Commonly used are sulfonium salts of triphenylsulfonium cation with perfluroalkanesulfonic acid anion. These salts generate perfluoroalkanesulfonic acids, especially perfluorooctanesulfonic acid (PFOS), which are considered problematic with respect to their non-degradability, biological concentration and toxicity. It is rather restricted to apply these salts to the resist composition. Instead, PAGs capable of generating perfluorobutanesulfonic acid are currently used, but are awkward to achieve a high resolution because of substantial diffusion of the generated acid in the resist composition. To address the problem, partially fluorinated alkane sulfonic acids and salts thereof are developed. For instance, Patent Document 1 refers to the prior art PAGs capable of generating α,α-difluoroalkanesulfonic acid, such as di(4-t-butylphenyl)iodonium 1,1-difluoro-2-(1-naphthyl)ethanesulfonate and PAGs capable of generating α,α,β,β-tetrafluoroalkanesulfonic acid. Despite a reduced degree of fluorine substitution, these PAGs still have the following problems. Since they do not have a decomposable substituent group such as ester structure, they are unsatisfactory from the aspect of environmental safety due to ease of decomposition. The molecular design to change the size of alkanesulfonic acid is limited. Fluorine-containing starting reactants are expensive.

Incorporating a bulky substituent or polar group into PAG is effective for suppressing acid diffusion. Patent Document 4 describes a PAG capable of generating 2-acyloxy-1,1,3,3,3-pentafluoropropane-1-sulfonic acid which is fully soluble and stable in organic solvents and allows for a wide span of molecular design. In particular, a PAG having incorporated therein a bulky substituent, 2-(1-adamantyloxy)-1,1,3,3,3-pentafluoropropane-1-sulfonic acid is characterized by slow acid diffusion. A resist composition comprising this PAG, however, is still insufficient in precise control of acid diffusion, and its lithography performance is unsatisfactory when evaluated totally in terms of LWR (as an index of pattern roughness) and resolution.

CITATION LIST

Patent Document 1: JP-A 2008-281974
Patent Document 2: JP-A 2008-281975
Patent Document 3: JP 4554665 (U.S. Pat. No. 8,227,183)
Patent Document 4: JP-A 2007-145797
Patent Document 5: JP-A 2013-167826 (U.S. Pat. No. 9,069,246)
Non-Patent Document 1: Journal of Photopolymer Science and Technology, Vol. 17, No. 4, p 587 (2004)

DISCLOSURE OF THE INVENTION

An object of the invention is to provide a sulfonium compound, a resist composition comprising the sulfonium compound as photoacid generator, and a patterning process using the resist composition, wherein the composition forms a pattern with improved resolution and reduced LWR when processed by DUV, EUV or EB lithography.

The inventors have found that a resist composition comprising a sulfonium compound of specific structure forms a resist film having improved resolution and reduced LWR and is effective for precise micropatterning.

In one aspect, the invention provides a sulfonium compound having the formula (1A), (1B) or (1C).

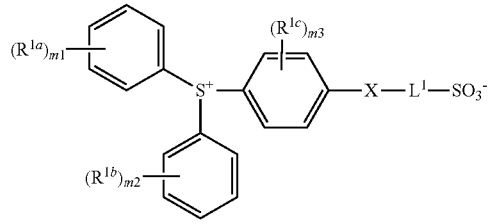
(1A)

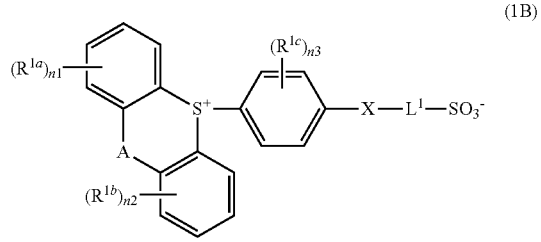
(1B)

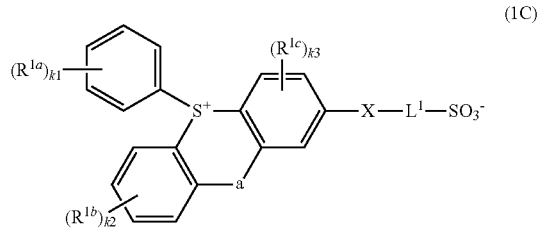
(1C)

Herein $L^1$ is a $C_1$-$C_{20}$ straight, branched or cyclic divalent hydrocarbon group which may contain a heteroatom-containing radical, X is a divalent linking group, A is a single bond, methylene group, carbonyl group, sulfinyl group, sulfonyl group, amino group, ether bond, thioether bond, ester bond, carbonate bond, carbamate bond or sulfonic acid ester bond, $R^{1a}$ to $R^{1c}$ are each independently a $C_1$-$C_{20}$ straight, branched or cyclic monovalent hydrocarbon group which may contain a heteroatom-containing radical, at least one of $R^{1a}$ to $R^{1c}$ being a group having the formula (2) shown below, with the proviso that where at least two groups $R^{1a}$ are included, two of them may bond together to from a ring with the carbon atoms on the benzene ring to which they are attached, where at least two groups $R^{1b}$ are included, two of them may bond together to from a ring with the carbon atoms on the benzene ring to which they are attached, and where at least two groups $R^{1c}$ are included, two of them may bond together to from a ring with the carbon atoms on the benzene ring to which they are attached, m1, m2 and m3 are integers meeting $0 \leq m1 \leq 5$, $0 \leq m2 \leq 5$, $0 \leq m3 \leq 4$, and $m1+m2+m3 \geq 1$, n1, n2 and n3 are integers meeting $0 \leq n1 \leq 4$, $0 \leq n2 \leq 4$, $0 \leq n3 \leq 4$, and $n1+n2+n3 \geq 1$, k1, k2 and k3 are integers meeting $0 \leq k1 \leq 5$, $0 \leq k2 \leq 4$, $0 \leq k3 \leq 3$, and $k1+k2+k3 \geq 1$.

(2)

Herein $L^2$ is a $C_1$-$C_{20}$ straight, branched or cyclic divalent hydrocarbon group which may contain a heteroatom-containing radical, $R^2$ is an acid-eliminatable group, $R^{f1}$ and $R^{f2}$ are each independently hydrogen, $C_1$-$C_{20}$ straight, branched or cyclic alkyl group, fluorine, or $C_1$-$C_{20}$ straight, branched or cyclic fluoroalkyl group, at least one of $R^{f1}$ and $R^{f2}$ being fluorine or fluoroalkyl, and the broken line designates a valence bond.

Preferably, $R^{f1}$ and $R^{f2}$ each are trifluoromethyl.

The preferred sulfonium compound has the formula (3A), (3B) or (3C).

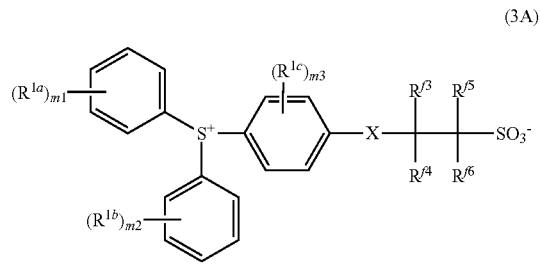
(3A)

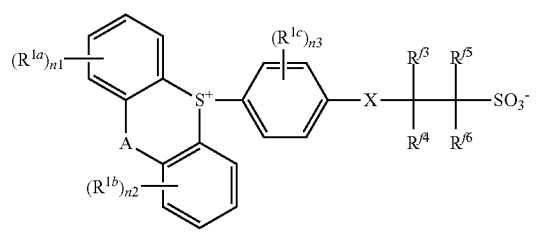
(3B)

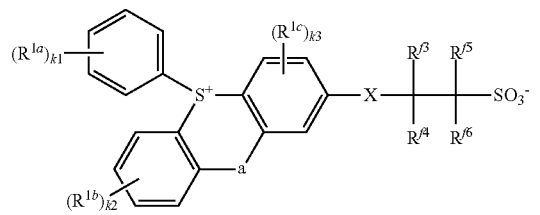
(3C)

Herein $R^{1a}$, $R^{1b}$, $R^{1c}$, X, A, m1, m2, m3, n1, n2, n3, k1, k2, and k3 are as defined above, $R^{f3}$, $R^{f4}$, $R^{f5}$ and $R^{f6}$ are each independently hydrogen, fluorine or trifluoromethyl. Preferably, $R^{f5}$ and $R^{f6}$ each are fluorine.

In a second aspect, the invention provides a photoacid generator comprising the sulfonium compound defined above.

In a third aspect, the invention provides a resist composition comprising the photoacid generator defined above.

The resist composition may further comprise a base resin containing a polymer comprising recurring units having the formula (a) and recurring units having the formula (b).

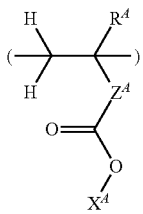

(a)

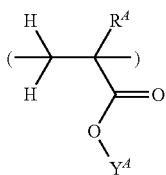

(b)

Herein $R^A$ is hydrogen, fluorine, methyl or trifluoromethyl, $Z^A$ is a single bond, phenylene group, naphthylene group or (backbone)-C(=O)—O—Z'—, Z' is a $C_1$-$C_{10}$ straight, branched or cyclic alkylene group which may contain a hydroxyl radical, ether bond, ester bond or lactone ring, or phenylene group or naphthylene group, $X^A$ is an acid labile group, and $Y^A$ is hydrogen or a polar group having at least one structure selected from the group consisting of hydroxyl, cyano, carbonyl, carboxyl, ether bond, ester bond, sulfonic acid ester bond, carbonate bond, lactone ring, sultone ring and carboxylic anhydride.

The resist composition may further comprise an organic solvent.

The resist composition may further comprise a photoacid generator other than the photoacid generator defined above.

Preferably the other photoacid generator has the formula (5) or (6).

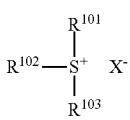

(5)

Herein $R^{101}$, $R^{102}$ and $R^{103}$ are each independently a $C_1$-$C_{20}$ straight, branched or cyclic monovalent hydrocarbon group which may contain a heteroatom, any two of $R^{101}$, $R^{102}$ and $R^{13}$ may bond together to form a ring with the sulfur atom to which they are attached, $X^-$ is an anion selected from the formulae (5A) to (5D):

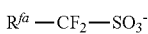

(5A)

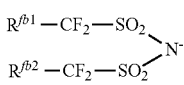

(5B)

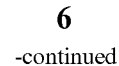

(5C)

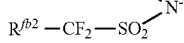

(5D)

wherein $R^{fa}$, $R^{fb1}$, $R^{fb2}$, $R^{fc1}$, $R^{fc2}$ and $R^{fc3}$ are each independently fluorine or a $C_1$-$C_{40}$ straight, branched or cyclic monovalent hydrocarbon group which may contain a heteroatom, or a pair of $R^{fb1}$ and $R^{fb2}$, or $R^{fc1}$ and $R^{fc2}$ may bond together to form a ring with the carbon atoms to which they are attached and any intervening atoms, $R^{fd}$ is a $C_1$-$C_{40}$ straight, branched or cyclic monovalent hydrocarbon group which may contain a heteroatom.

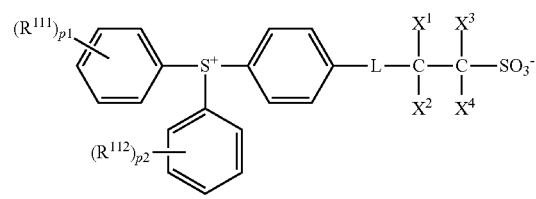

(6)

Herein $R^{111}$ and $R^{112}$ are each independently a $C_1$-$C_{20}$ straight, branched or cyclic alkyl group, p1 and p2 are each independently an integer of 0 to 5, L is a single bond, ether bond, or a $C_1$-$C_{20}$ straight, branched or cyclic divalent hydrocarbon group which may contain a heteroatom, $X^1$, $X^2$, $X^3$ and $X^4$ are each independently hydrogen, fluorine or trifluoromethyl, at least one of $X^1$, $X^2$, $X^3$ and $X^4$ being a substituent group other than hydrogen.

The resist composition may further comprise an onium salt having the formula (7) or (8).

(7)

(8)

Herein $R^{151}$ and $R^{152}$ are each independently hydrogen or a $C_1$-$C_{40}$ straight, branched or cyclic monovalent hydrocarbon group which may contain a heteroatom, excluding the hydrocarbon group in which the hydrogen atom bonded to the carbon at α-position relative to the sulfo group is substituted by fluorine or fluoroalkyl, and $M^+$ is an onium cation.

The resist composition may further comprise an amine compound.

The resist composition may further comprise a surfactant which is insoluble or substantially insoluble in water and soluble in alkaline developer, and/or a surfactant which is insoluble or substantially insoluble in water and alkaline developer.

In a fourth aspect, the invention provides a pattern forming process comprising the steps of applying the resist composition defined above onto a substrate, prebaking to form a resist film, exposing a selected region of the resist film to KrF excimer laser, ArF excimer laser, EB or EUV through a photomask, baking, and developing the exposed resist film in a developer.

In a preferred embodiment, the developing step uses an alkaline aqueous solution as the developer, thereby forming a positive pattern in which an exposed region of the resist film is dissolved away and an unexposed region of the resist film is not dissolved.

In a preferred embodiment, the developing step uses an organic solvent as the developer, thereby forming a negative pattern in which an unexposed region of the resist film is dissolved away and an exposed region of the resist film is not dissolved. More preferably, the organic solvent is at least one solvent selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

In a preferred embodiment, the exposure step is carried out by immersion lithography while a liquid having a refractive index of at least 1.0 is held between the resist film and a projection lens.

The process may further comprise the step of coating a protective film on the resist film prior to the exposure step, wherein immersion lithography is carried out while the liquid is held between the protective film and the projection lens.

Advantageous Effects Of Invention

The inventive sulfonium compound is fully soluble and uniformly dispersible in an organic solvent and contains an acid-eliminatable substituent group which is effective for improving contrast. A resist composition comprising the sulfonium compound forms a pattern having high resolution, reduced LWR and rectangular profile when processed by lithography.

DESCRIPTION OF THE PREFERRED EMBODIMENTS

Figure 1:
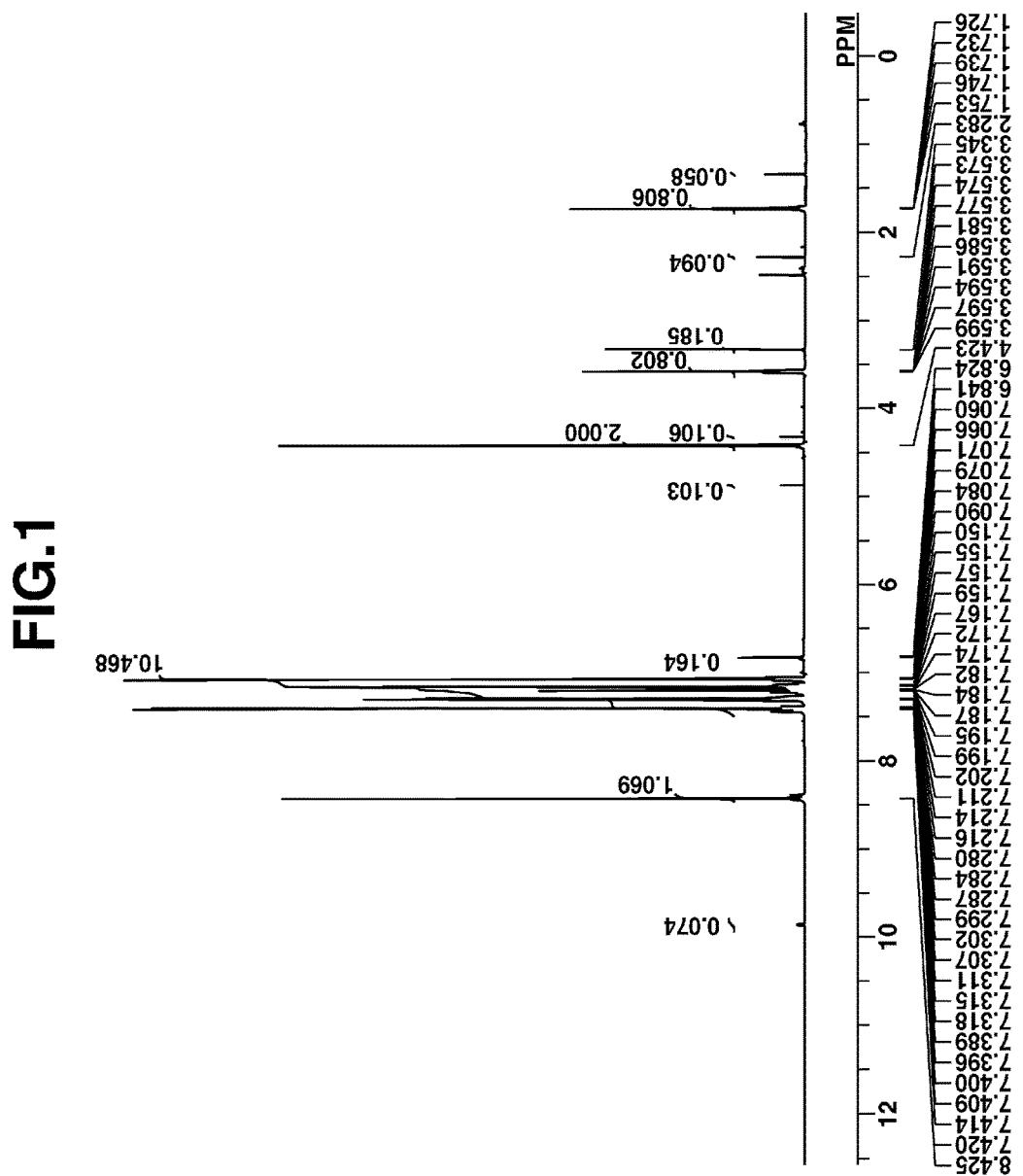
FIGS. 1 and 2 are diagrams showing $^1$H- and $^{19}$F-NMR spectra of the compound of Example 1-1, respectively.

The singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. In chemical formulae, the broken line denotes a valence bond; Me stands for methyl, Ac for acetyl, and Ph for phenyl.

The abbreviations have the following meaning.
DUV: deep ultraviolet
EUV: extreme ultraviolet
EB: electron beam
PAG: photoacid generator
PEB: post-exposure bake
LWR: line width roughness
DOF: depth of focus The term "high-energy radiation" is intended to encompass KrF excimer laser, ArF excimer laser, EB, and EUV.

Sulfonium Compound

The invention provides a sulfonium compound having the formula (1A), (1B) or (1C).

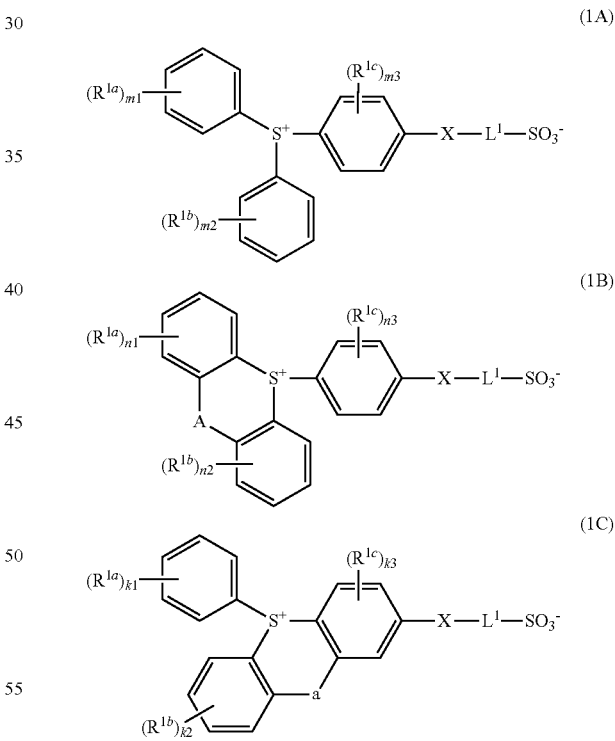

Herein $L^1$ is a $C_1$-$C_{20}$ straight, branched or cyclic divalent hydrocarbon group which may contain a heteroatom-containing radical. X is a divalent linking group. A is a single bond, methylene group, carbonyl group, sulfinyl group, sulfonyl group, amino group, ether bond, thioether bond, ester bond, carbonate bond, carbamate bond or sulfonic acid ester bond. $R^{1a}$ to $R^{1c}$ are each independently a $C_1$-$C_{20}$ straight, branched or cyclic monovalent hydrocarbon group which may contain a heteroatom-containing radical, with the proviso that where at least two groups $R^{1a}$ are included, two of them may bond together to from a ring with the carbon atoms on the benzene ring to which they are attached, where at least two groups $R^{1b}$ are included, two of them may bond together to from a ring with the carbon atoms on the benzene ring to which they are attached, and where at least two groups $R^{1c}$ are included, two of them may bond together to from a ring with the carbon atoms on the benzene ring to which they are attached. The subscripts m1, m2 and m3 are integers meeting $0 \le m1 \le 5$, $0 \le m2 \le 5$, $0 \le m3 \le 4$, and $m1+m2+m3 \ge 1$, n1, n2 and n3 are integers meeting $0 \le n1 \le 4$, $0 \le n2 \le 4$, $0 \le n3 \le 4$, and $n1+n2+n3 \ge 1$, k1, k2 and k3 are integers meeting $0 \le k1 \le 5$, $0 \le k2 \le 4$, $0 \le k3 \le 3$, and $k1+k2+k3 \ge 1$.

At least one of $R^{1a}$ to $R^{1c}$ is a group having the following formula (2).

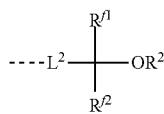

(2)

In formula (2), $L^2$ is a $C_1$-$C_{20}$ straight, branched or cyclic divalent hydrocarbon group which may contain a heteroatom-containing radical. $R^2$ is an acid-eliminatable group. $R^{f1}$ and $R^{f2}$ are each independently hydrogen, $C_1$-$C_{20}$ straight, branched or cyclic alkyl group, fluorine, or $C_1$-$C_{20}$ straight, branched or cyclic fluoroalkyl group which is substituted with at least one fluorine atom, at least one of $R^{f1}$ and $R^{f2}$ is fluorine or fluoroalkyl.

Suitable divalent hydrocarbon groups represented by $L^1$ and $L^2$ include linear alkane diyl groups such as methylene, ethylene, propane-1,3-diyl, butano-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl; saturated cyclic hydrocarbon groups such as cydopentanediyl, cyclohexanediyl, norbornanediyl, and adamantanediyl; and unsaturated cyclic hydrocarbon groups such as phenylene and naphthylene. Also included are the foregoing groups in which at least one hydrogen atom is replaced by an alkyl radical such as methyl, ethyl, propyl, n-butyl or t-butyl, or in which at least one hydrogen atom is replaced by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl radical, cyano radical, carbonyl radical, ether bond, ester bond, sulfonic acid ester bond, carbonate bond, lactone ring, sultone ring, carboxylic acid anhydride or haloalkyl radical.

Examples of the divalent linking group represented by X include an ether bond, thioether bond, ester bond, sulfonic acid ester bond, amide bond, carbonate bond, and carbamate bond. Inter alia, an ether bond, thioether bond and ester bond are preferred.

In formula (2), the acid-eliminatable group $R^2$ is a substituent which is eliminated under the action of acid, leaving a hydroxyl group in formula (2), so that —$OR^2$ becomes a group of acetal structure or tertiary ether structure, for example. Examples of the $C_1$-$C_{20}$ alkyl group represented by $R^{f1}$ and $R^{f2}$ include methyl, ethyl, propyl, isopropyl, n-butyl, s-butyl, t-butyl, t-pentyl, n-pentyl, n-hexyl, n-octyl, n-nonyl, n-decyl, cyclopentyl, cyclohexyl, 2-ethylhexyl, cyclopentyl-methyl, cyclopentylethyl, cyclopentylbutyl, cyclobhexylm-ethyl, cyclohexylethyl, cyclohexylbutyl, norbornyl, tricyclo [5.2.1.0$^{2,6}$]decanyl, adamantyl and adamantylmethyl. Examples of the $C_1$-$C_{20}$ fluoroalkyl group include the foregoing alkyl groups in which one or more hydrogen is substituted by a fluorine atom(s). Preferably $R^{f1}$ and $R^{f2}$ each are trifluoromethyl.

In formulae (1A), (1B) and (1C), suitable monovalent hydrocarbon groups represented by $R^{1a}$ to $R^{1c}$ include alkyl groups such as methyl, ethyl, propyl, isopropyl, n-butyl, s-butyl, t-butyl, t-pentyl, n-pentyl, n-hexyl, n-octyl, n-nonyl, n-decyl, cyclopentyl, cyclohexyl, 2-ethylhexyl, cyclopentyl-methyl, cyclopentylethyl, cyclopentylbutyl, cyclohexylm-ethyl, cyclohexylethyl, cyclohexylbutyl, norbornyl, tricyclo [5.2.1.0$^{2,6}$]decanyl, adamantyl and adamantylmethyl; and aryl groups such as phenyl, naphthyl and anthracenyl. Also included are the foregoing groups in which at least one hydrogen atom is substituted by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl radical, cyano radical, carbonyl radical, ether bond, ester bond, sulfonic acid ester bond, carbonate bond, lactone ring, sultone ring, carboxylic acid anhydride or haloalkyl radical.

Of the sulfonium compounds having formulae (1A), (1B) and (1C), compounds having the following formulae (3A), (3B) and (3C) are preferred.

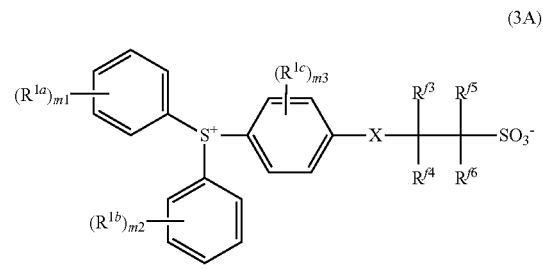

(3A)

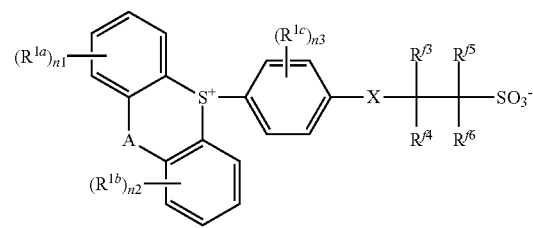

(3B)

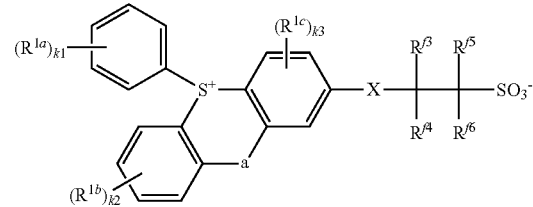

(3C)

Herein $R^{1a}$, $R^{1b}$, $R^{1c}$, $R^{1c}$, X, A, m1, m2, m3, n1, n2, n3, k1, k2, and k3 are as defined above. $R^{f3}$, $R^{f4}$, $R^{f5}$ and $R^{f6}$ are each independently hydrogen, fluorine or trifluoromethyl.

Preferably, at least one of $R^{f3}$, $R^{f4}$, $R^{f5}$ and $R^{f6}$ is fluorine or trifluoromethyl because the corresponding sulfonium compound may generate an acid having a high acidity sufficient to cleave the acid labile groups on the base resin efficiently. More preferably both $R^{f5}$ and $R^{f6}$ are fluorine. That is, those compounds having fluorine at α-position relative to the sulfo group, as represented by the following formulae (4A), (4B) and (4C), are more preferred because the generated acid has a higher acidity.

(4A)
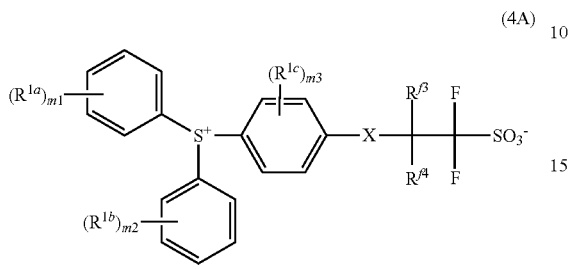

(4B)
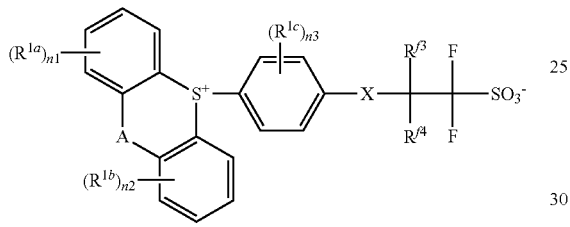

(4C)
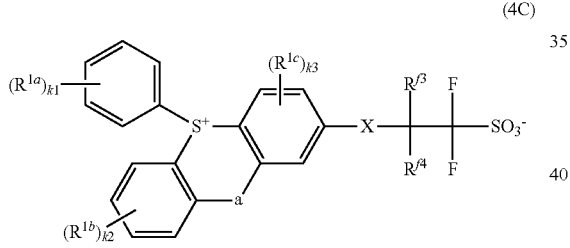

Herein $R^{1a}$, $R^{1b}$, $R^{1c}$, X, A, $R^{f3}$, $R^{f4}$, m1 m2, m3, n1, n2, n3, k1, k2, and k3 are as defined above.

Examples of the sulfonium compound having formula (1A) are shown below, but not limited thereto.

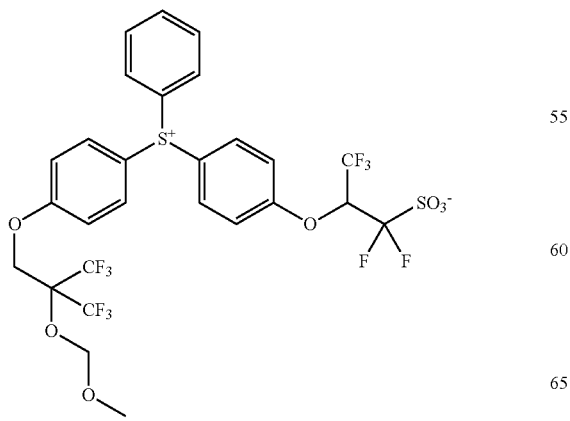

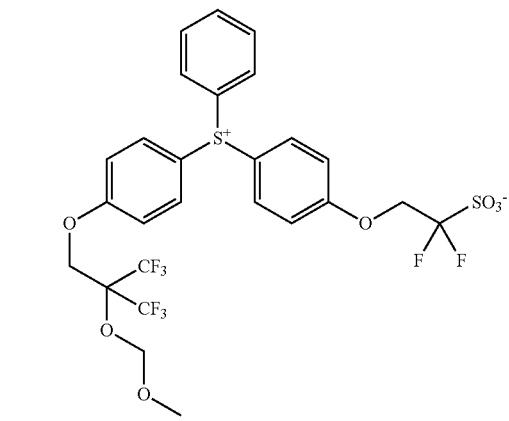

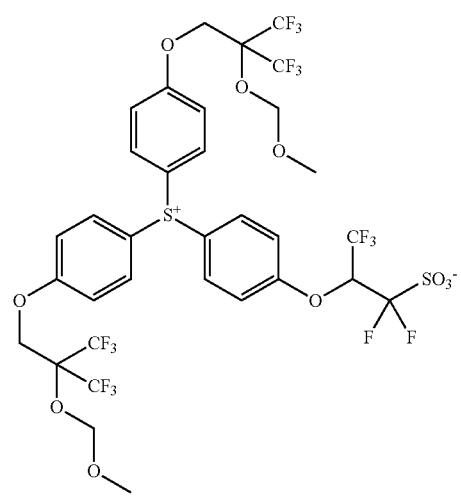

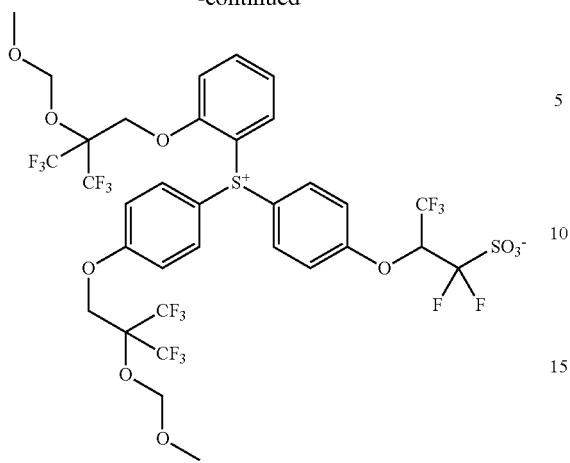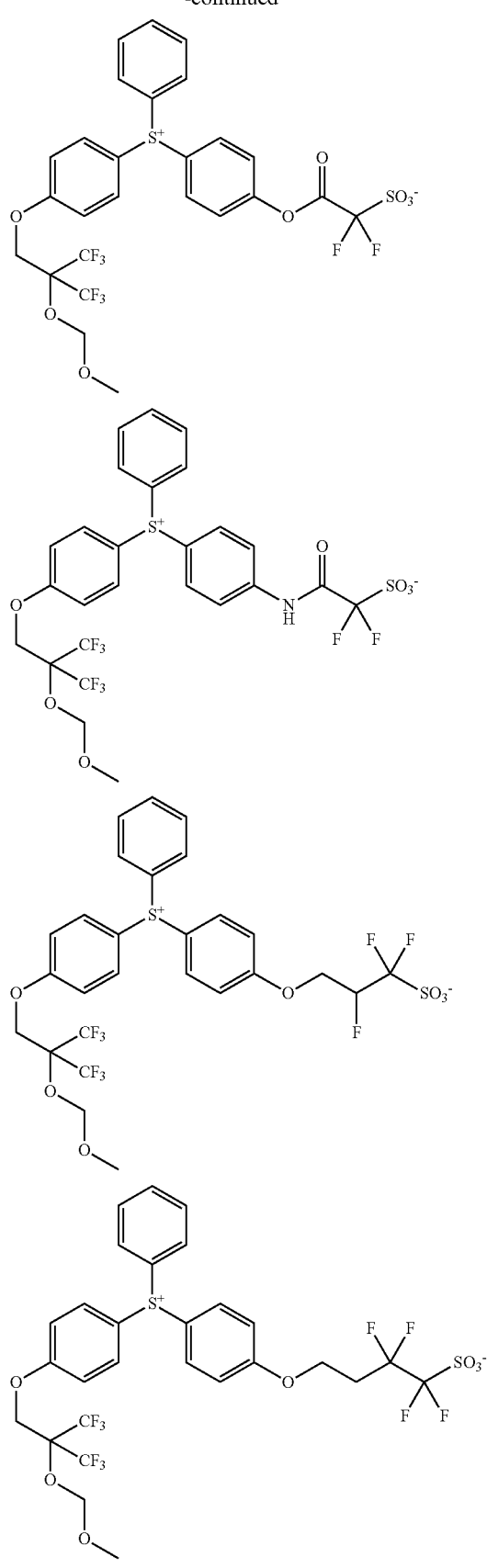

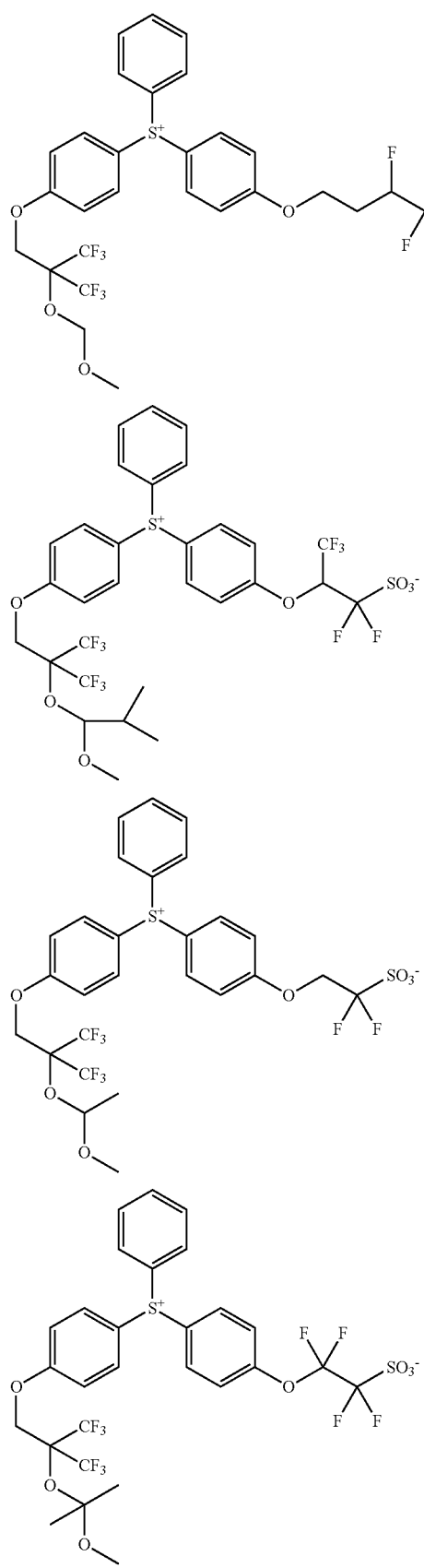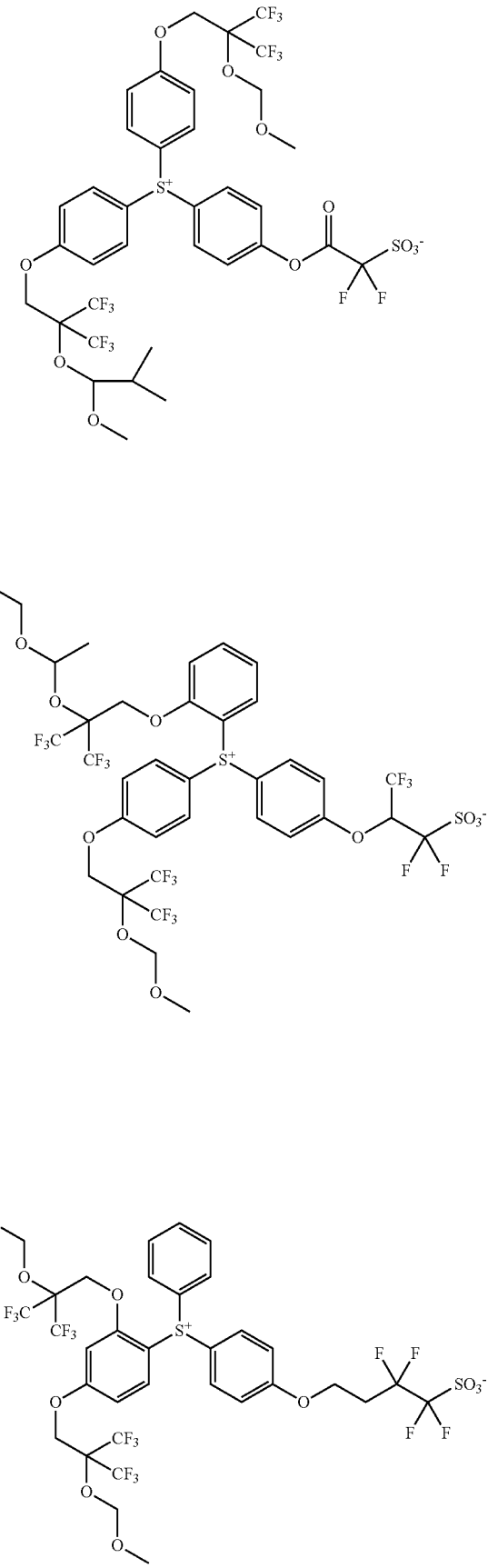

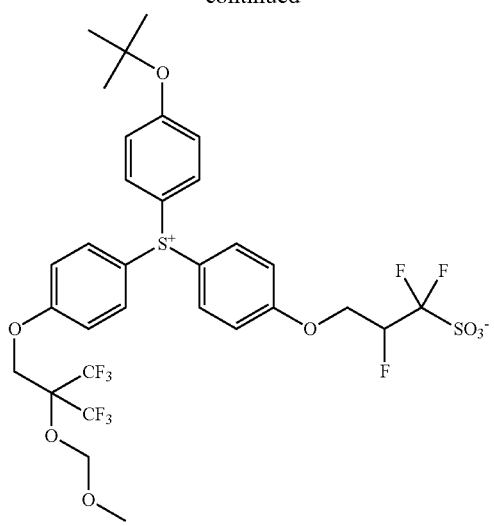
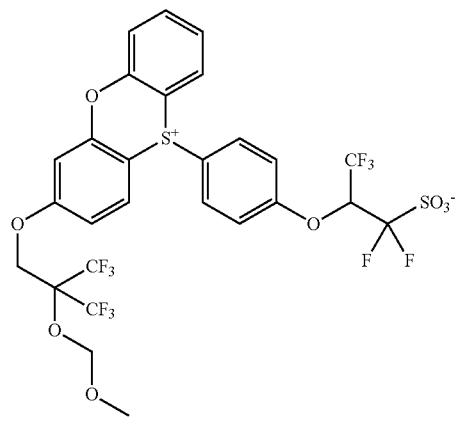
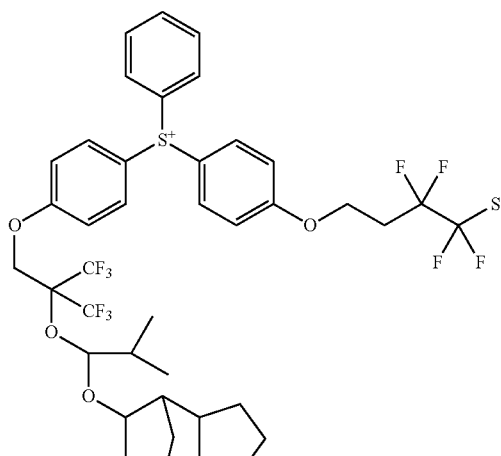
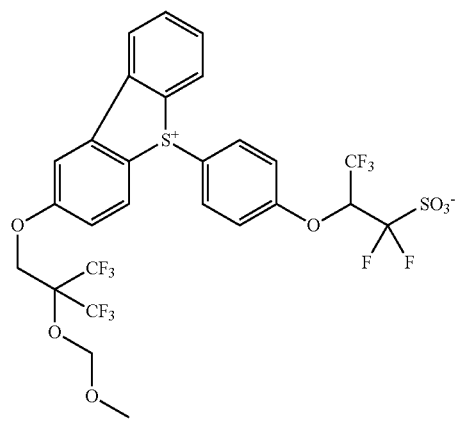
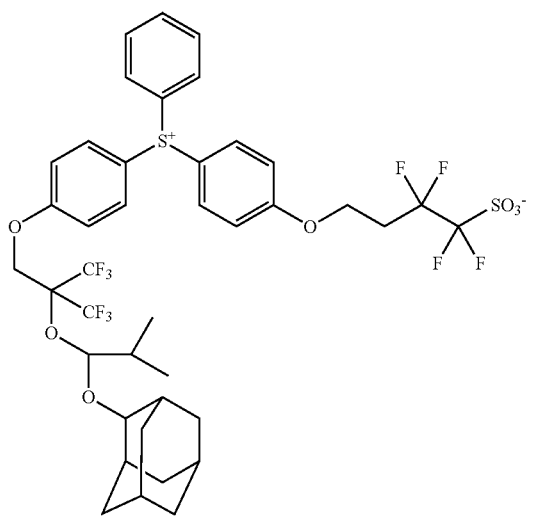
Examples of the sulfonium compound having formula (1B) are shown below, but not limited thereto.
Examples of the sulfonium compound having formula (1C) are shown below, but not limited thereto.
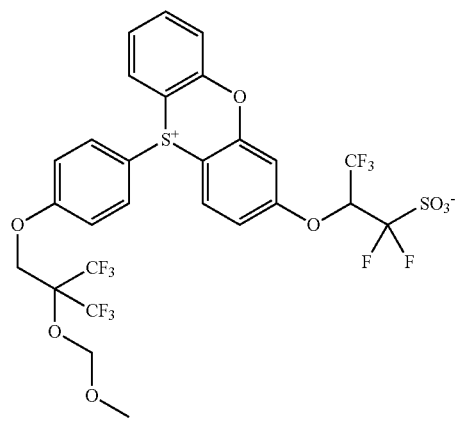

-continued

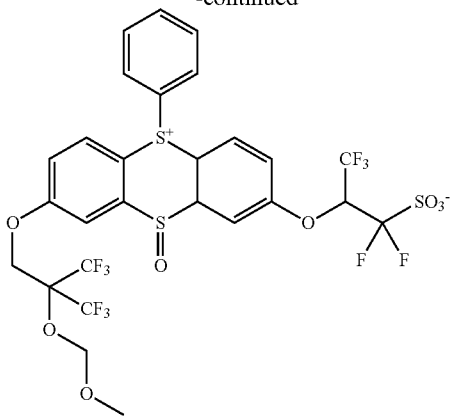

The sulfonium compound of the invention is characterized by a betaine structure. The sulfonium compound of betaine structure generates an acid of bulky structure, indicating that acid diffusion is controllable at a high level. In general, when the generated acid is of bulky structure, acid diffusion is reduced.

As compared with a resist composition comprising an acid generator of betaine structure as described in Patent Document 5, for example, the resist composition comprising the betaine type sulfonium compound according to the invention is superior in resolution and LWR. Although the reason is not well understood, the following two reasons are probable.

One reason is that the inventive sulfonium compound possesses the fluorinated substituent, i.e., partial structure having formula (2), which exerts an effect of improving solvent solubility. Although betaine compounds generally lack solvent solubility because of high polarity, the inventive sulfonium compound possesses the fluorinated substituent which contributes to an improvement in solvent solubility. Consequently the sulfonium compound is uniformly dispersed in the resist composition whereby LWR is improved.

Another reason is that the partial structure of formula (2) has an acid-eliminatable group ($R^2$). In the exposed region, the sulfonium compound creates a fluoroalcohol site as a result of the acid-eliminatable group being eliminated from the partial structure. Consequently, the exposed region of resist film becomes more soluble in the positive tone process via alkaline aqueous solution development or inversely, more insoluble in the negative tone process via organic solvent development. Consequently, the contrast between exposed and unexposed regions is enhanced, suggesting that resolution is improved.

These phenomena are quite unexpected from Patent Document 5. In this sense, the sulfonium compound of the invention is novel and of great worth.

Described below is the synthesis of the sulfonium compound of the invention. Reference is made to the synthesis of the sulfonium compound having formula (1A) wherein X is an ether bond as a typical example. While there are several synthesis routes, one typical route is by reaction of a sulfoalkyloxybenzene or sulfoaryloxybenzene with a diaryl sulfoxide in the presence of an acid catalyst. The reaction is outlined below as Scheme A.

Scheme A

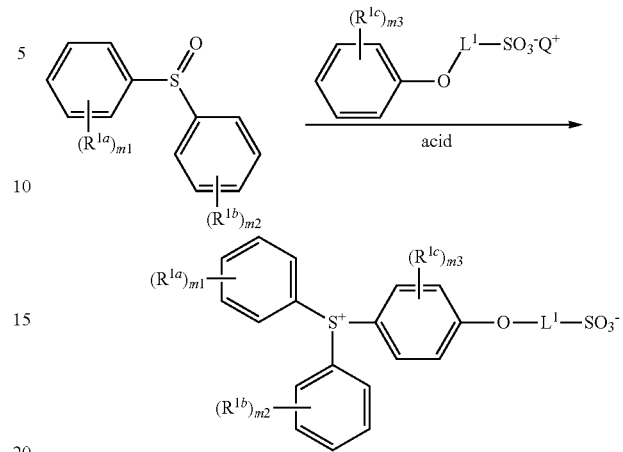

Herein $R^{1a}$, $R^{1b}$, $R^{1c}$, m1, m2, m3, and $L^1$ are as defined above, and $Q^+$ is an alkali metal ion such as sodium or potassium ion, ammonium ion, or proton. In this reaction, methanesulfonic acid or the like may be used as the acid catalyst.

Another route is by nucleophilic displacement reaction of a 4-fluorophenyldiphenylsulfonium compound with a sulfoalcohol. The reaction is outlined below as Scheme B.

Scheme B

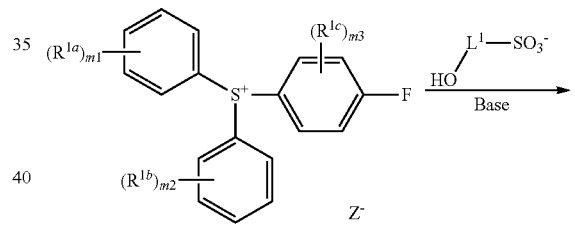

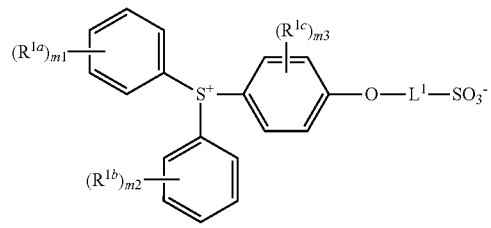

Herein $R^{1a}$, $R^{1b}$, $R^{1c}$, m1, m2, m3, and $L^1$ are as defined above. Z is a chloride, bromide, iodide, methylsulfate or p-toluenesulfonate ion. Although Scheme B refers to the 4-fluorophenyldiphenylsulfonium compound, similar reaction is possible with any 4-halophenyldiphenylsulfonium compounds.

Further, the sulfonium compound may be synthesized by intramolecular reaction according to the following Scheme C.

Scheme C

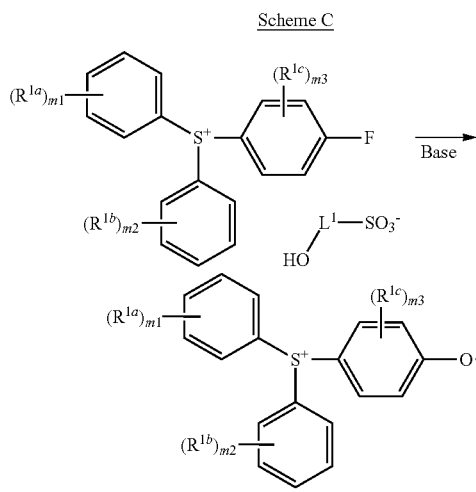

Herein $R^{1a}$, $R^{1b}$, $R^{1c}$, m1, m2, m3, and $L^1$ are as defined above.

As still further synthesis routes, the sulfonium compound may be synthesized by utilizing addition reaction of a hydrogensulfite ion to a sulfonium salt having terminal olefin, or reaction of a corresponding halide with a sulfur compound. For example, the addition reaction is outlined below as Scheme D.

Scheme D

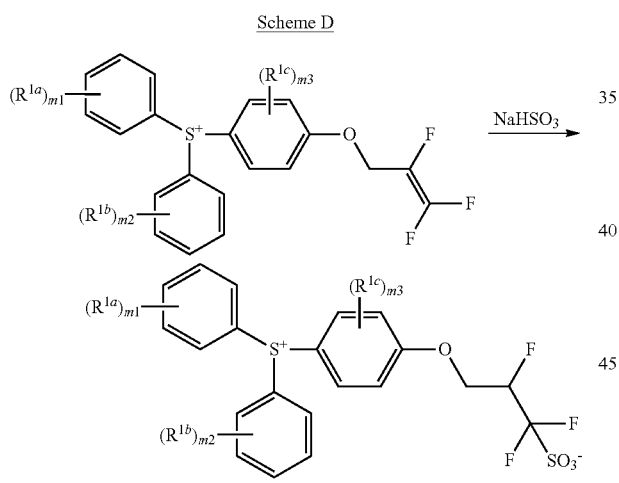

Herein $R^{1a}$, $R^{1b}$, $R^{1c}$, m1, m2, and m3 are as defined above.

The synthesis routes described above are merely exemplary, and the method of preparing the sulfonium compound of the invention is not limited thereto.

Resist Composition

Another embodiment of the invention is a resist composition comprising (A) a photoacid generator in the form of a sulfonium compound having formula (1A), (1B) or (1C) as an essential component. The resist composition may further comprise:

(B) a base resin, (C) an organic solvent, (D) a photoacid generator other than the sulfonium compound having formula (1A), (1B) or (1C) (also referred to as second photoacid generator), (E) a quencher, and (F) a surfactant which is insoluble or substantially insoluble in water and soluble in alkaline developer, and/or a surfactant which is insoluble or substantially insoluble in water and alkaline developer (also referred to as hydrophobic resin). Components (D), (B), and (F) are optional, that is, may be added if necessary.

In the resist composition, an appropriate amount of the PAG as component (A) is 0.1 to 40 parts by weight, more preferably 1 to 20 parts by weight per 100 parts by weight of the base resin (B). As long as the amount is within the range, the component exerts a full function of photoacid generator, eliminating any performance degradations including a drop of sensitivity, solubility shortage, and foreign particles. The PAG may be used alone or in admixture of two or more.

(B) Base Resin

The base resin used herein as component (B) preferably contains a polymer comprising recurring units having the formula (a) and recurring units having the formula (b).

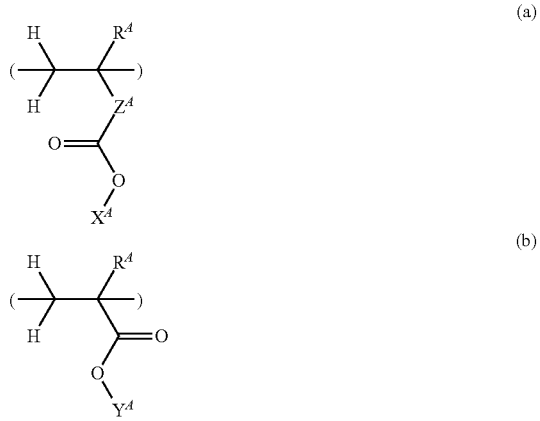

In formulae (a) and (b), $R^A$ is hydrogen, fluorine, methyl or trifluoromethyl. $Z^A$ is a single bond, phenylene group, naphthylene group or (backbone)-C(=O)—O—Z'—, wherein Z' is a $C_1$-$C_{10}$ straight, branched or cyclic alkylene group which may contain a hydroxyl radical, ether bond, ester bond or lactone ring, or phenylene group or naphthylene group. $X^A$ is an acid labile group. $Y^A$ is hydrogen or a polar group having at least one structure selected from among hydroxyl, cyano, carbonyl, carboxyl, ether bond, ester bond, sulfonic acid ester bond, carbonate bond, lactone ring, sultone ring and carboxylic anhydride.

Examples of the structure having formula (a) wherein $Z^A$ is a variant are shown below, but not limited thereto. Notably, $R^A$ and $X^A$ are as defined above.

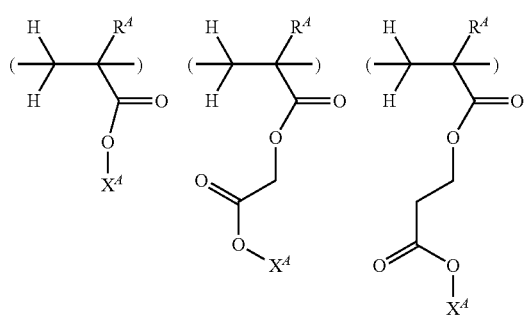

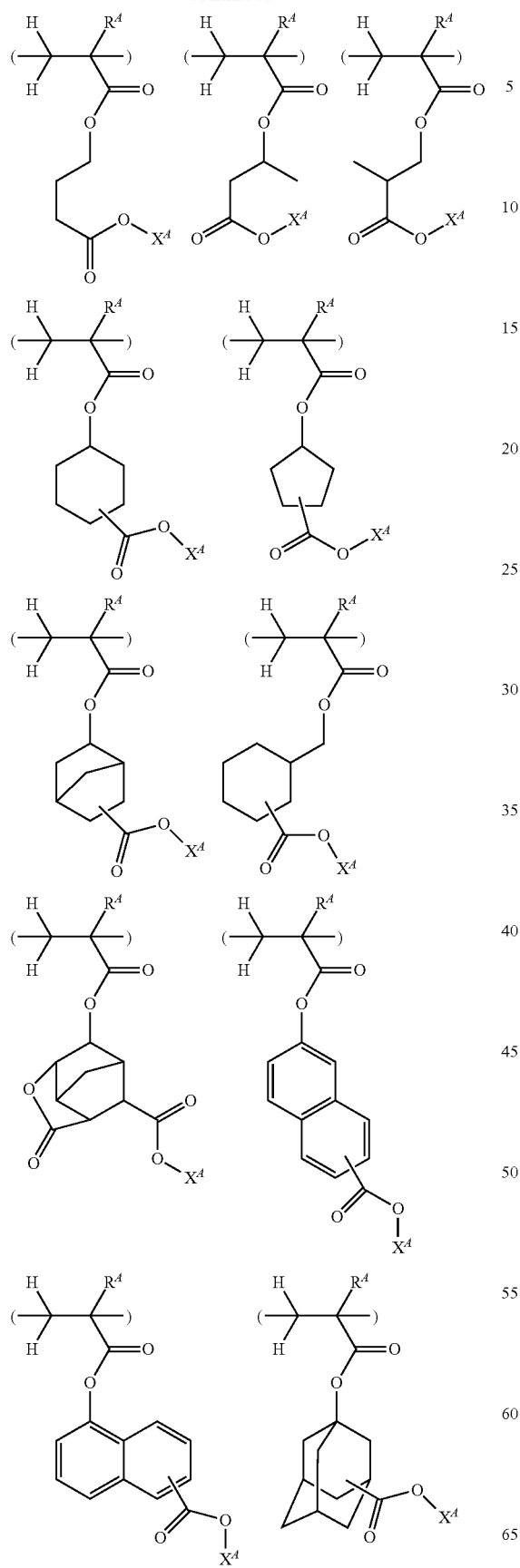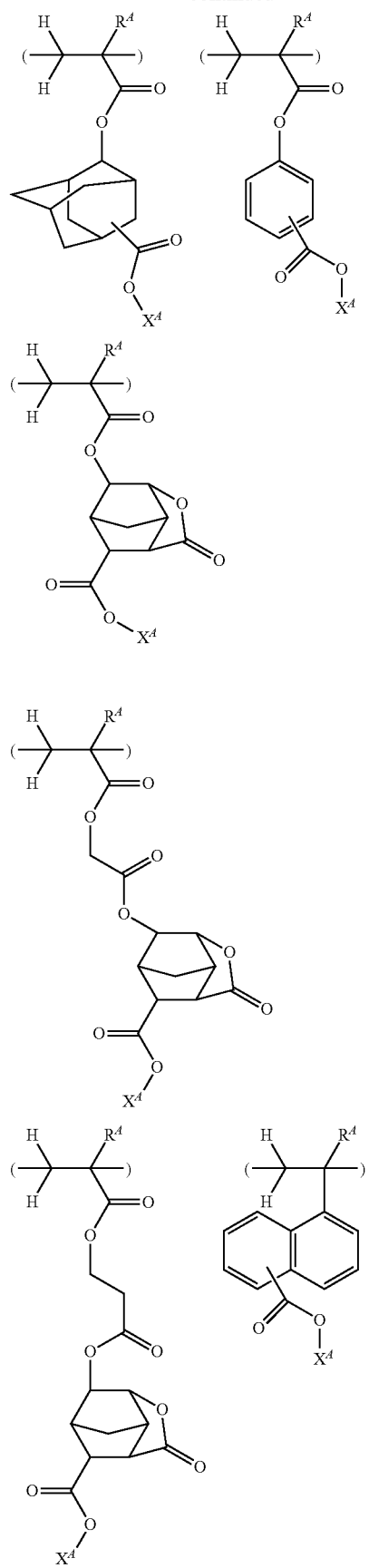

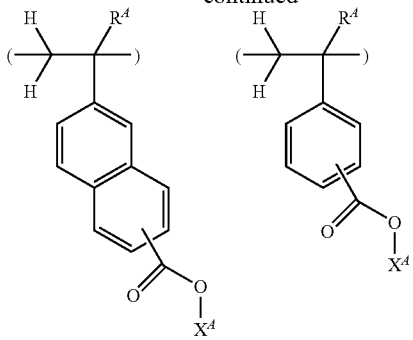

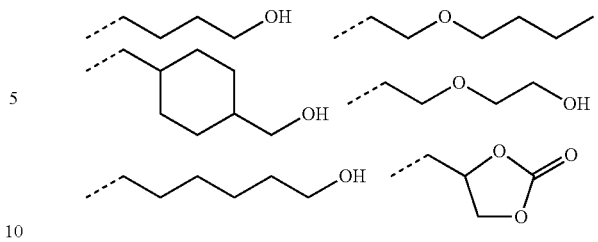

Under the action of acid, a polymer comprising recurring units of formula (a) is decomposed to generate carboxylic acid, turning to be an alkali soluble polymer.

The acid labile group represented by $X^A$ may be selected from a variety of such groups. Examples of the acid labile group include groups of the following formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

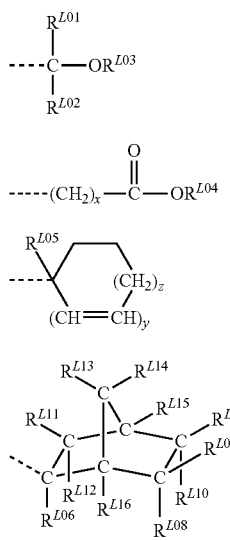

In formula (L1), $R^{L01}$ and $R^{L02}$ each are hydrogen or a straight, branched or cyclic alkyl group of 1 to 18 carbon atoms, preferably 1 to 10 carbon atoms. Exemplary alkyl groups include methyl, ethyl, propyl, isopropyl, n-butyl, s-butyl, t-butyl, cyclopentyl, cyclohexyl, 2-ethylhexyl, n-octyl, norbonyl, tricyclodecanyl, tetracyclododecanyl, and adamantyl. $R^{L03}$ is a monovalent hydrocarbon group of 1 to 18 carbon atoms, preferably 1 to 10 carbon atoms, which may contain a heteroatom such as oxygen, examples of which include unsubstituted straight, branched or cyclic alkyl groups and substituted forms of such alkyl groups in which some hydrogen atoms are replaced by hydroxyl, alkoxy, oxo, amino, alkylamino or the like, or in which a heteroatom such as oxygen intervenes between carbon atoms. Suitable alkyl groups are as exemplified above for $R^{L01}$ and $R^{L02}$. Illustrative examples of the substituted alkyl groups are shown below.

A pair of $R^{L01}$ and $R^{L02}$, $R^{L01}$ and $R^{L03}$, or $R^{L02}$ and $R^{103}$ may bond together to form a ring with the carbon and oxygen atoms to which they are attached. Ring-forming participants of $R^{L01}$, $R^{L02}$ and $R^{L03}$ represent a straight or branched alkylene group of 1 to 18 carbon atoms, preferably 1 to 10 carbon atoms.

In formula (L2), $R^{L04}$ is a tertiary alkyl group of 4 to 20 carbon atoms, preferably 4 to carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are t-butyl, t-pentyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, l-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-t-butylsilyl. Exemplary oxoalkyl groups are 3-oxocyclohexyl, 4-methyl-2-oxooxan-4-yl, and 5-methyl-2-oxooxolan-5-yl. Letter x is an integer of 0 to 6.

In formula (13), $R^{L05}$ is a substituted or unsubstituted, straight, branched or cyclic $C_1$-$C_8$ alkyl group or a substituted or unsubstituted $C_6$-$C_{20}$ aryl group. Examples of the optionally substituted alkyl group include straight, branched or cyclic alkyl groups such as methyl, ethyl, propyl, isopropyl, n-butyl, s-butyl, t-butyl, t-pentyl, n-pentyl, n-hexyl, cyclopentyl, and cyclohexyl, and substituted forms of such groups in which some hydrogen atoms are substituted by hydroxyl, alkoxy, carboxyl, alkoxycarbonyl, oxo, amino, alkylamino, cyano, mercapto, alkylthio, sulfo or the like. Examples of the optionally substituted aryl groups include phenyl, methylphenyl, naphthyl, anthryl, phenanthryl, and pyrenyl, and substituted forms of such groups in which some hydrogen atoms are substituted by hydroxyl, alkoxy, carboxyl, alkoxycarbonyl, oxo, amino, alkylamino, cyano, mercapto, alkylthio, sulfo or the like. Letter y is equal to 0 or 1, z is equal to 0, 1, 2 or 3, and 2y+z is equal to 2 or 3.

In formula (L4), $R^{L06}$ is an optionally substituted $C_1$-$C_8$ straight, branched or cyclic alkyl group or optionally substituted $C_6$-$C_{20}$ aryl group. Examples of these groups are the same as exemplified for $R^{L05}$.

$R^{L07}$ to $R^{L16}$ independently represent hydrogen or optionally substituted $C_1$-$C_{15}$ monovalent hydrocarbon groups. Exemplary hydrocarbon groups are straight, branched or cyclic alkyl groups such as methyl, ethyl, propyl, Isopropyl, n-butyl, s-butyl, t-butyl, t-pentyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxyl, alkoxycarbonyl, oxo, amino, alkylamino, cyano, mercapto, alkylthio, sulfo or the like. Alternatively, two of $R^{L07}$ to $R^{L16}$, taken together, form a ring with the carbon atom to which they are attached (for example, a pair of $R^{L07}$ and $R^{L08}$, $R^{L07}$ and $R^{L09}$, $R^{L07}$ and $R^{L10}$, $R^{L08}$ and $R^{L10}$, $R^{L09}$ and $R^{L10}$, $R^{L11}$ and $R^{L12}$, or $R^{L13}$ and $R^{L14}$ form a ring). Ring-forming participants of $R^{L07}$ to $R^{L16}$ represent a divalent $C_1$-$C_{15}$ hydrocarbon group, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or $R^{L14}$ and $R^{L15}$).

Of the acid labile groups of formula (L1), the straight and branched ones are exemplified by the following groups.

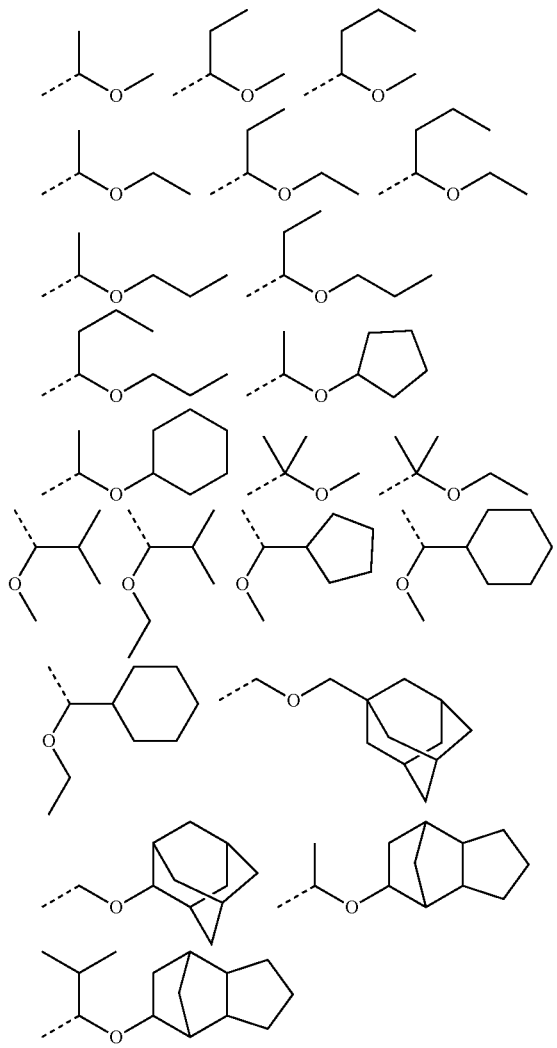

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile group of formula (L2) include t-butoxycarbonyl, t-butoxycarbonylmethyl, t-pentyloxycarbonyl, t-pentyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1 ethoxyethoxycarbonylmethyl, 2 tetrahydropyranyloxycarbonylmethyl, and 2-tetrahydrofuranyloxycarbonylmethyl.

Examples of the acid labile group of formula (L3) include 1-methylcyclopentyl, 1-ethylcyclopentyl, 1-n-propylcyclopentyl, 1-isopropylcyclopentyl, 1-n-butylcyclopentyl, 1-s-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexan-3-yl, and 3-ethyl-1-cyclohexen-3-yl.

Of the acid labile groups having formula (LA), groups having the following formulas (L4-1) to (L4-4) are preferred.

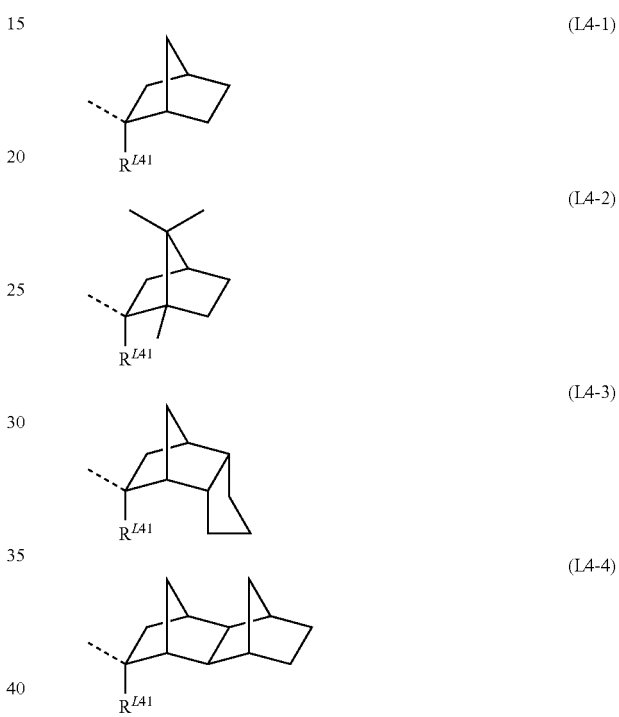

In formulas (L4-1) to (L4-4), the broken line denotes a bonding site and direction. $R^{L41}$ is each independently a monovalent hydrocarbon group, typically a $C_1$-$C_{10}$ straight, branched or cyclic alkyl group, such as methyl, ethyl, propyl, isopropyl, n-butyl, s-butyl, t-butyl, t-pentyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. When $X^A$ is an acid labile group of formula (L4), a plurality of stereoisomers may be contained.

For example, the formula (L4-3) represents one or a mixture of two selected from groups having the following formulas (L4-3-1) and (L4-3-2).

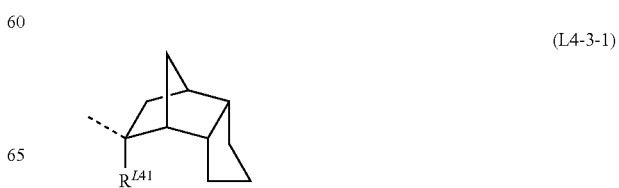

-continued (L4-3-2)

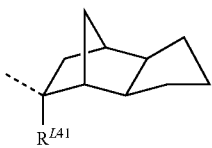

Similarly, the formula (L4-4) represents one or a mixture of two or more selected from groups having the following formulas (L4-4-1) to (L4-4-4).

(L4-4-1)

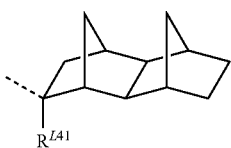

(L4-4-2)

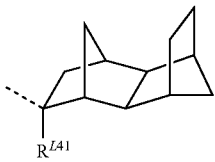

(L4-4-3)

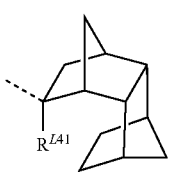

(L4-4-4)

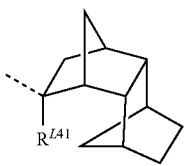

Herein $R^{L41}$ is as defined above.

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1]heptane ring, which ensures high reactivity for acid catalyzed elimination reaction (see JP-A 2000-336121). In preparing these monomers having a tertiary exo-alkyl group of bicyclo[2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

(L4-1-endo)

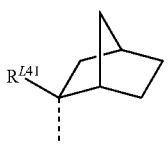

-continued (L4-2-endo)

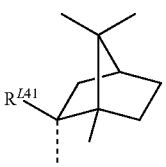

(L4-3-endo)

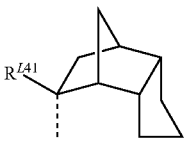

(L4-4-endo)

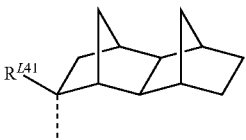

Herein $R^{L41}$ is as defined above.

Illustrative examples of the acid labile group of formula (L4) are given below.

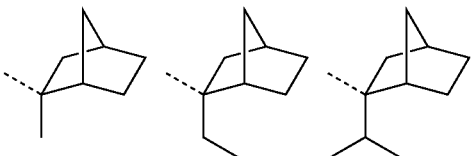

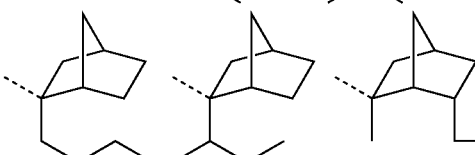

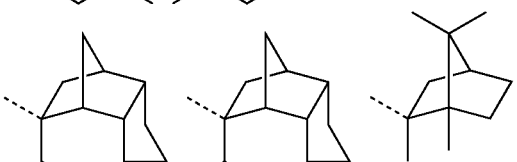

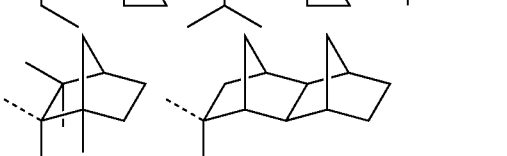

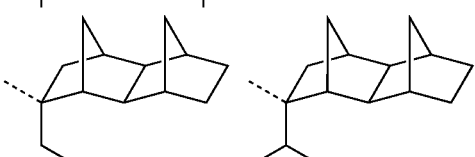

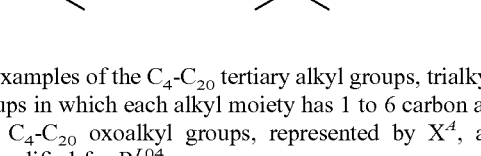

Examples of the $C_4$-$C_{20}$ tertiary alkyl groups, trialkylsilyl groups in which each alkyl moiety has 1 to 6 carbon atoms, and $C_4$-$C_{20}$ oxoalkyl groups, represented by $X^A$, are as exemplified for $R^{LO4}$.

Illustrative examples of the recurring units of formula (a) are given below, but not limited thereto. Herein $R^A$ is as defined above.

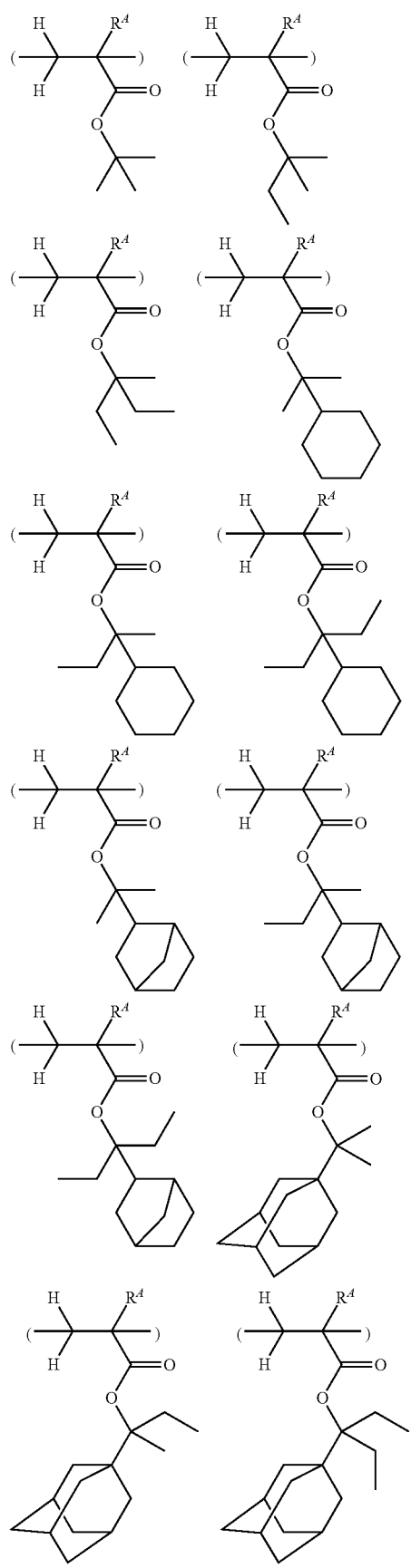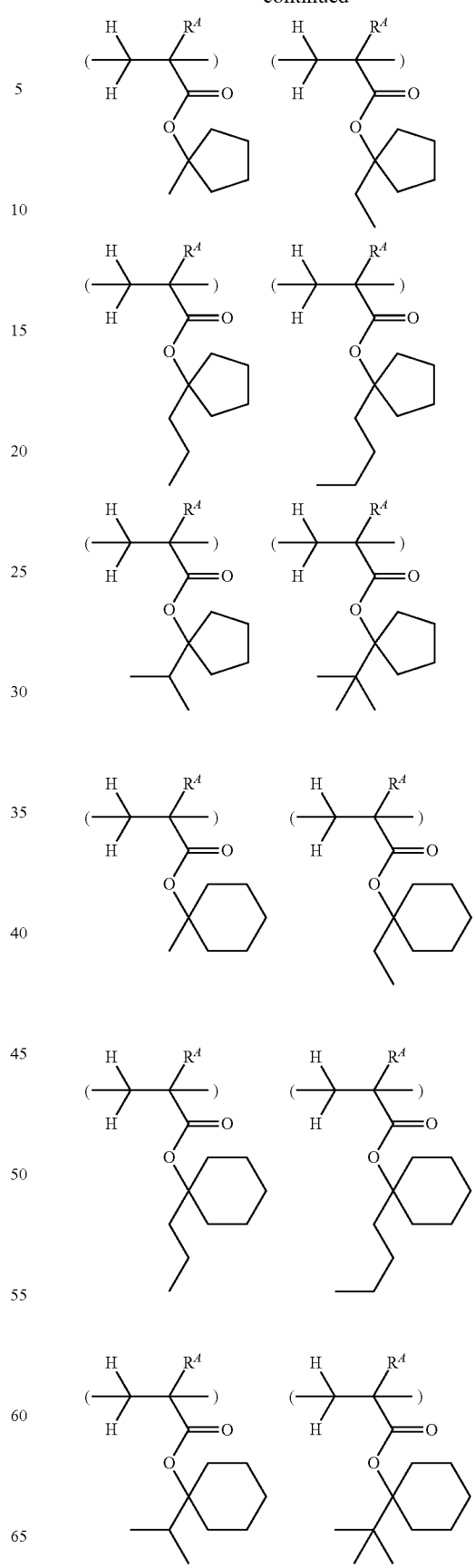

-continued
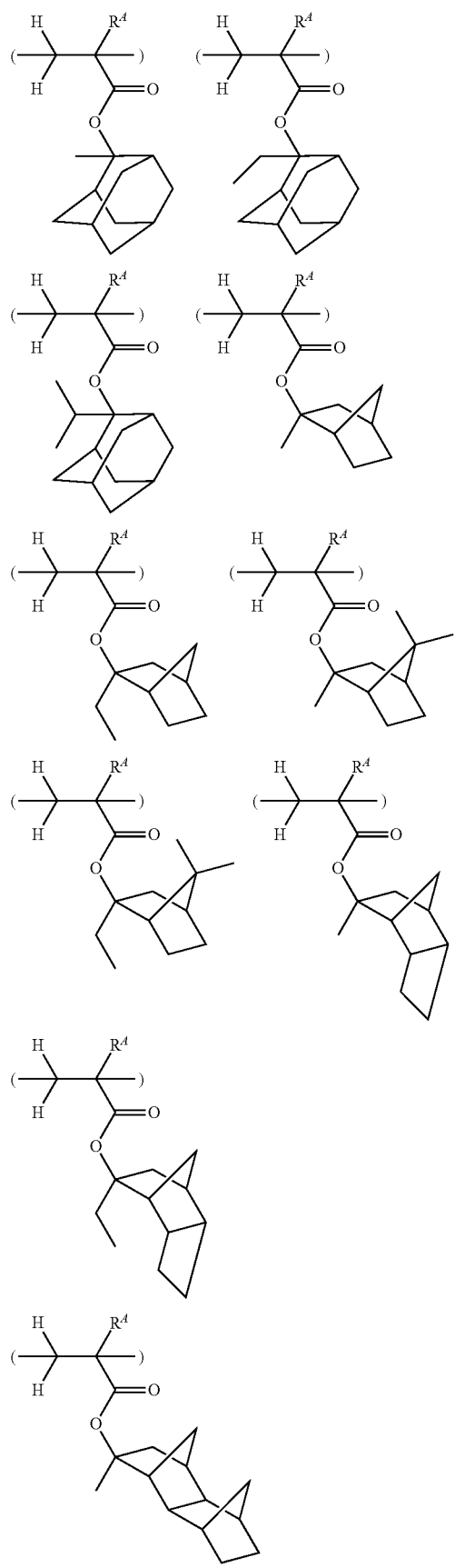
-continued
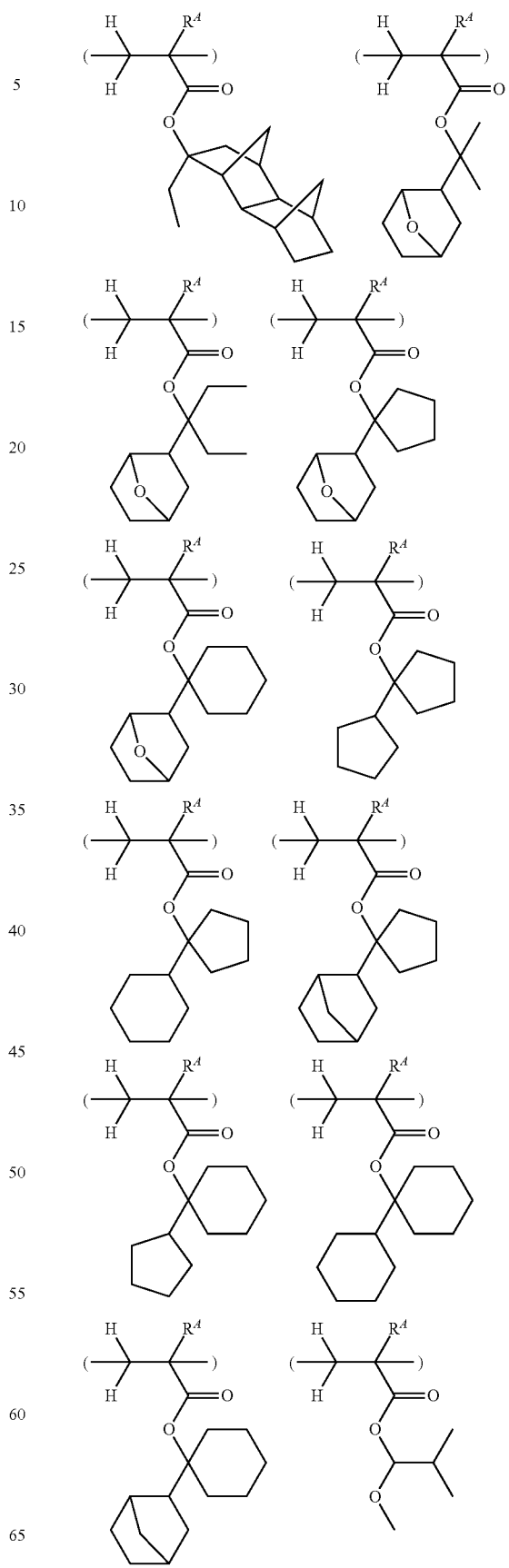

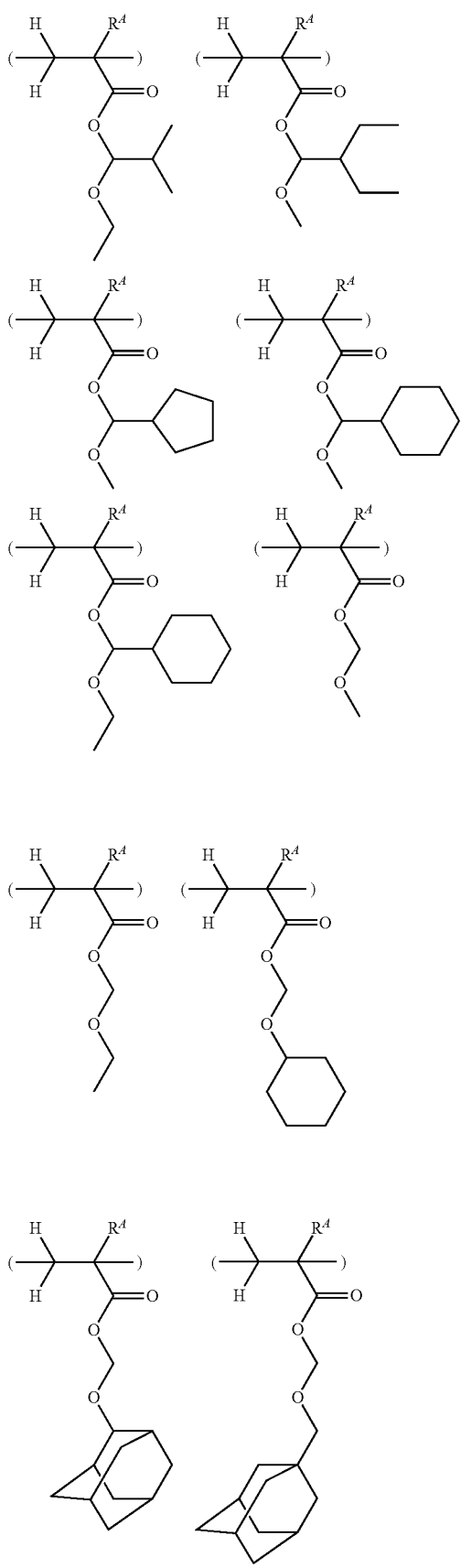
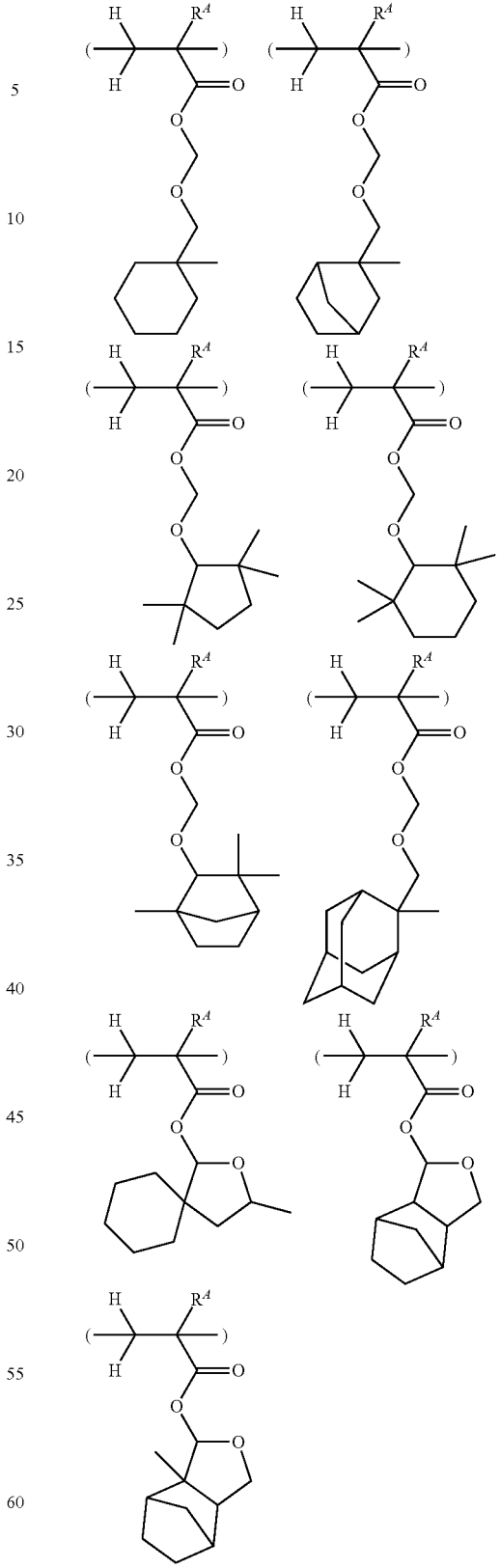
While the foregoing examples correspond to those units wherein $Z^A$ is a single bond, $Z^A$ which is other than a single bond may be combined with similar acid labile groups.

Examples of units wherein $Z^A$ is other than a single bond are substantially the same as illustrated above.
Illustrative, non-limiting examples of the recurring units having formula (b) are shown below. Herein $R^A$ is as defined above.
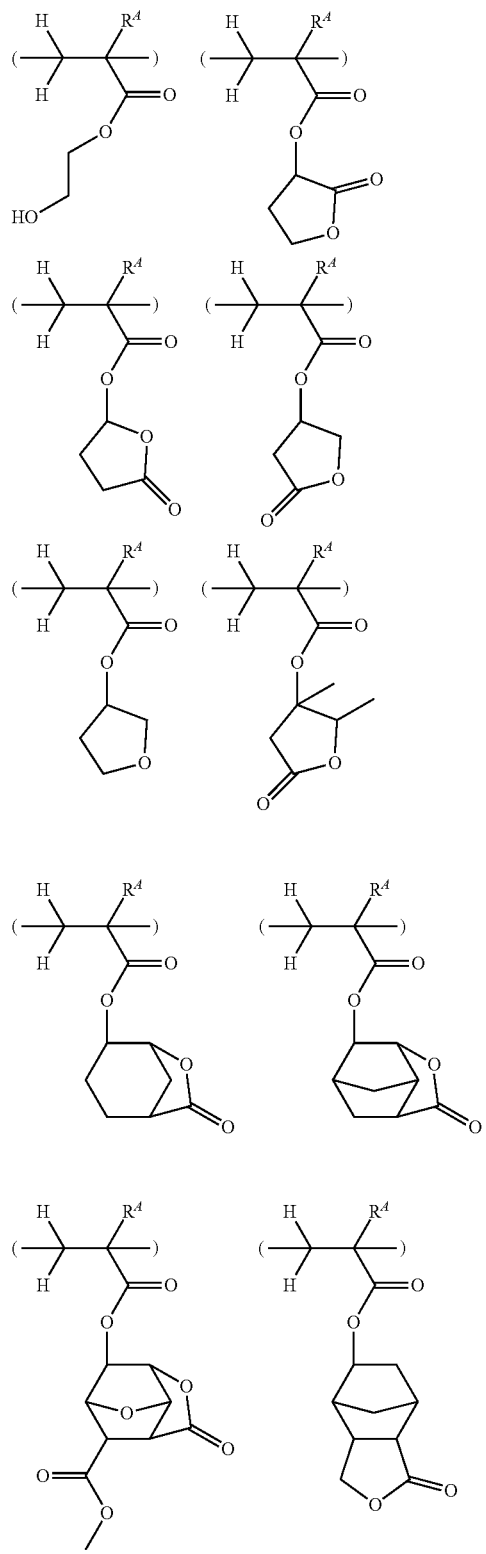
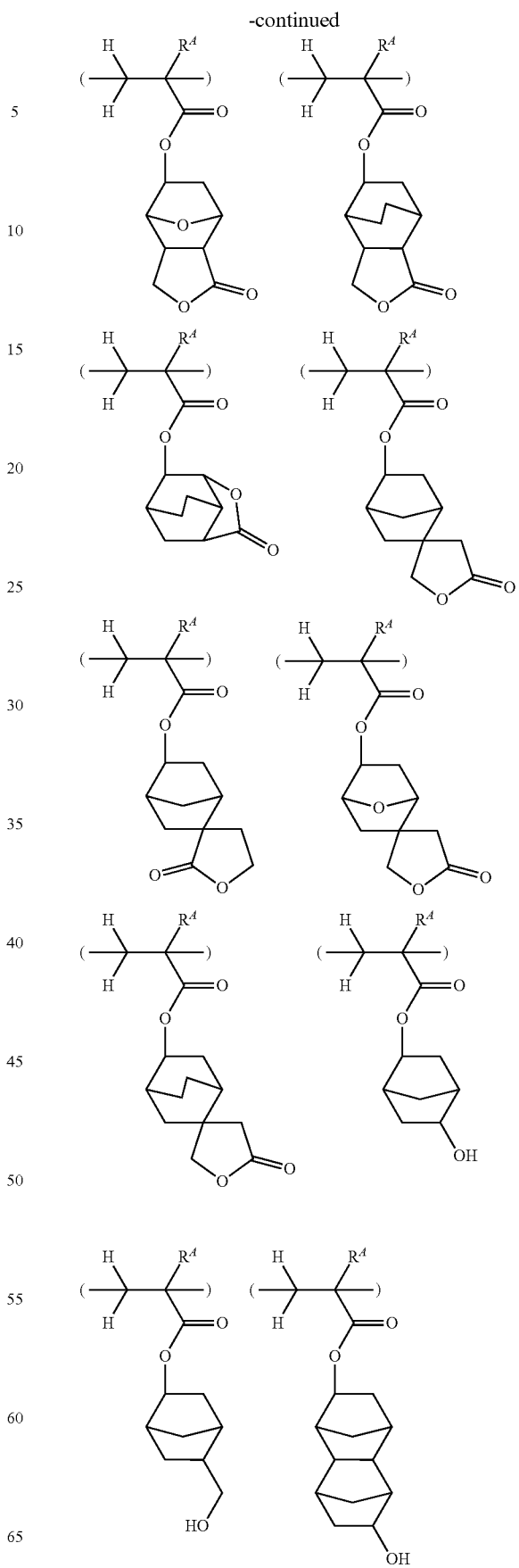

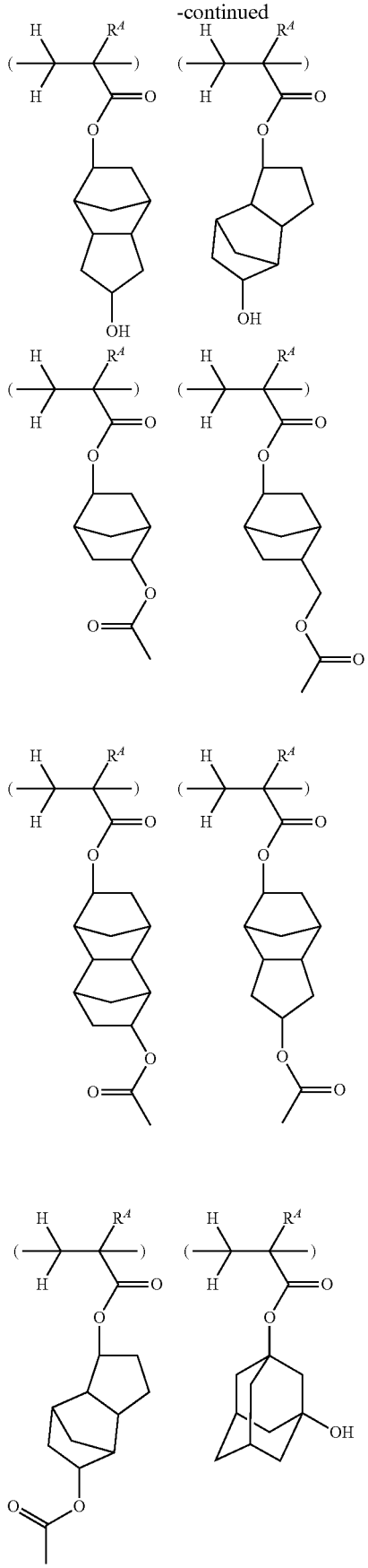
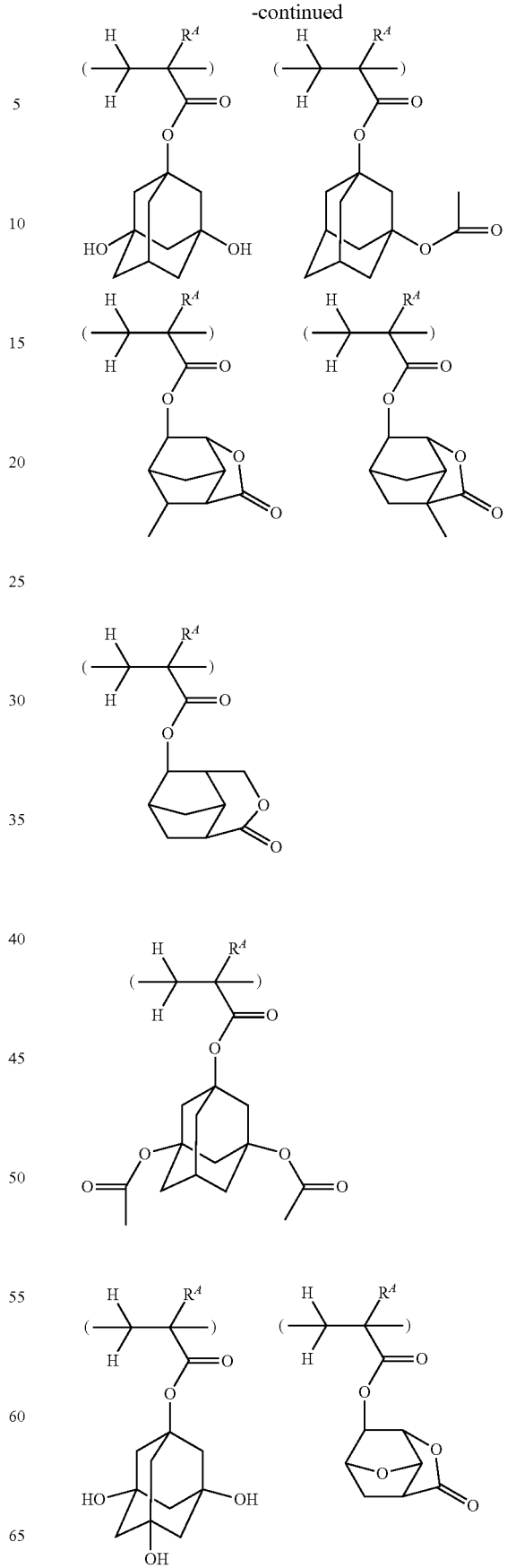

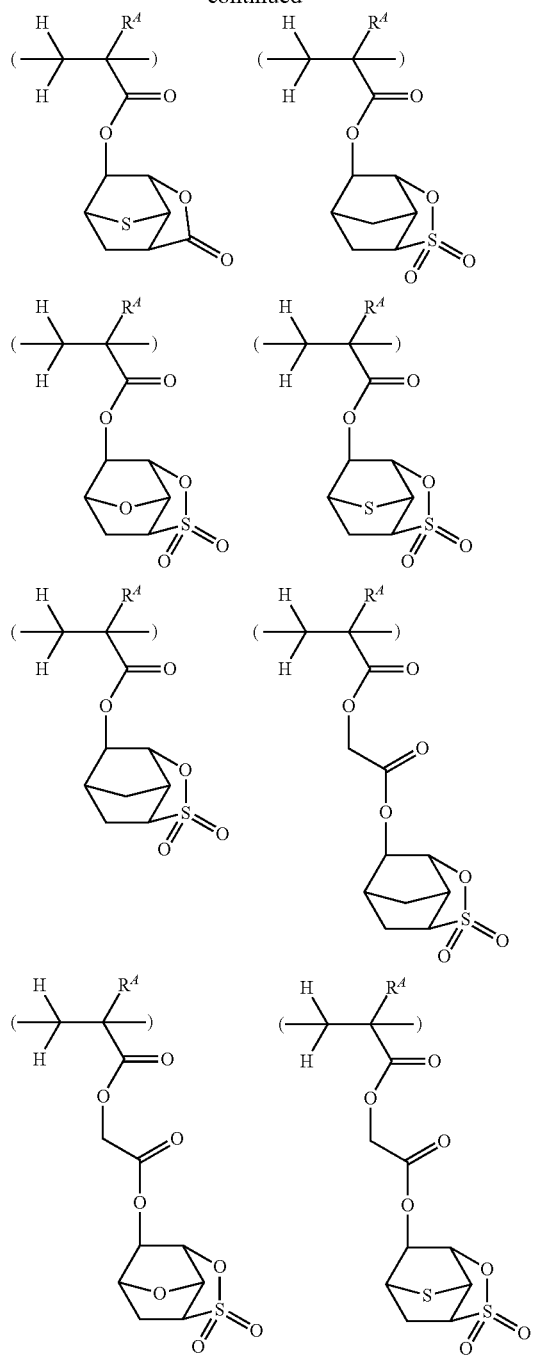
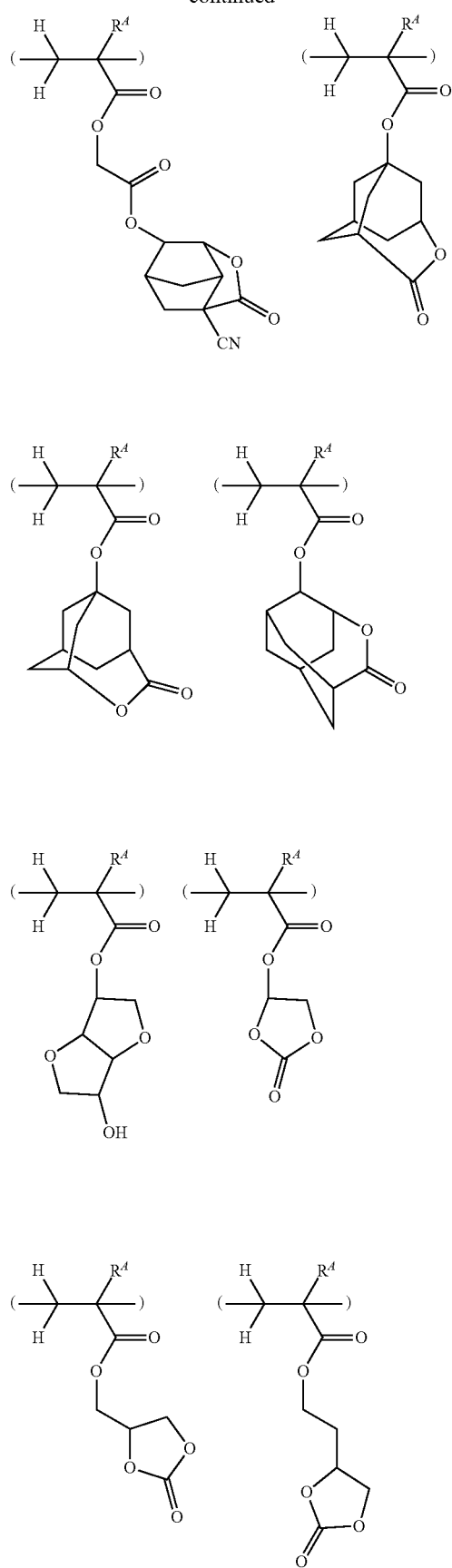

-continued
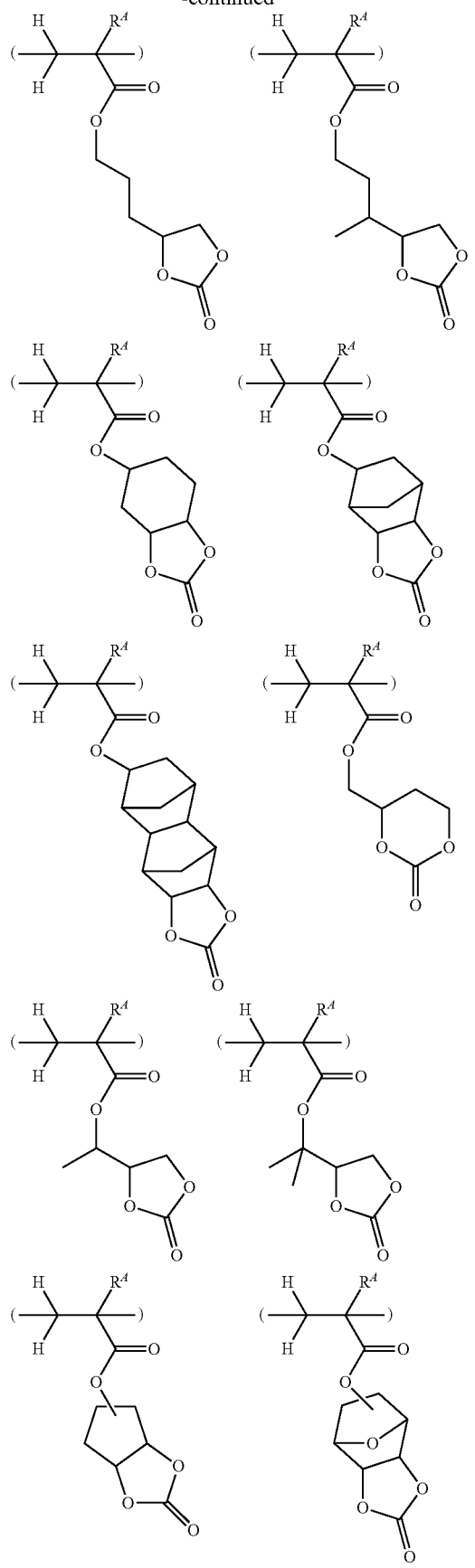
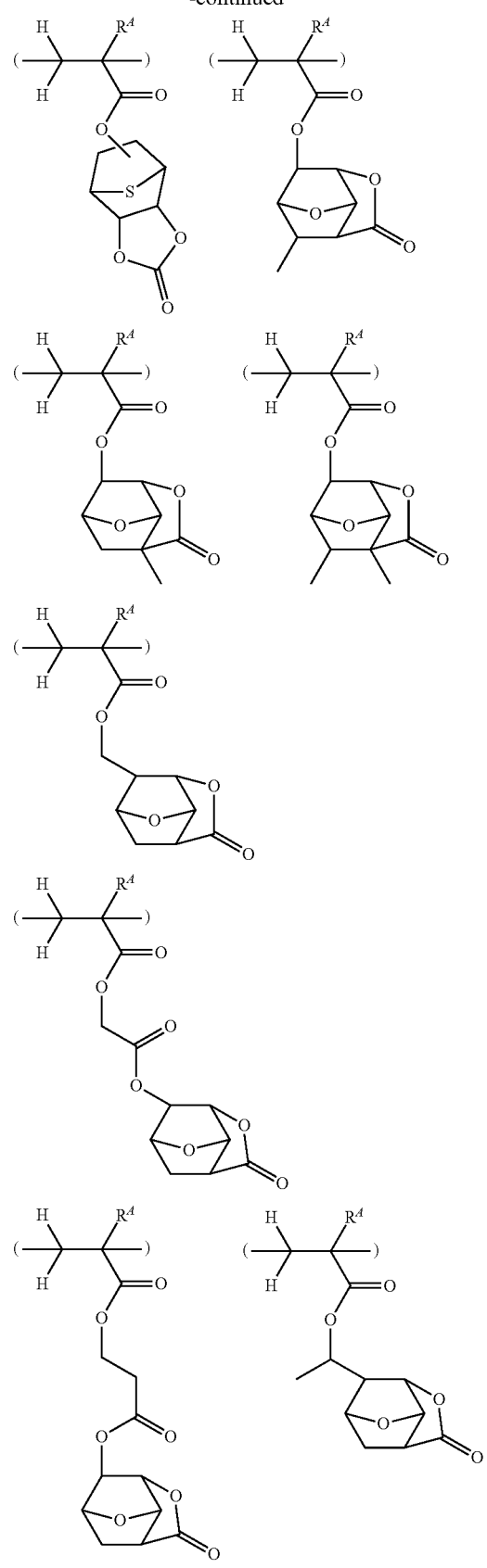

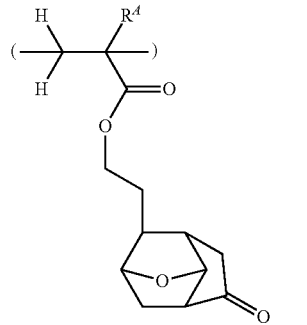
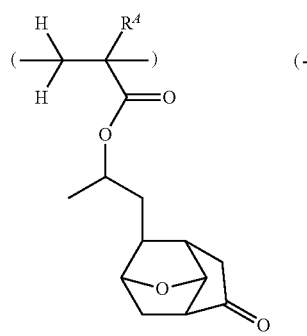
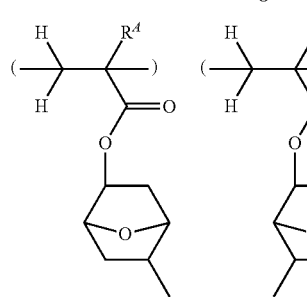
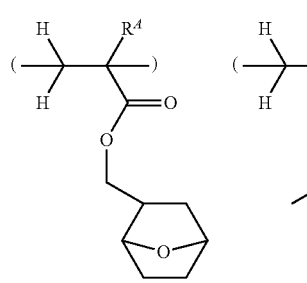
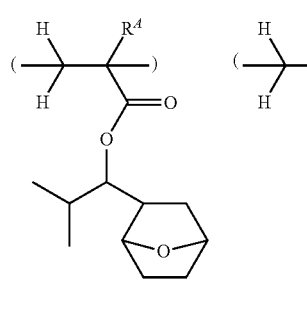
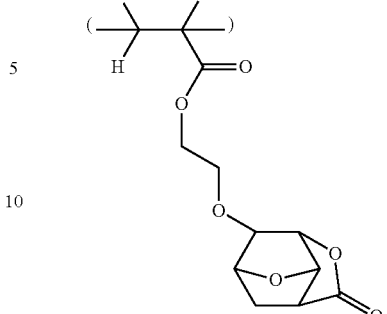
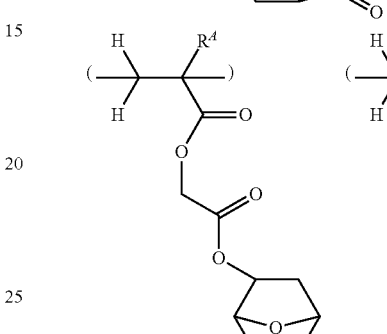
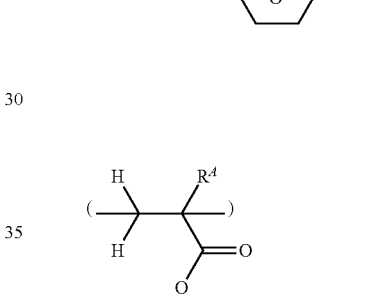
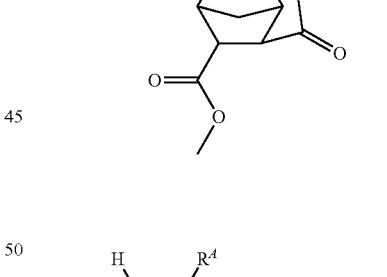
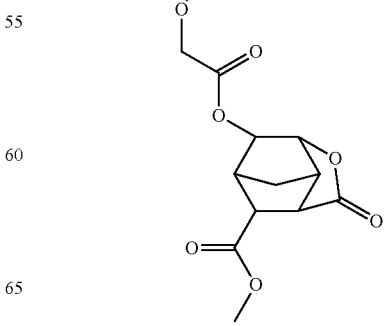

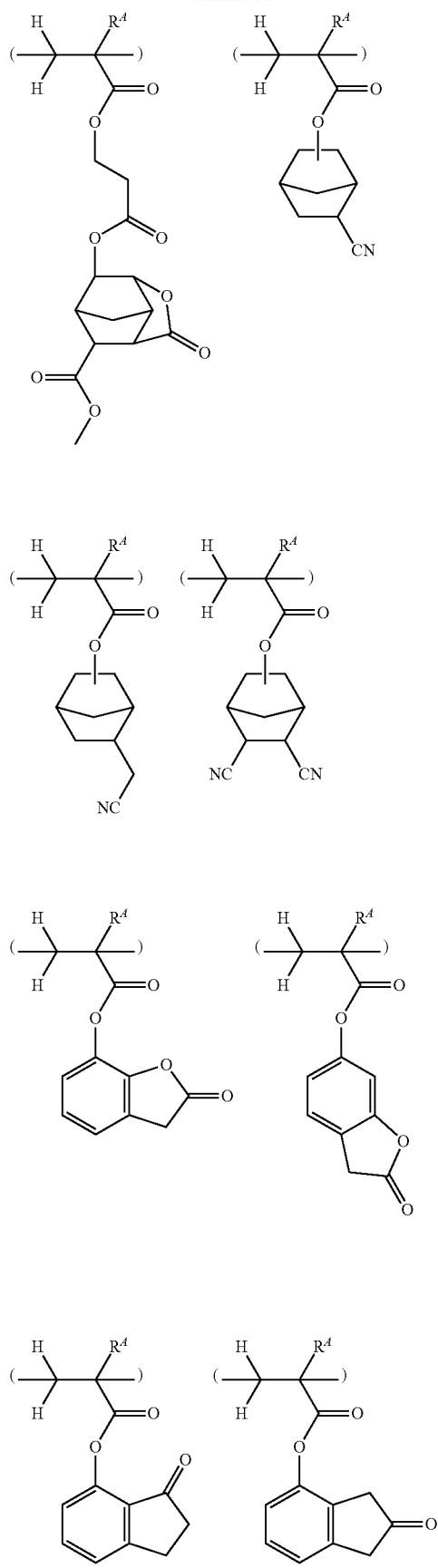
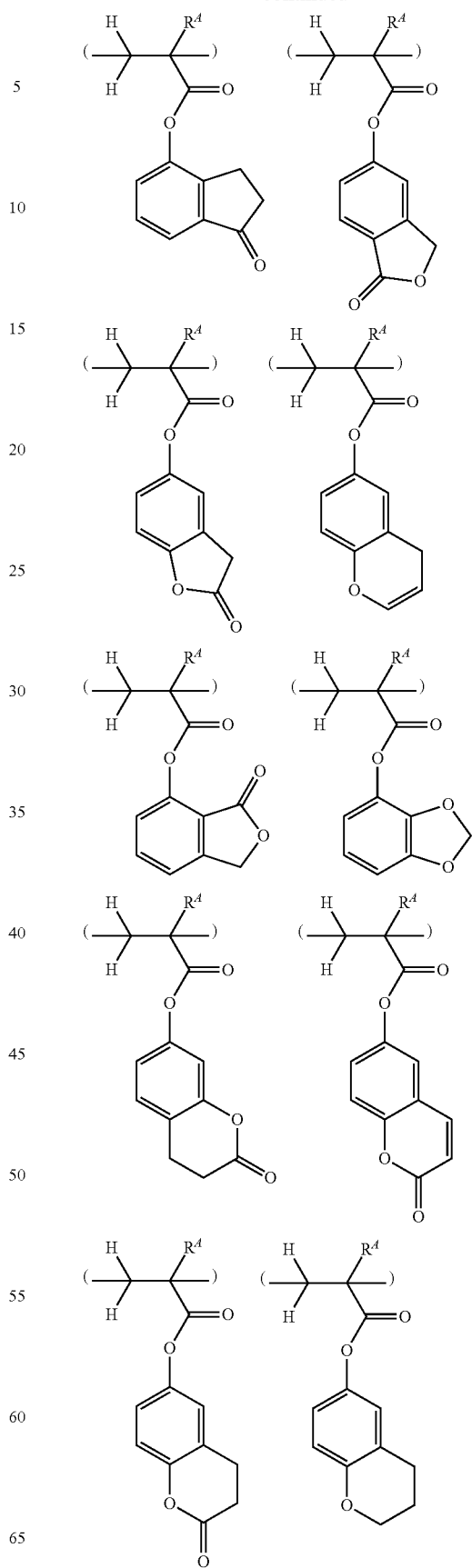

-continued
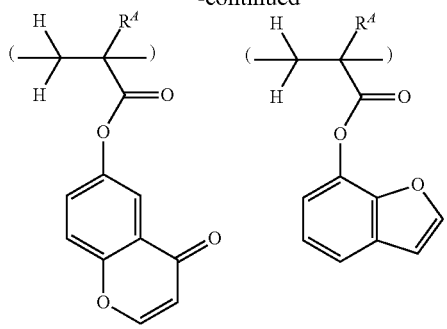
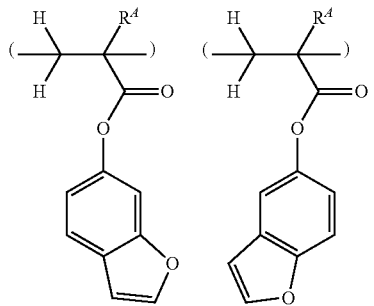
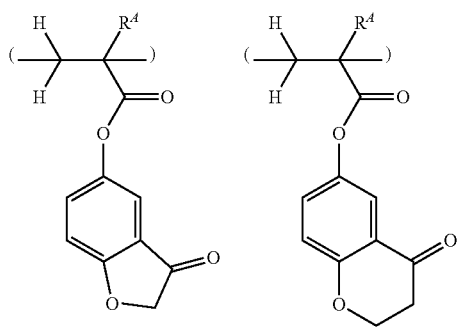
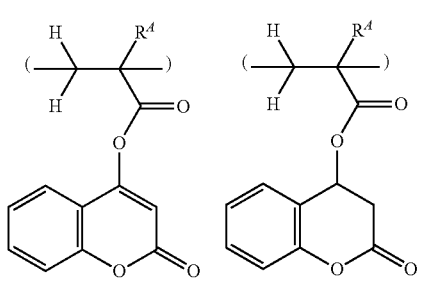
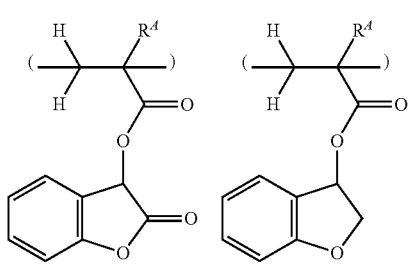
-continued
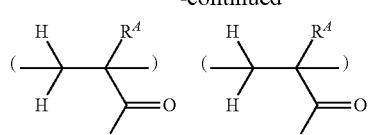
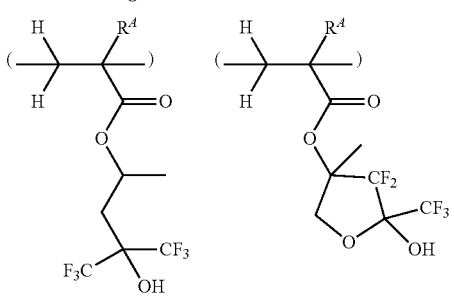
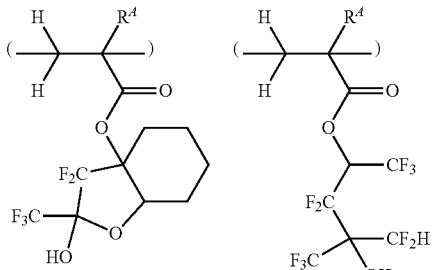
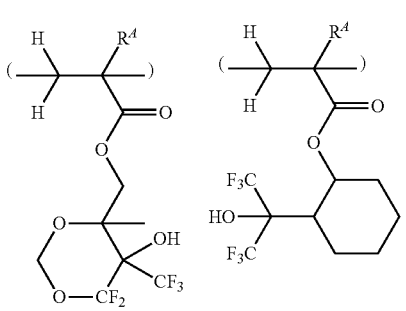
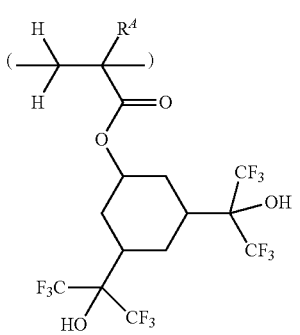

-continued
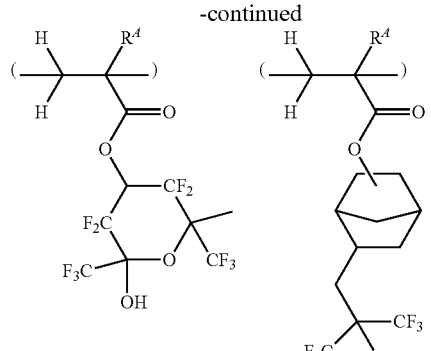
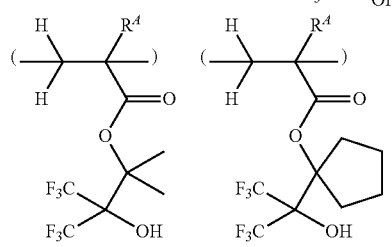
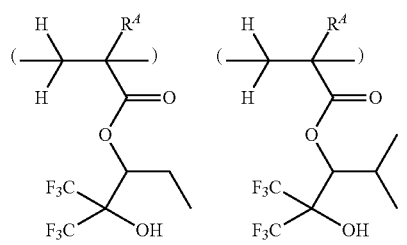
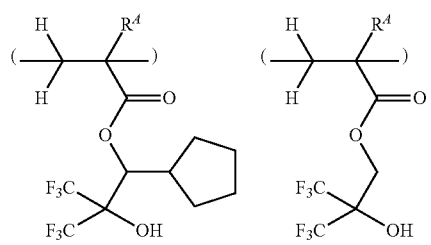
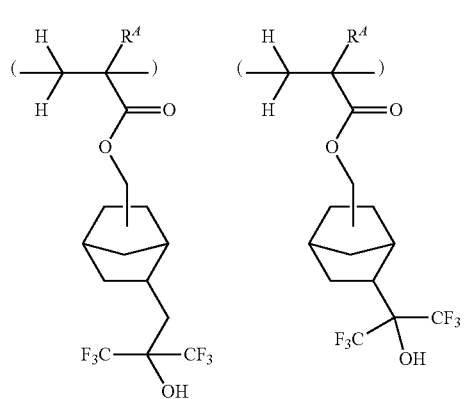
-continued
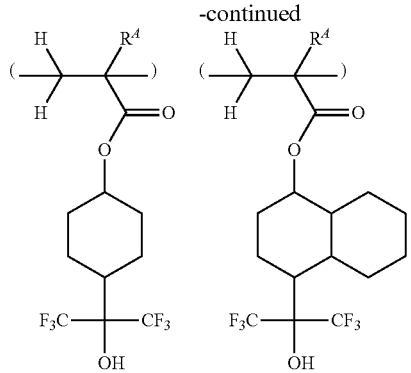
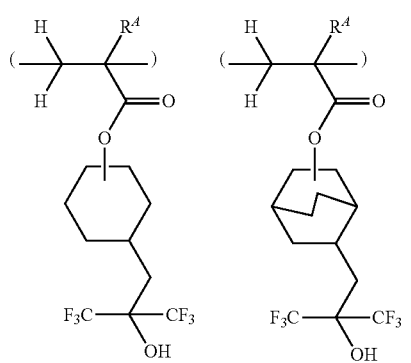
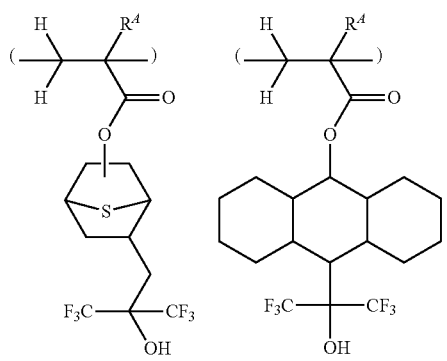
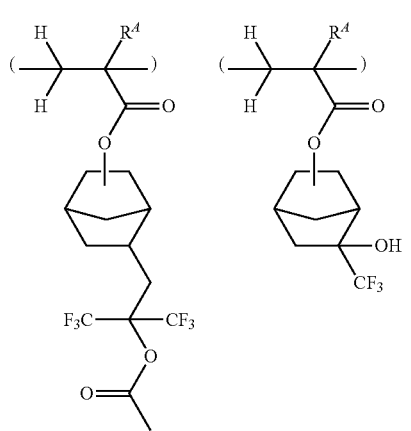

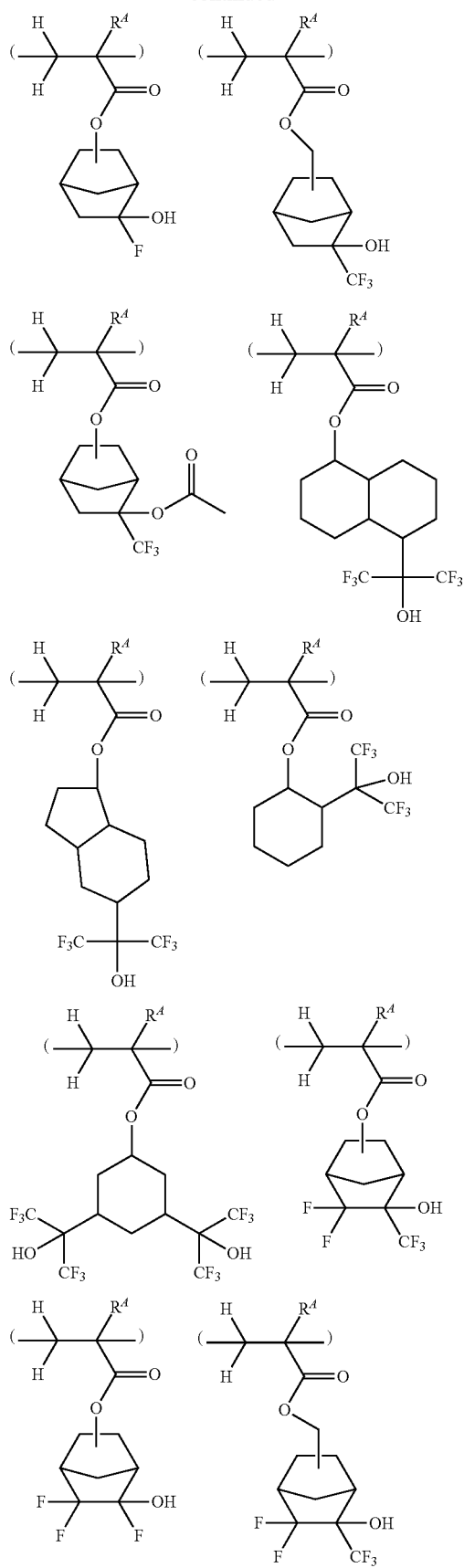
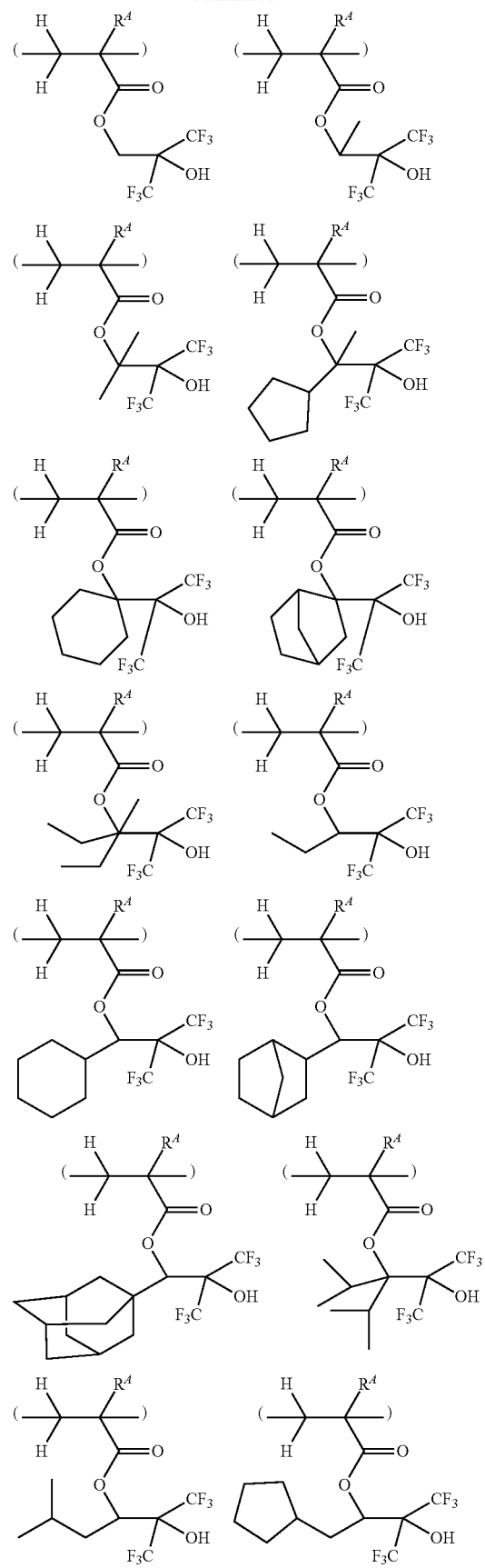

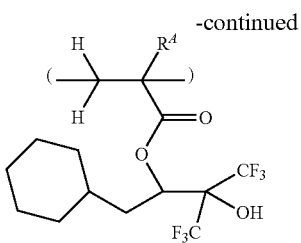

Of the recurring units having formula (b), those units having a lactone ring as the polar group are most preferred.

In addition to the recurring units having formulae (a) and (b), the polymer may further comprise recurring units having the formula (c1) or (c2).

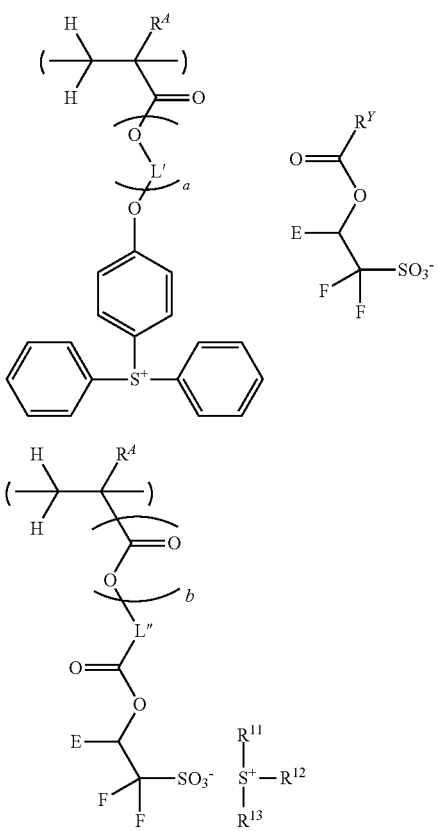

In formulae (c1) and (c2), $R^A$ is as defined and exemplified above. $R^{11}$, $R^{12}$ and $R^{13}$ are each independently a $C_1$-$C_{20}$ straight, branched or cyclic monovalent hydrocarbon group which may contain a heteroatom. L' is $C_2$-$C_5$ alkylene. $R^Y$ is a $C_1$-$C_{20}$ straight, branched or cyclic monovalent hydrocarbon group which may contain a heteroatom. B is hydrogen or trifluoromethyl. L" is a single bond or a $C_1$-$C_{20}$ straight, branched or cyclic divalent hydrocarbon group which may contain a heteroatom. The subscript a is 0 or 1, b is 0 or 1, with the proviso that b is 0 when L" is a single bond.

Exemplary of L' are ethylene, propylene and butylene. B is preferably trifluoromethyl. Examples of the monovalent hydrocarbon groups represented by $R^Y$, $R^{11}$, $R^{12}$ and $R^{13}$ are the same as will be exemplified for $R^{101}$, $R^{102}$ and $R^{103}$ in formula (5) below. Examples of the divalent hydrocarbon group L" include linear alkane diyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; saturated cyclic hydrocarbon groups such as cyclopentanediyl, cyclohexanediyl, norbornanediyl, and adamantanediyl; and unsaturated cyclic hydrocarbon groups such as phenylene and naphthylene. Also included are the foregoing groups in which at least one hydrogen atom is replaced by an alkyl radical such as methyl, ethyl, propyl, n-butyl or t-butyl, or in which at least one hydrogen atom is replaced by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl radical, cyano radical, carbonyl radical, ether bond, ester bond, sulfonic acid ester bond, carbonate bond, carbamate bond, lactone ring, sultone ring, carboxylic acid anhydride or haloalkyl radical.

Exemplary structures of the anion moiety in formula (c1) include those described in JP-A 2010-113209 and JP-A 2007-145797. Exemplary structures of the unit having formula (c2) wherein E is hydrogen include those described in JP-A 2010-116550, and exemplary structures of the unit having formula (c2) wherein E is trifluoromethyl include those described in JP-A 2010-077404.

The polymer may have further copolymerized therein recurring units of the structure having a hydroxyl group protected with an acid labile group. The recurring unit of the structure having a hydroxyl group protected with an acid labile group is not particularly limited as long as it has one or more protected hydroxyl-bearing structure such that the protective group may be decomposed to generate a hydroxyl group under the action of acid. Inter alia, recurring units having the formula (d1) are preferred.

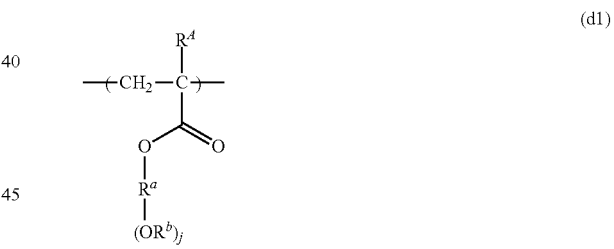

In formula (d1), $R^A$ is as defined above, $R^a$ is a $C_1$-$C_{30}$ straight, branched or cyclic (j+1)-valent hydrocarbon group which may contain a heteroatom, $R^b$ is an acid labile group, and j is an integer of 1 to 4.

Examples of the recurring unit of formula (d1) are shown below, but not limited thereto. Herein $R^A$ and $R^b$ are as defined above.

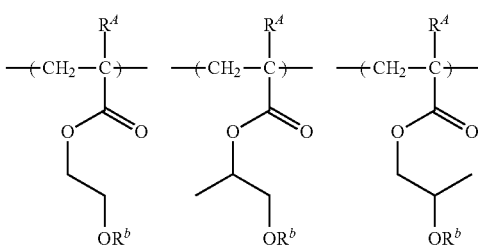

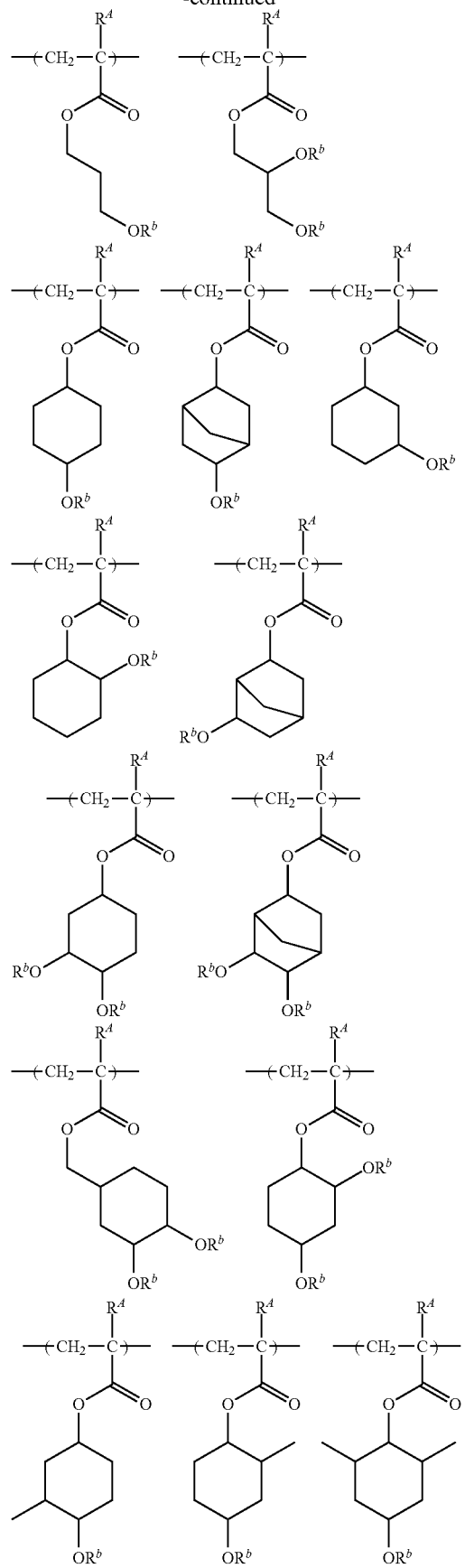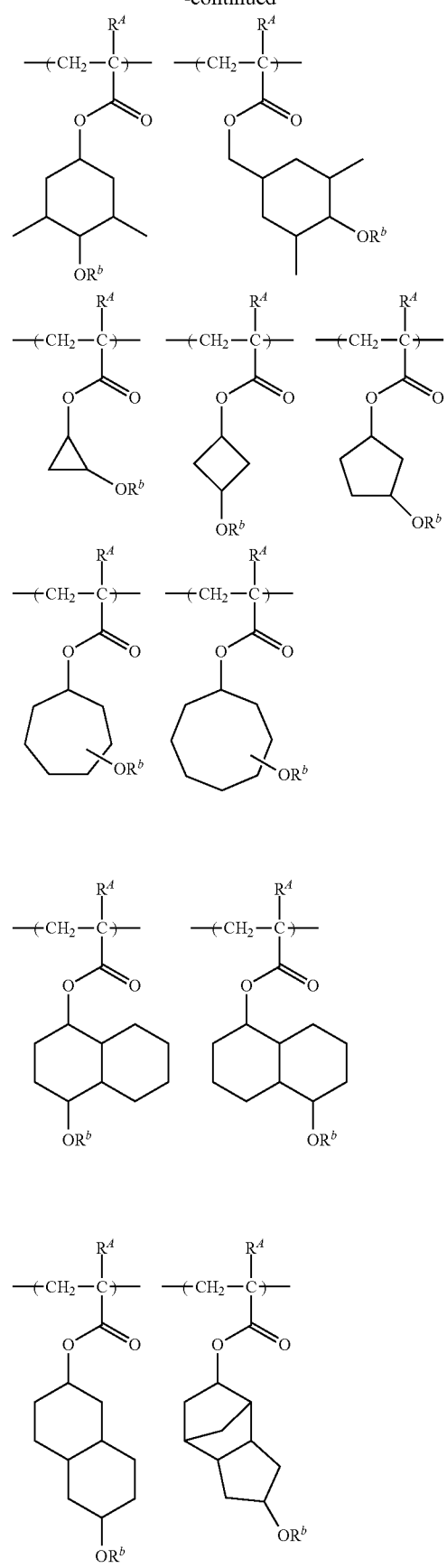

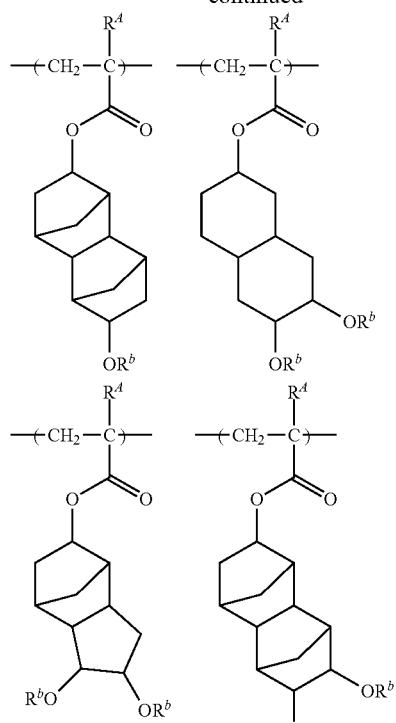
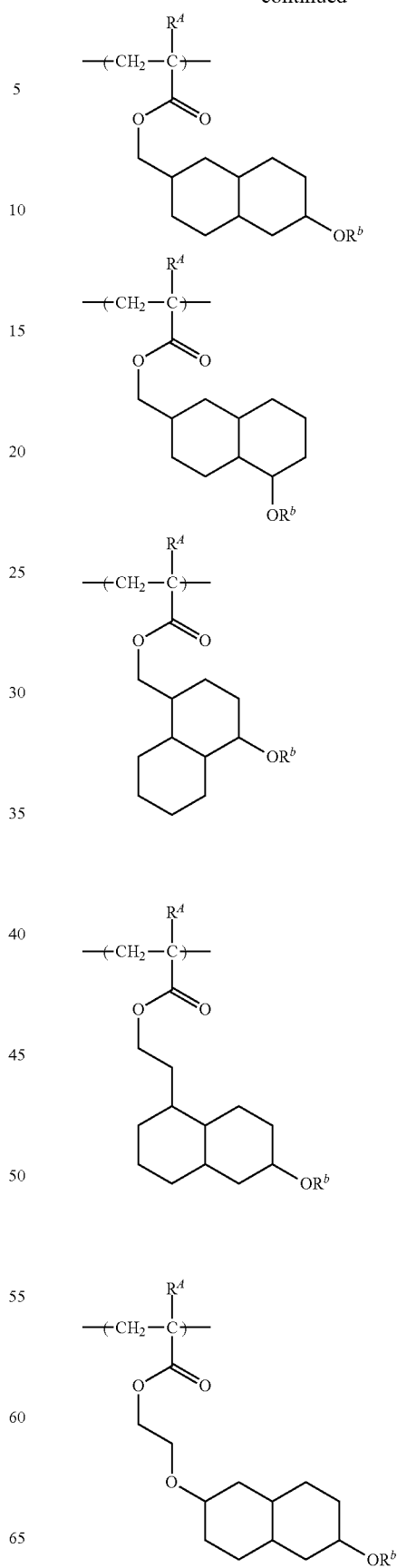

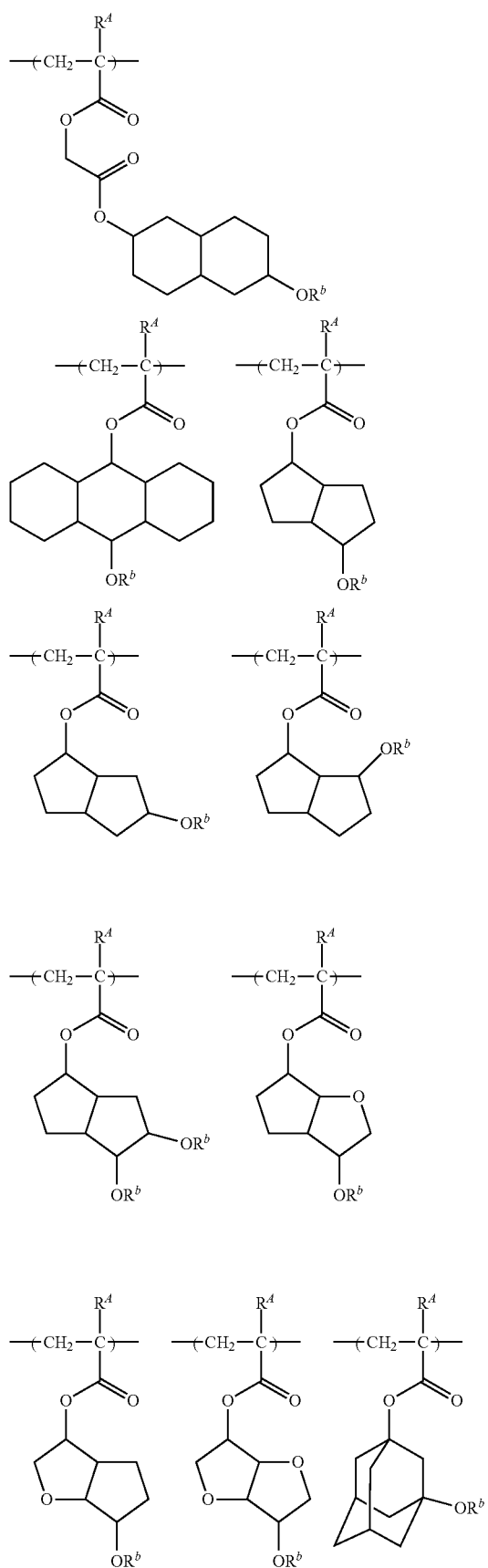
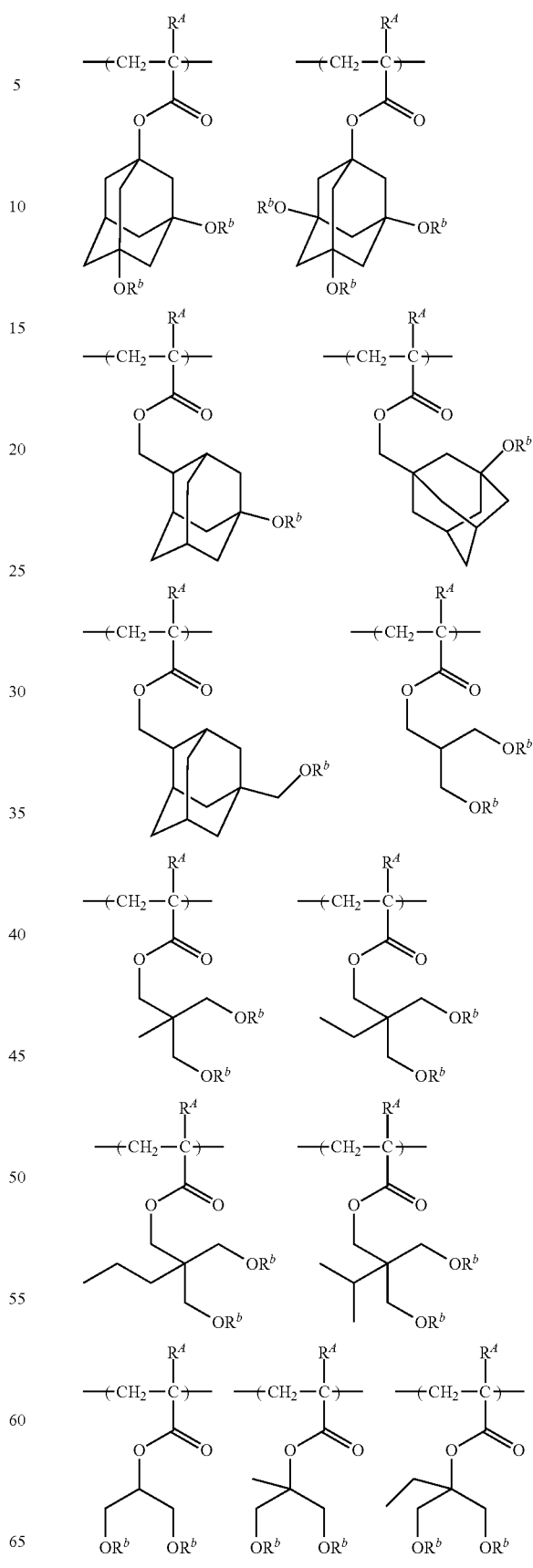

-continued

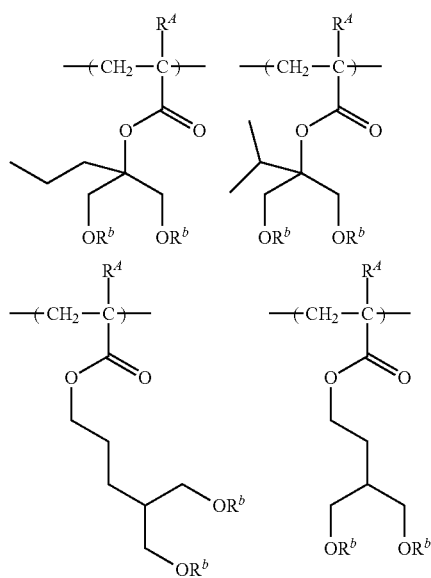
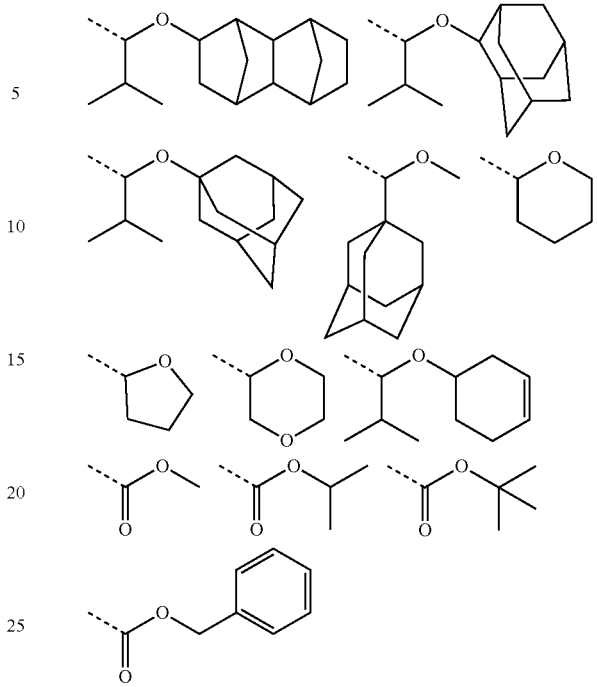

The structure of the acid labile group $R^b$ in formula (d1) is not particularly limited as long as it is deprotected to generate a hydroxyl group under the action of acid. Typical acid labile groups are groups of acetal or ketal structure and alkoxycarbonyl groups, with their examples being shown below.

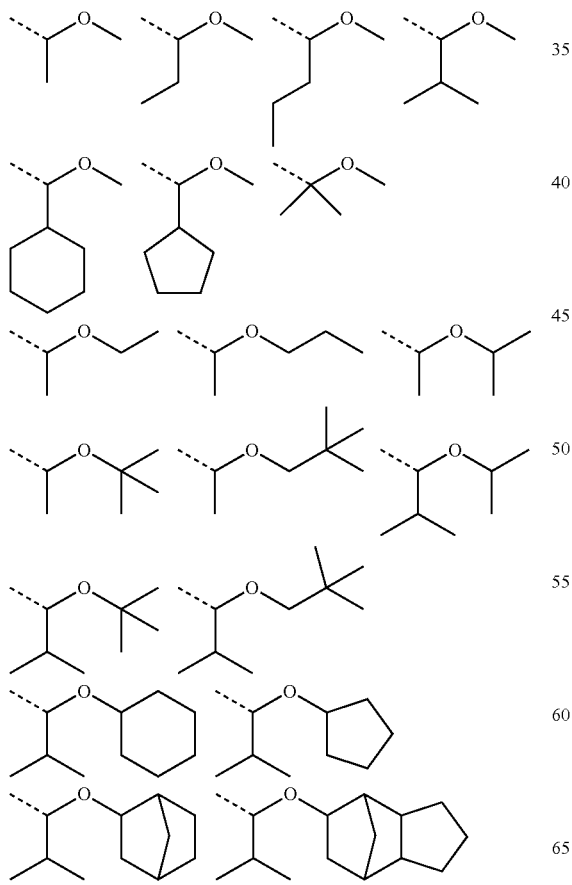

Of the acid labile group $R^b$, preferred are alkoxymethyl group having the formula (d2):

$$\text{-----}\underset{H_2}{C}\text{---}O\text{---}R^c \quad (d2)$$

wherein $R^c$ is a $C_1$-$C_{15}$ straight, branched or cyclic monovalent hydrocarbon group.

Examples of the acid labile group of formula (d2) are shown below, but not limited thereto.

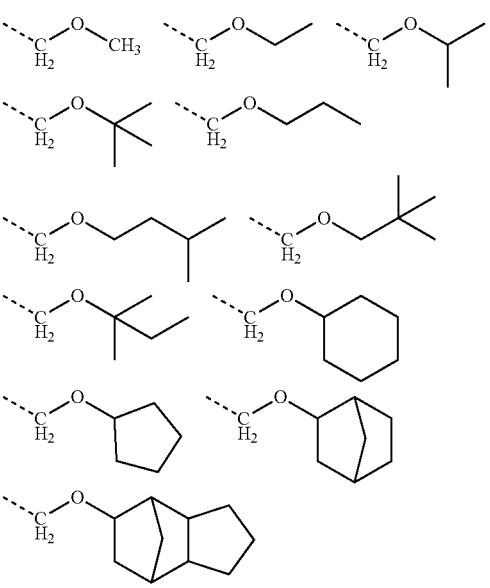

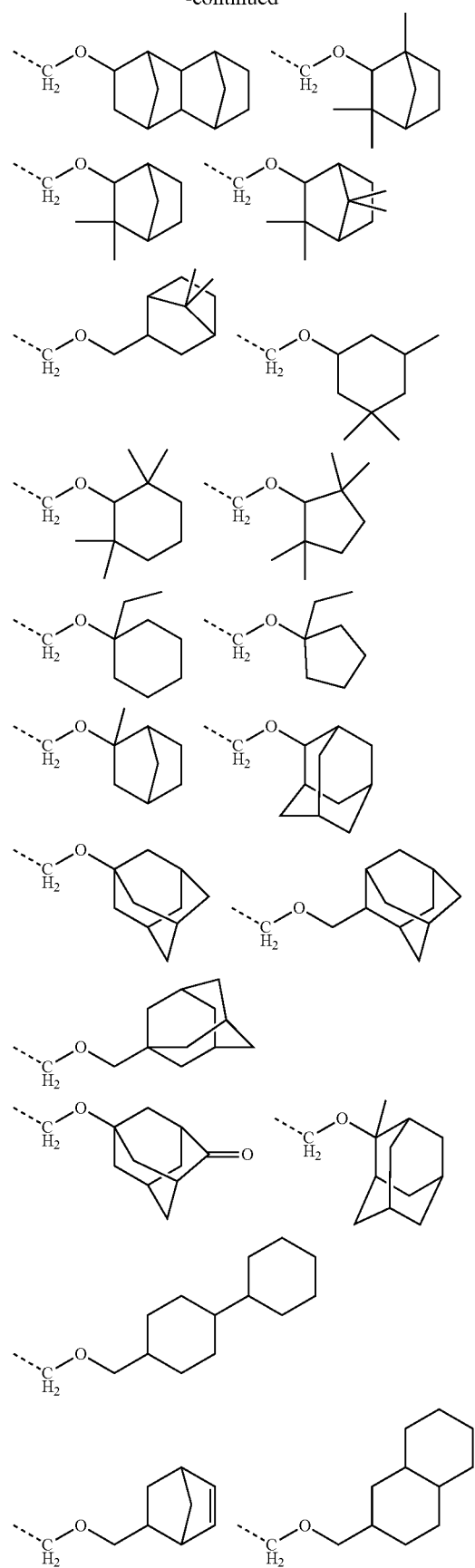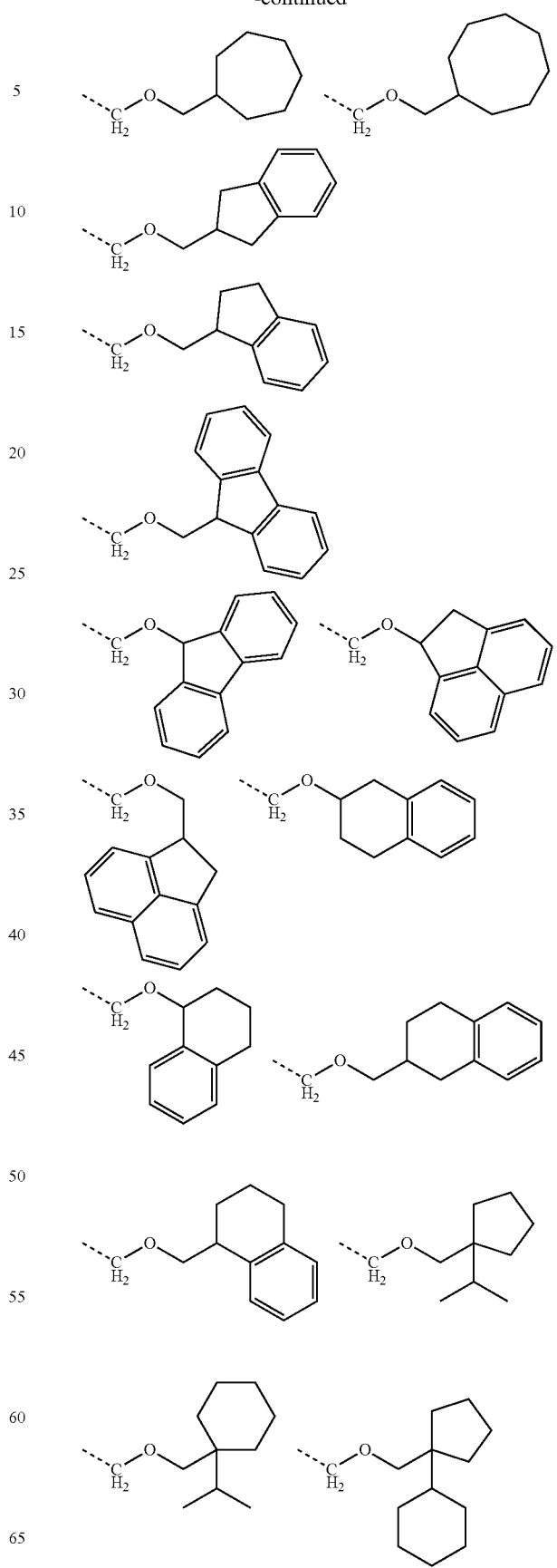

-continued

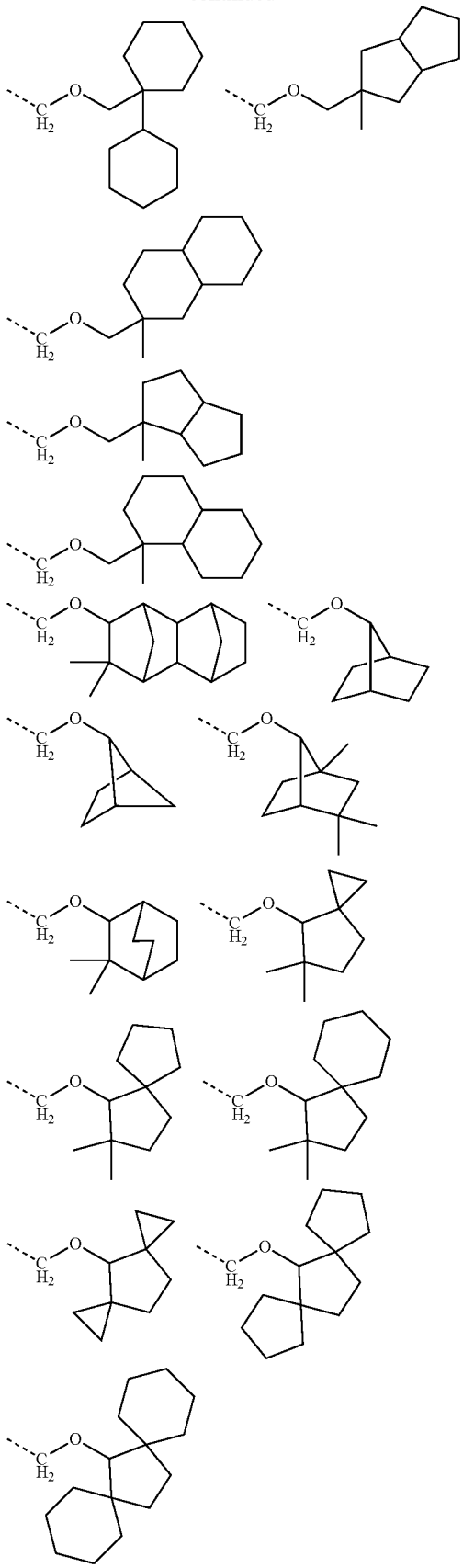

In addition to the foregoing units, the polymer may further comprise recurring units derived from other monomers, for example, substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo[6.2.1.1$^{3,6}$.0$^{2,2}$]dodecene derivatives, unsaturated acid anhydrides such as itaconic anhydride, and other monomers.

The polymer has a weight average molecular weight (Mw) of preferably 1,000 to 500,000, more preferably 3,000 to 100,000, as measured by gel permeation chromatography (GPC) versus polystyrene standards using tetrahydrofuran (THF) solvent. As long as Mw is within the range, sufficient etching resistance is obtainable, and any drop of resolution due to a failure to establish a dissolution rate difference before and after exposure is avoided.

If a polymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the polymer should preferably have a narrow dispersity (Mw/Mn) of 1.0 to 2.0 in order to formulate a resist composition suited for fine size pattern formation.

The method of synthesizing the polymer is, for example, by dissolving one or more unsaturated bond-bearing monomers in an organic solvent, adding a radical initiator, and effecting heat polymerization. Examples of the organic solvent which can be used for polymerization include toluene, benzene, tetrahydrofuran, diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the reaction temperature is in a range of 50 to 80° C. and the reaction time is 2 to 100 hours, more preferably 5 to 20 hours. The acid labile group that has been incorporated in the monomer may be kept as such, or polymerization may be followed by protection or partial protection.

While the polymer comprises recurring units derived from monomers, the molar fractions of respective units preferably fall in the following range (mol %), but are not limited thereto:

(I) 1 to 60 mol %, more preferably 5 to 50 mol %, even more preferably 10 to 50 mol % of recurring units of at least one type having formula (a), (II) 40 to 99 mol %, more preferably 50 to 95 mol %, even more preferably 50 to 90 mol % of recurring units of at least one type having formula (b), and optionally, (III) 0 to 30 mol %, more preferably 0 to 20 mol %, and even more preferably 0 to 10 mol % of recurring units of at least one type having formula (c1), (c2) or (c3), and optionally, (IV) 0 to 80 mol %, more preferably 0 to 70 mol %, and even more preferably 0 to 50 mol % of recurring units of at least one type derived from another monomer(s).

It is acceptable to use a blend of two or more polymers which differ in compositional ratio, molecular weight or dispersity as the base resin (B).

(C) Organic Solvent

The resist composition may comprise (C) an organic solvent. The organic solvent used herein is not particularly limited as long as the above and other components are soluble therein. Examples of the organic solvent are described in JP-A 2008-111103, paragraphs [0144] to [0145] (U.S. Pat. No. 7,537,880). Specifically, exemplary solvents include ketones such as cyclohexanone and methyl-2-n-pentyl ketone; alcohols such as 3-methoxybutanol, 3-methyl-3-methoxybutanol, 1-methoxy-2-propanol, 1-ethoxy-2-propanol, and diacetone alcohol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether, esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, and mixtures thereof. Where an acid labile group of acetal form is used, a high-boiling alcohol solvent such as diethylene glycol, propylene glycol, glycerol, 1,4-butanediol or 1,3-butane-diol may be added for accelerating deprotection reaction of acetal. Of the above organic solvents, it is recommended to use 1-ethoxy-2-propanol, PGMEA, cyclohexanone, γ-butyrolactone, and mixtures thereof because the PAG is most soluble therein.

An appropriate amount of the organic solvent (C) used is 200 to 5,000 parts, more preferably 400 to 3,000 parts by weight per 100 parts by weight of the base resin (B).

(D) Second PAG

The resist composition may further comprise (D) a photoacid generator other than the sulfonium compound defined herein, which is referred to as second photoacid generator. The second PAG may be any compound capable of generating an acid upon exposure to high-energy radiation such as UV, DUV, EB, EUV, x-ray, excimer laser, γ-ray or synchrotron radiation. Suitable PAGs include sulfonium salts, iodonium salts, sulfonyldiazomethane, N-sulfonyloxydicarboxyimide, O-arylsulfonyloxime, and O-alkylsulfonyloxime compounds. These PAGs may be used alone or in admixture of two or more. Suitable PAGs are described, for example, in JP-A 2007-145797, paragraphs [0102]-[0113].

As the second PAG, those having the formula (5) are preferred.

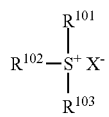
(5)

In formula (5), $R^{101}$, $R^{102}$ and $R^{103}$ are each independently a $C_1$-$C_{20}$ straight, branched or cyclic monovalent hydrocarbon group which may contain a heteroatom. Suitable monovalent hydrocarbon groups include alkyl groups such as methyl, ethyl, propyl, isopropyl, n-butyl, s-butyl, t-butyl, t-pentyl, n-pentyl, n-hexyl, n-octyl, cyclopentyl, cyclohexyl, 2-ethylhexyl, cyclopentylmethyl, cyclopentylethyl, cyclohexylmethyl, cyclohexylethyl, norbornyl, oxanorbornyl, tricyclo[5.2.1.0$^{2,6}$]decanyl, and adamantyl; and aryl groups such as phenyl and naphthyl. Also included are the foregoing groups in which at least one hydrogen atom is substituted by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl radical, cyano radical, carbonyl radical, ether bond, ester bond, sulfonic acid ester bond, carbonate bond, lactone ring, sultone ring, carboxylic acid anhydride or haloalkyl radical. Preferably, $R^{101}$, $R^{102}$ and $R^{103}$ are optionally substituted aryl groups.

Any two of $R^{101}$, $R^{102}$ and $R^{103}$ may bond together to form a ring with the sulfur atom to which they are attached. Examples of the cation in this embodiment are shown below, but not limited thereto.

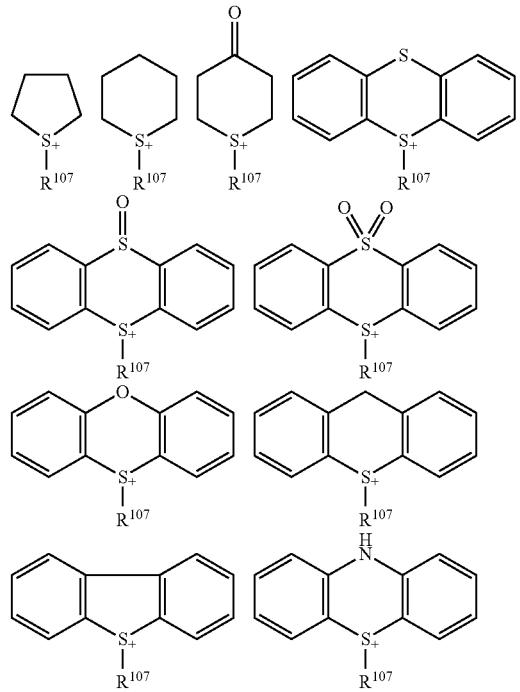

Herein $R^{107}$ is a $C_1$-$C_{20}$ straight, branched or cyclic monovalent hydrocarbon group which may contain a heteroatom, examples of which are as exemplified above for $R^{101}$ to $R^{103}$.

Exemplary structures of the sulfonium cation in formula (5) are shown below, but not limited thereto.

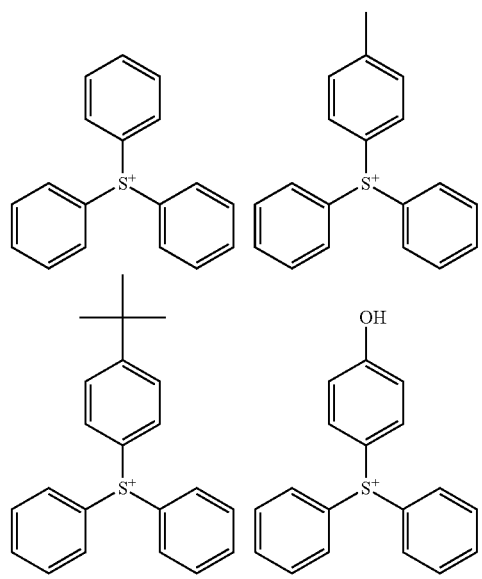

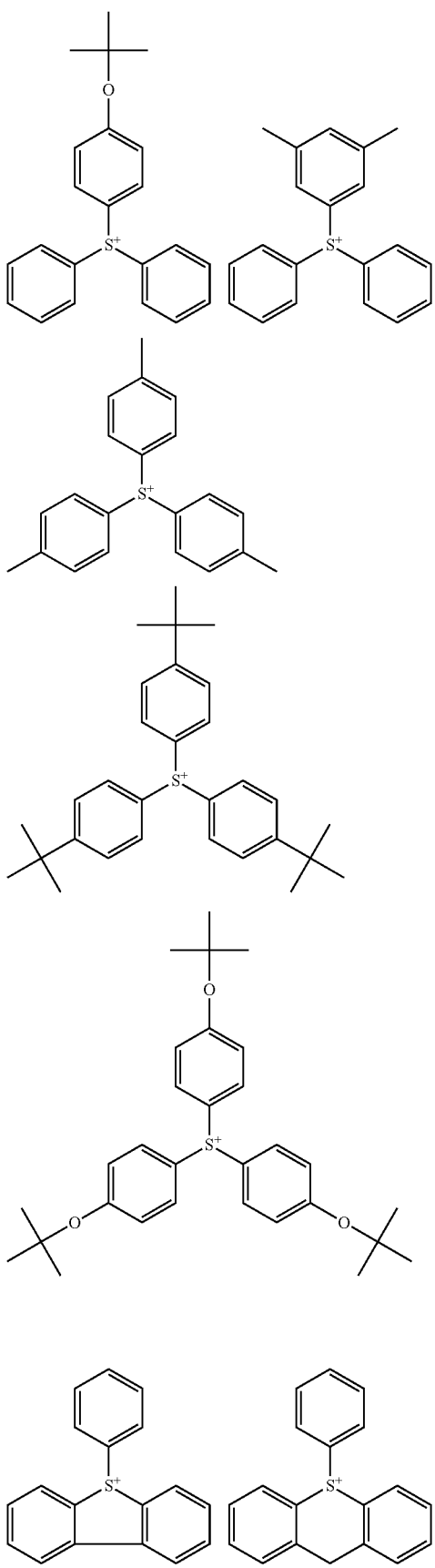

In formula (5), X⁻ is an anion selected from the formulae (5A) to (5D).

$$R^{fa}-CF_2-SO_3^- \quad (5A)$$

$$\begin{array}{c} R^{fb1}-CF_2-SO_2 \\ \phantom{R^{fb1}-CF_2-SO_2}\diagdown N^- \\ R^{fb2}-CF_2-SO_2\diagup \end{array} \quad (5B)$$

$$R^{fc1}-CF_2-SO_2-\underset{\underset{\underset{\underset{R^{fc3}}{\mid}}{CF_2}}{\underset{\mid}{SO_2}}}{\overset{\overset{\overset{\overset{R^{fc2}}{\mid}}{CF_2}}{\mid}}{\underset{\mid}{SO_2}}}{C^-} \quad (5C)$$

$$R^{fd}-\underset{\underset{O}{\|}}{C}-O-\underset{\underset{CF_3}{\mid}}{\overset{\overset{CF_3}{\mid}}{C}}-CH_2-SO_3^- \quad (5D)$$

In formula (5A), $R^{fa}$ is fluorine or a $C_1$-$C_{40}$ straight, branched or cyclic monovalent hydrocarbon group which may contain a heteroatom. Suitable structures include nonafluorobutane sulfonate, partially fluorinated sulfonates described in JP-A 2012-189977, paragraphs [0247]-[0251], partially fluorinated sulfonates described in JP-A 2013-

101271, paragraphs [0261]-[0265], and partially fluorinated sulfonates described in JP-A 2013-101271, paragraphs [0261]-[0265].

Of the anions of formula (5A), a structure having formula (5A') is preferred.

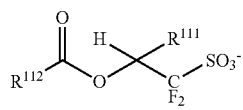
(5A')

In formula (5A'), $R^{111}$ is hydrogen or trifluoromethyl. $R^{112}$ is a $C_1$-$C_{30}$ straight, branched or cyclic monovalent hydrocarbon group which may contain a heteroatom. Suitable heteroatoms include oxygen, nitrogen, sulfur and halogen, with oxygen being preferred. Of the monovalent hydrocarbon groups, those of 6 to 30 carbon atoms are preferred because a high resolution is available in fine pattern formation. Suitable monovalent hydrocarbon groups include methyl, ethyl, propyl, isopropyl, butyl, isobutyl, s-butyl, t-butyl, pentyl, neopentyl, cyclopentyl, hexyl, cyclohexyl, 3-cyclohexenyl, heptyl, 2-ethylhexyl, nonyl, undecyl, tridecyl, pentadecyl, heptadecyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl, icosanyl, allyl, benzyl, diphenylmethyl, tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl.

With respect to the synthesis of the sulfonium salt having an anion of formula (5A'), reference is made to JP-A 2007-145797, JP-A 2008-106045, JP-A 2009-007327, and JP-A 2009-258695.

Examples of the sulfonium salt having an anion of formula (5A) are shown below, but not limited thereto.

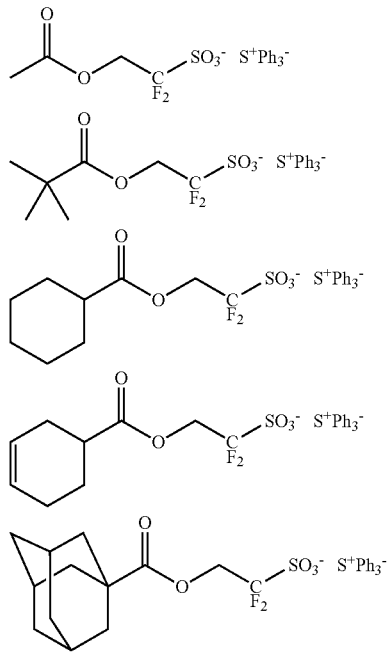

-continued

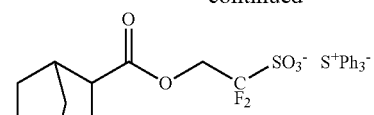

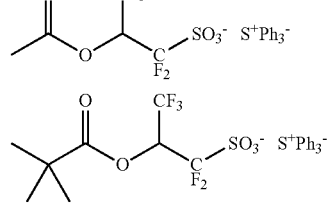

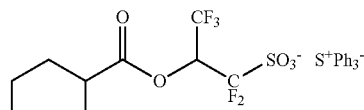

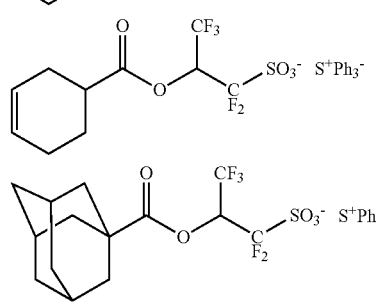

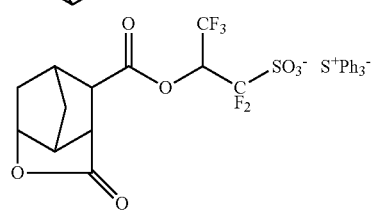

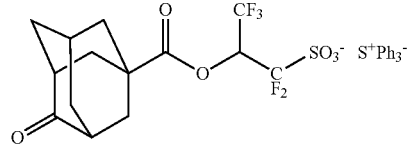

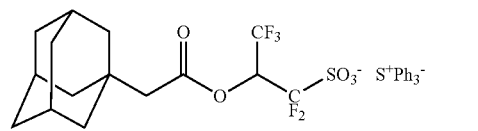

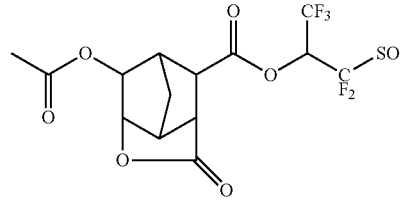

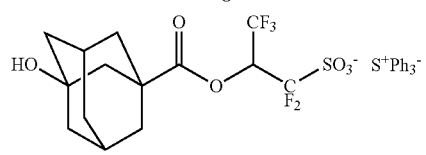

75
-continued
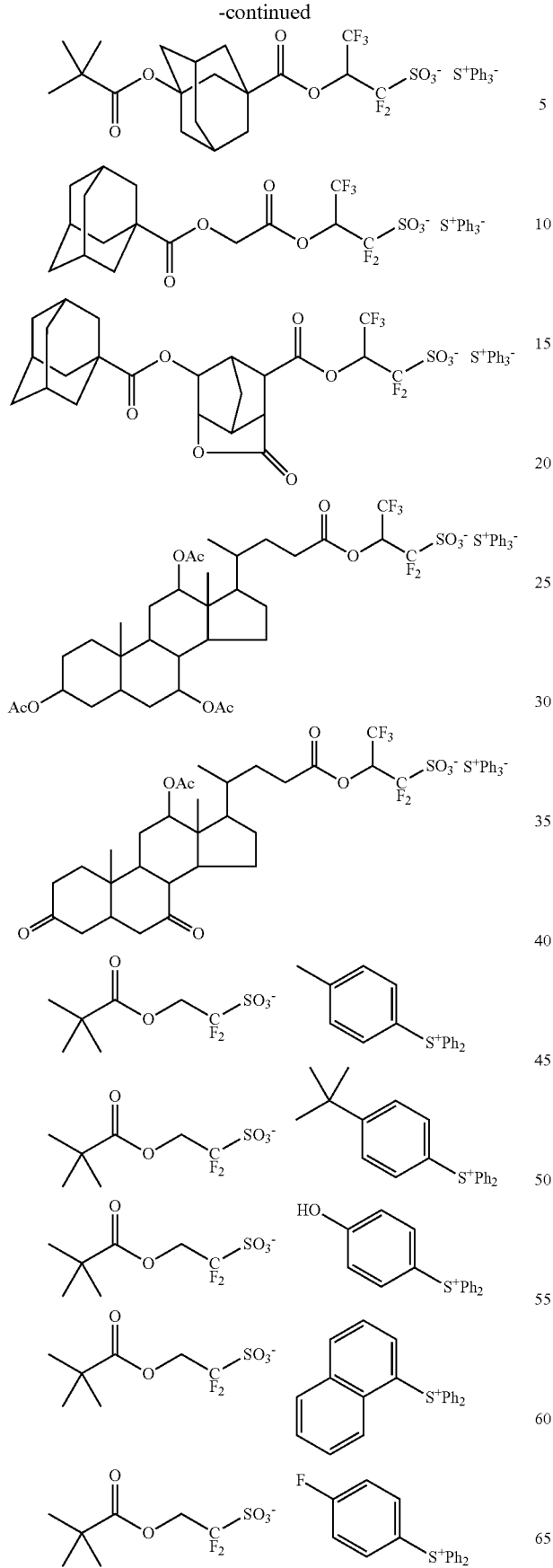
76
-continued
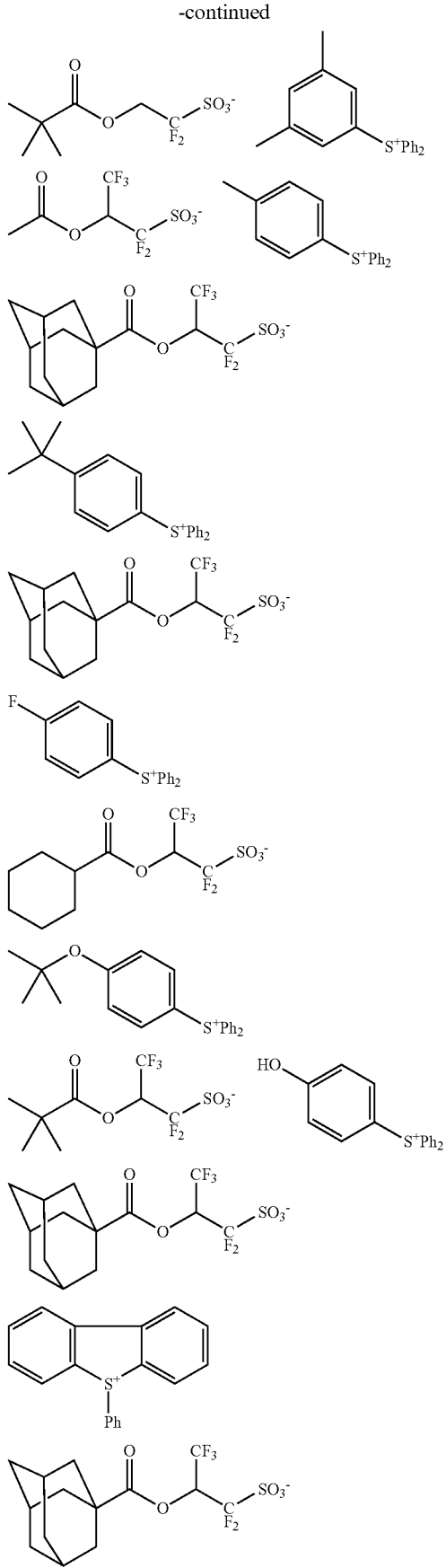

-continued

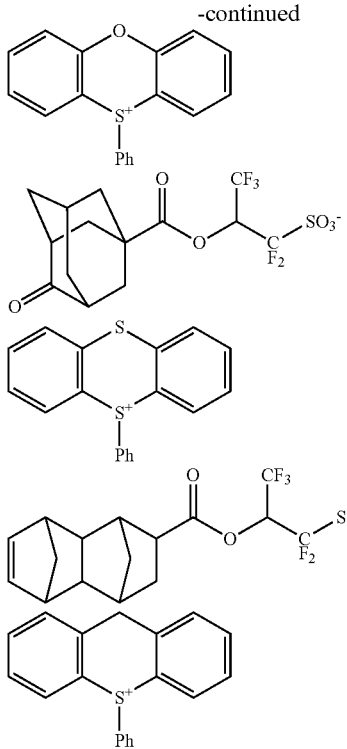
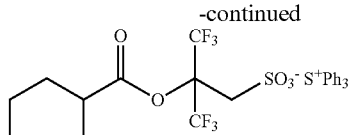
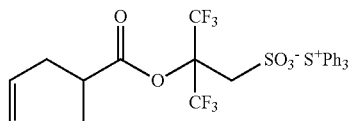
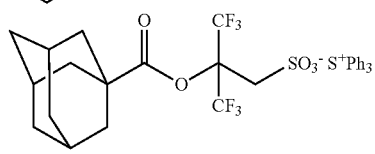
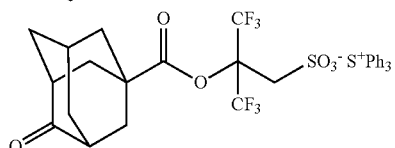
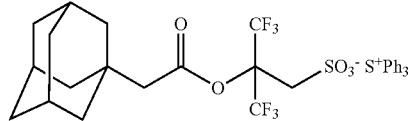
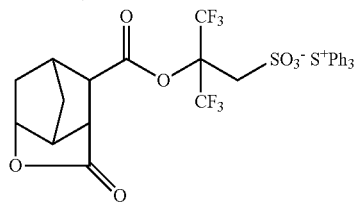
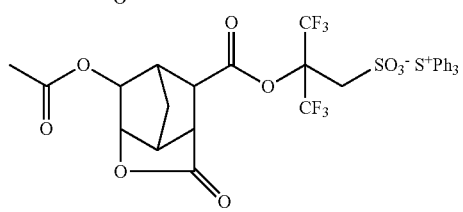
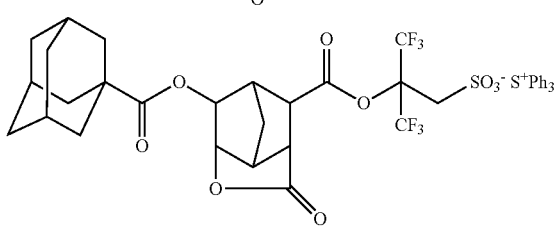

In formula (5B), $R^{fb1}$ and $R^{fb2}$ are each independently fluorine or a $C_1$-$C_{40}$ straight, branched or cyclic monovalent hydrocarbon group which may contain a heteroatom. Suitable monovalent hydrocarbon groups are as exemplified above for $R^{112}$. Preferably $R^{fb1}$ and $R^{fb2}$ each are fluorine or a $C_1$-$C_4$ straight fluorinated alkyl group. A pair of $R^{fb1}$ and $R^{fb2}$ may bond together to form a ring with the linkage (—$CF_2$—$SO_2$—$N^-$—$SO_2$—$CF_2$—) to which they are attached, and preferably the pair is a fluorinated ethylene or fluorinated propylene group forming a ring structure.

In formula (5C), $R^{fc1}$, $R^{fc2}$ and $R^{fc3}$ are each independently fluorine or a $C_1$-$C_{40}$ straight, branched or cyclic monovalent hydrocarbon group which may contain a heteroatom. Suitable monovalent hydrocarbon groups are as exemplified above for $R^{12}$. Preferably $R^{fc1}$, $R^{fc2}$ and $R^{fc3}$ each are fluorine or a $C_1$-$C_4$ straight fluorinated alkyl group. A pair of $R^{fc1}$ and $R^{fc2}$ may bond together to form a ring with the linkage (—$CF_2$—$SO_2$—$C^-$—$SO_2$—$CF_2$—) to which they are attached, and preferably the pair is a fluorinated ethylene or fluorinated propylene group forming a ring structure.

In formula (5D), $R^{fd}$ is a $C_1$-$C_{40}$ straight, branched or cyclic monovalent hydrocarbon group which may contain a heteroatom. Suitable monovalent hydrocarbon groups are as exemplified above for $R^{112}$.

With respect to the synthesis of the sulfonium salt having an anion of formula (5D), reference is made to JP-A 2010-215608.

Examples of the sulfonium salt having an anion of formula (5D) are shown below, but not limited thereto.

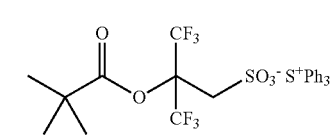
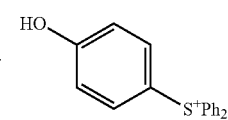

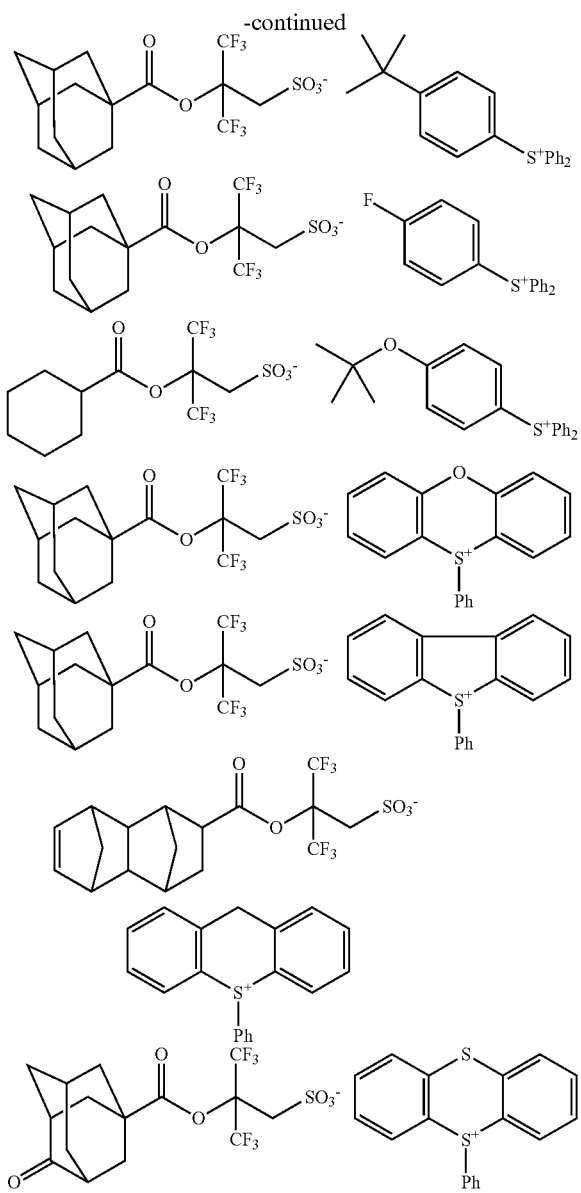

The compound having the anion of formula (5D) has a sufficient acid strength to cleave acid labile groups on the resist polymer because it is free of fluorine at α-position of sulfo group, but has two trifluoromethyl groups at β-position. Thus the compound is a useful PAG.

As the second PAG (D), those having the formula (6) are also preferred.

(6)

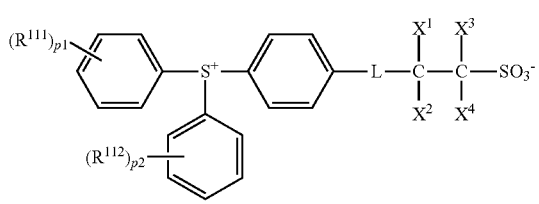

In formula (6), $R^{111}$ and $R^{112}$ are each independently a $C_1$-$C_{20}$ straight, branched or cyclic alkyl group, p1 and p2 are each independently an integer of 0 to 5. L is a single bond, ether bond, or a $C_1$-$C_{20}$ straight, branched or cyclic divalent hydrocarbon group which may contain a heteroatom. $X^1$, $X^2$, $X^3$ and $X^4$ are each independently hydrogen, fluorine or trifluoromethyl, at least one of $X^1$, $X^2$, $X^3$ and $X^4$ being a substituent group other than hydrogen.

Suitable alkyl groups include methyl, ethyl, propyl, isopropyl, n-butyl, s-butyl, t-butyl, t-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, and tricyclo[5.2.1.0$^{2,6}$]decanyl. Also included are the foregoing groups in which at least one hydrogen atom is substituted by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl radical, cyano radical, carbonyl radical, ether bond, ester bond, sulfonic acid ester bond, carbonate bond, lactone ring, sultone ring, carboxylic acid anhydride or haloalkyl radical.

Suitable divalent hydrocarbon groups include linear alkane diyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl; saturated cyclic divalent hydrocarbon groups such as cyclopentanediyl, cyclohexanediyl, norbornanediyl, and adamantanediyl; and unsaturated cyclic divalent hydrocarbon groups such as phenylene and naphthylene. Also included are the foregoing groups in which at least one hydrogen atom is replaced by an alkyl radical such as methyl, ethyl, propyl, n-butyl or t-butyl, or in which at least one hydrogen atom is replaced by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl radical, cyano radical, carbonyl radical, ether bond, ester bond, sulfonic acid ester bond, carbonate bond, lactone ring, sultone ring, carboxylic acid anhydride or haloalkyl radical. Suitable heteroatoms include oxygen, nitrogen, sulfur and halogen, with oxygen being preferred.

Examples of the PAG having formula (6) are shown below, but not limited thereto. Herein G is hydrogen, fluorine or trifluoromethyl.

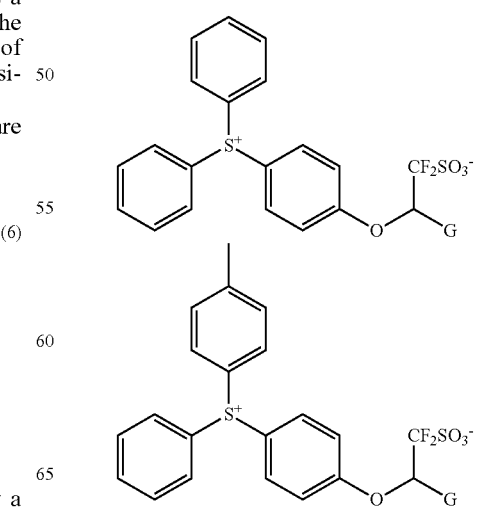

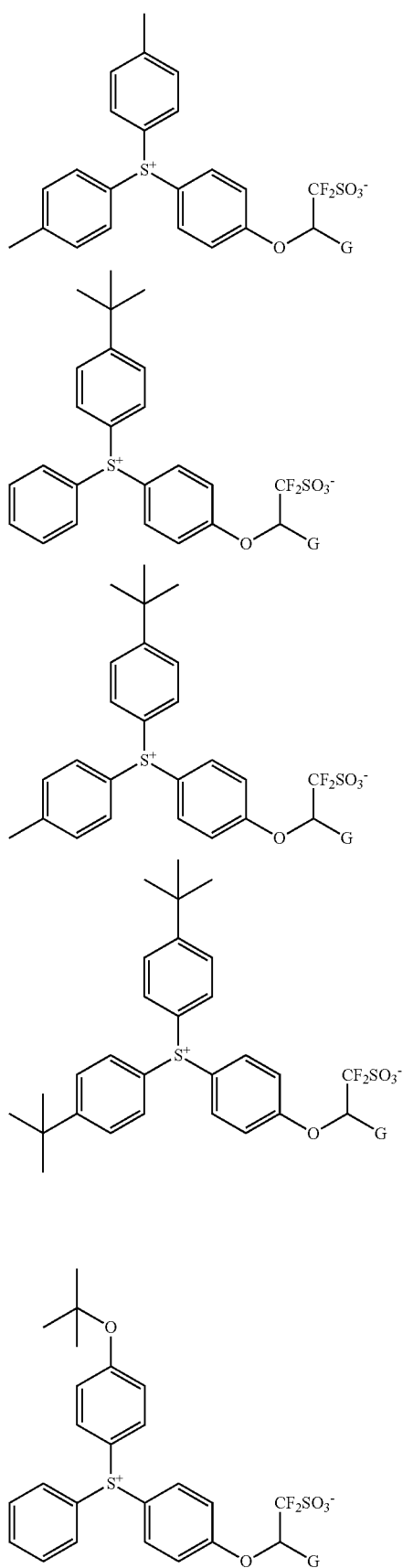
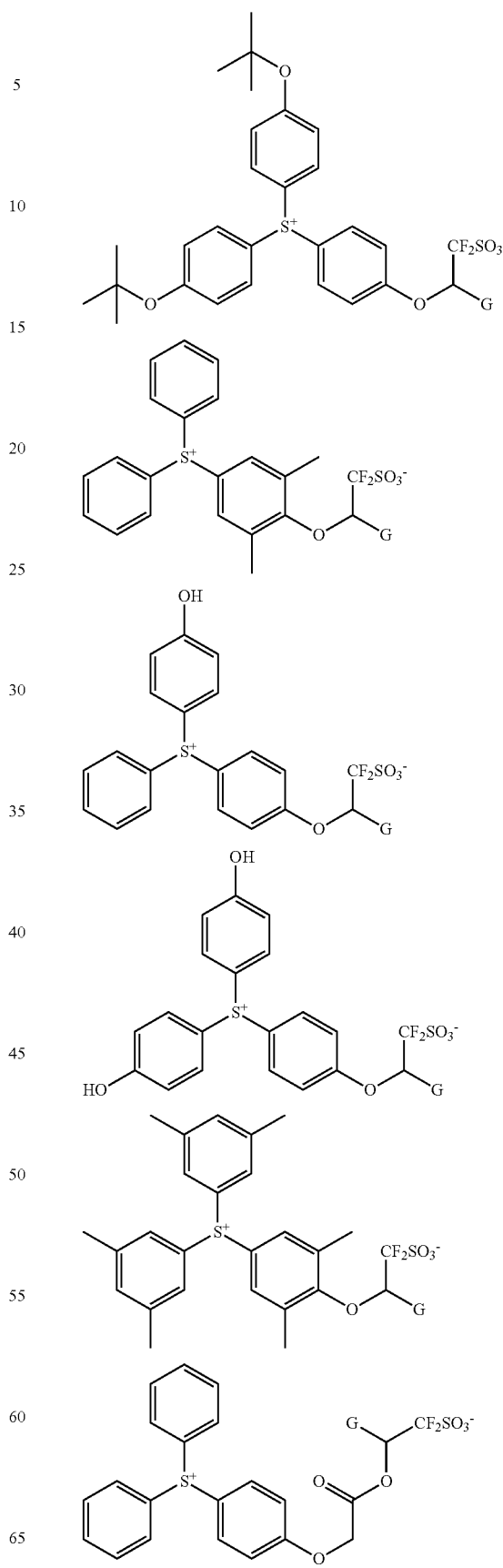

83
-continued
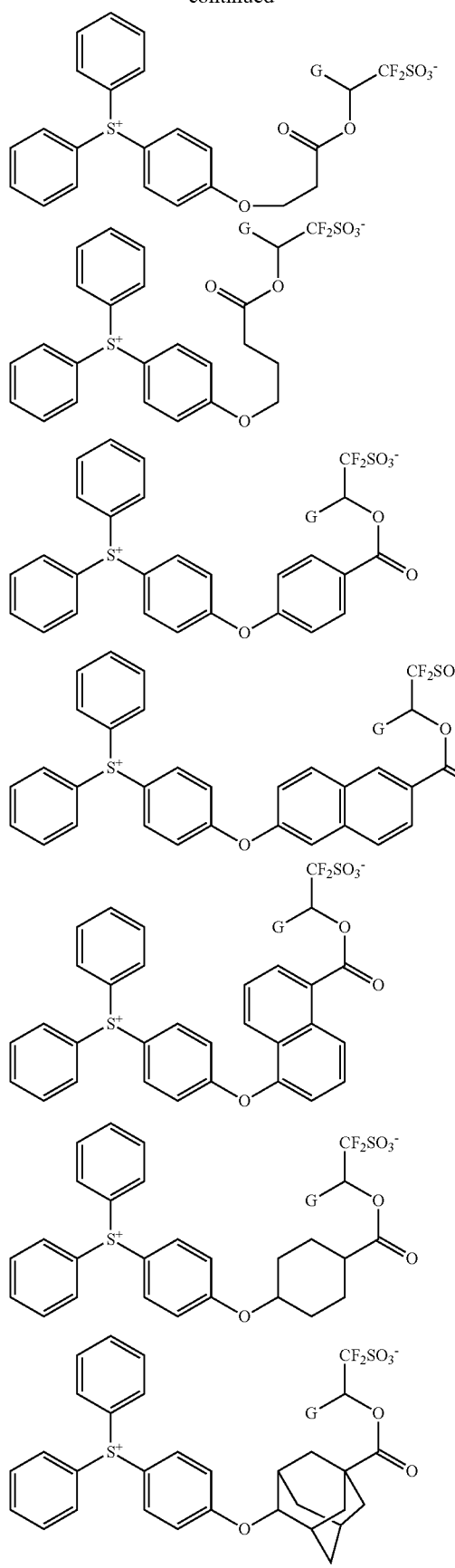
84
-continued
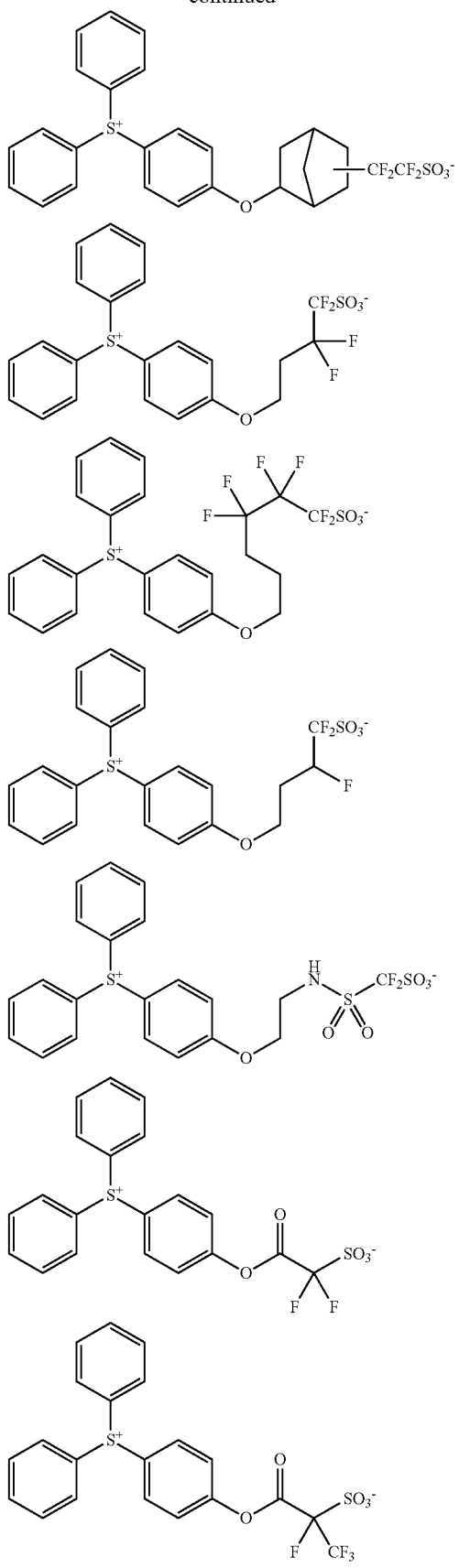

An appropriate amount of the PAG (D) added is 0 to 40 parts, more preferably 0.1 to 40 parts, and even more preferably 0.1 to 20 parts by weight per 100 parts by weight of the base resin (B). An amount in the range ensures good resolution and leaves no foreign particles after resist development or during separation. The second PAGs may be used alone or in admixture.

(E) Quencher

The resist composition may further comprise (E) a quencher. As used herein, the "quencher" refers to a compound capable of trapping the acid generated by the PAG.

As the quencher, onium salts having the formulae (7) and (8) are preferred.

$$R^{151}\!-\!SO_3^-M^+ \tag{7}$$

$$R^{152}\!-\!CO_2^-M^+ \tag{8}$$

Herein $R^{151}$ and $R^{152}$ are each independently hydrogen or a $C_1$-$C_{40}$ straight, branched or cyclic monovalent hydrocarbon group which may contain a heteroatom, excluding the hydrocarbon group in which the hydrogen atom bonded to the carbon at α-position relative to the sulfo group is substituted by fluorine or fluoroalkyl, and $M^+$ is an onium cation.

In formula (7), examples of the group $R^{151}$ include hydrogen, methyl, ethyl, propyl, isopropyl, n-butyl, s-butyl, t-butyl, t-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, adamantyl, phenyl, naphthyl, and anthracenyl. Also included are the foregoing groups in which at least one hydrogen atom is substituted by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl radical, cyano radical, carbonyl radical, ether bond, ester bond, sulfonic acid ester bond, carbonate bond, lactone ring, sultone ring, carboxylic acid anhydride or haloalkyl radical.

In formula (8), examples of the group $R^{152}$ include fluorinated alkyl groups such as trifluoromethyl and trifluoroethyl and fluorinated aryl groups such as pentafluorophenyl and 4-trifluoromethylphenyl as well as those exemplified above for $R^{151}$.

Suitable structures of the anion moiety in formula (7) are shown below, but not limited thereto.

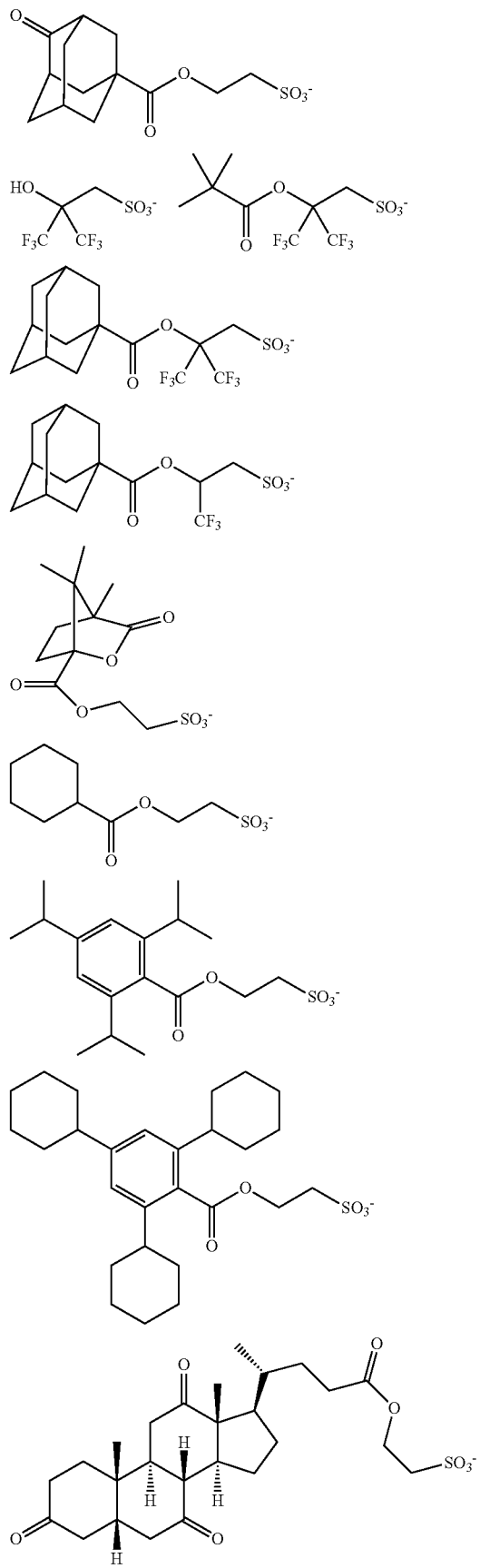

87
-continued
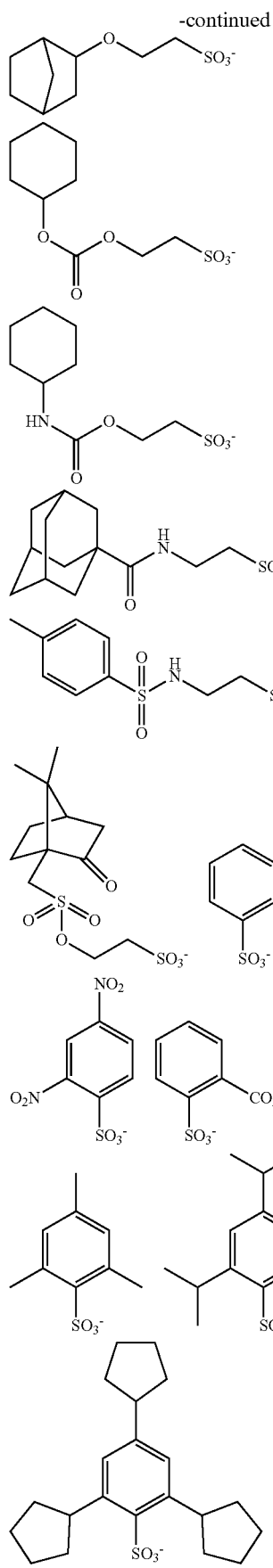
88
-continued
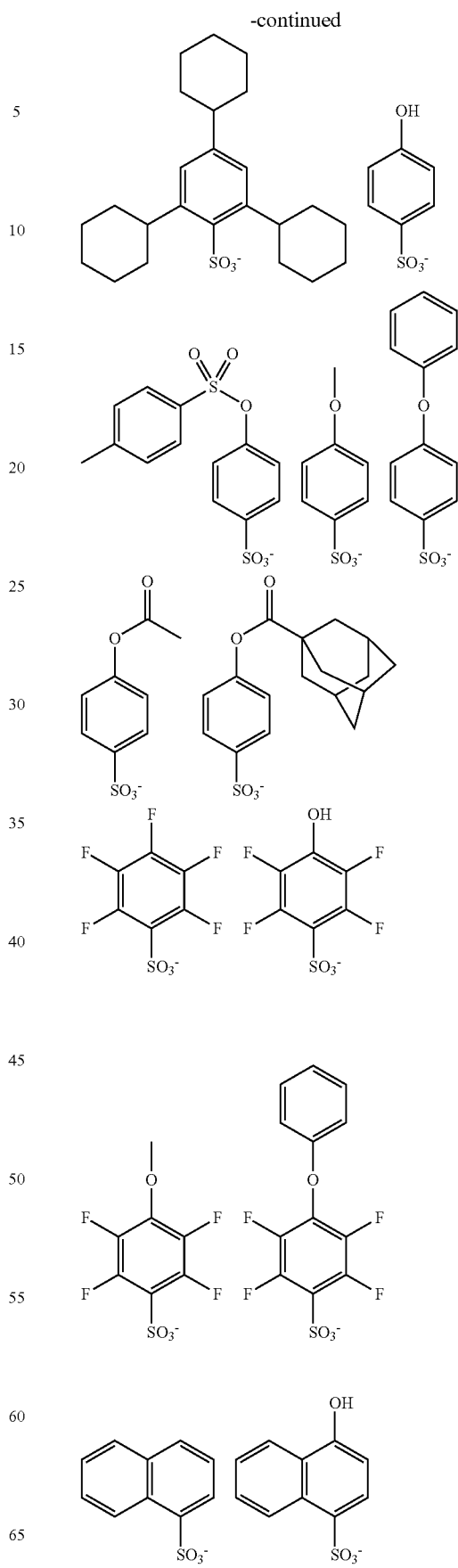

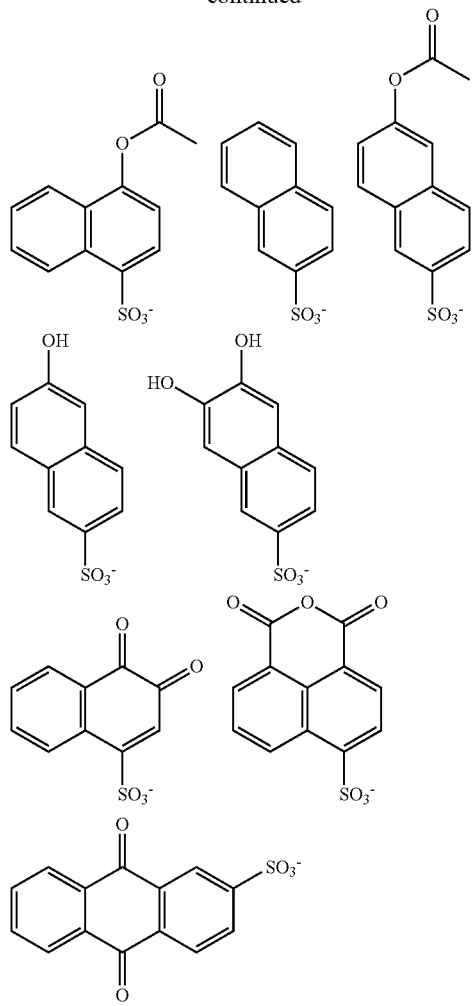
Suitable structures of the anion moiety in formula (8) are shown below, but not limited thereto.
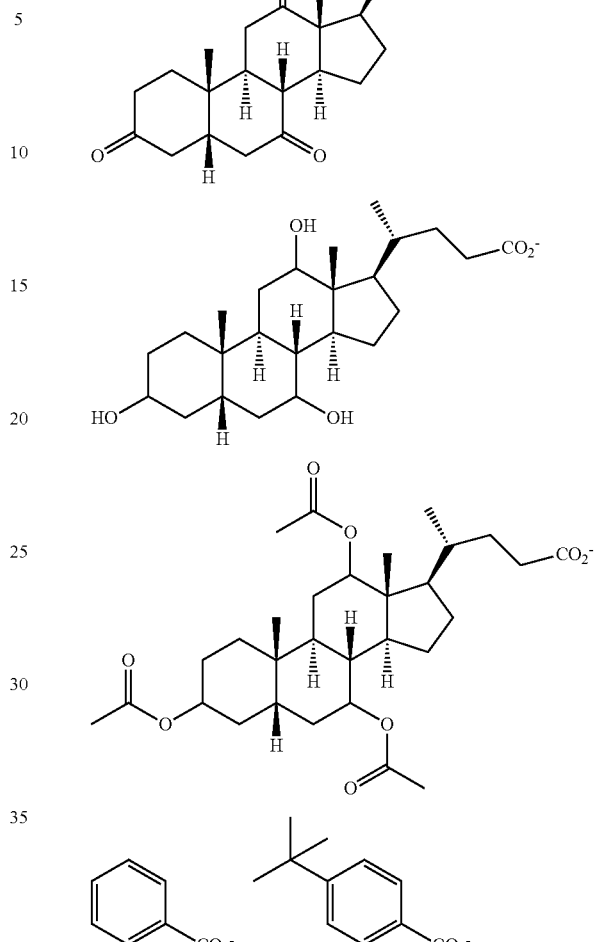
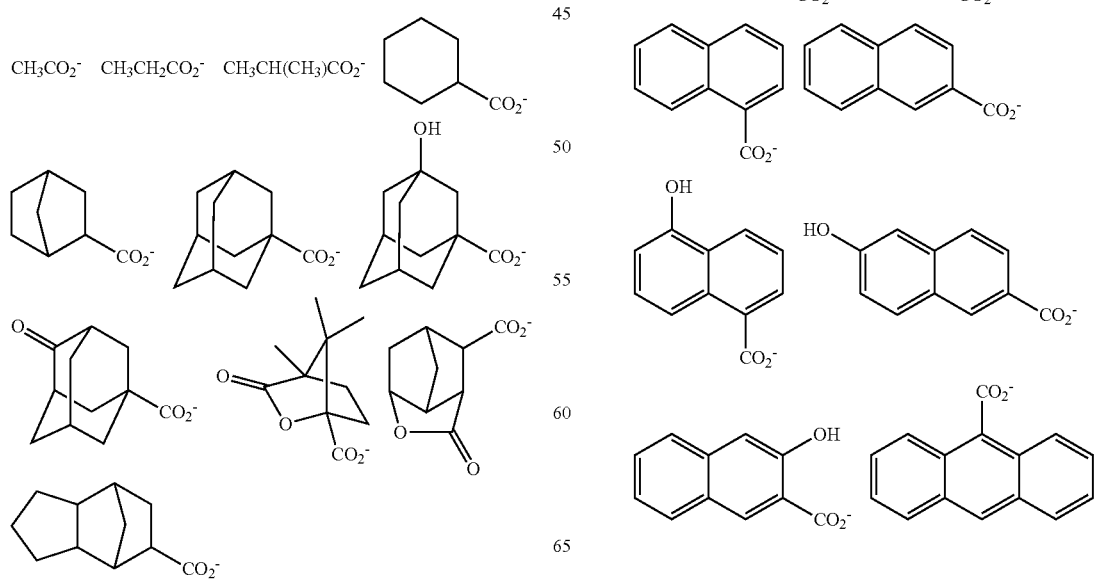

-continued

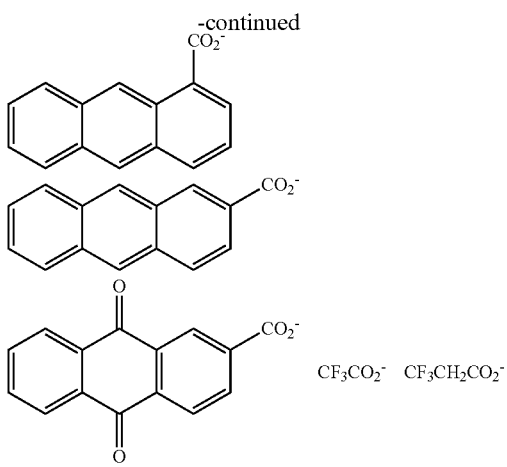

As the onium cation in formulae (7) and (8), those having the following formulae (9), (10) and (11) are preferred.

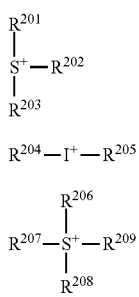

Herein $R^{201}$ to $R^{209}$ are each independently a $C_1$-$C_{20}$ straight, branched or cyclic monovalent hydrocarbon group which may contain a heteroatom. Any two of $R^{201}$ to $R^{203}$ may bond together to form a ring with the sulfur atom to which they are attached. $R^{204}$ and $R^{205}$ may bond together to form a ring with the iodine atom to which they are attached. Any two of $R^{206}$ to $R^{209}$ may bond together to form a ring with the nitrogen atom to which they are attached. Suitable monovalent hydrocarbon groups include alkyl groups such as methyl, ethyl, propyl, isopropyl, n-butyl, s-butyl, t-butyl, t-pentyl, n-pentyl, n-hexyl, n-octyl, cyclopentyl, cyclohexyl, 2-ethylhexyl, cyclopentylmethyl, cyclopentylethyl, cyclohexylmethyl, cyclohexylethyl, norbornyl, oxanorbornyl, tricyclo[5.2.1.0$^{2,6}$]decanyl, and adamantyl, and aryl groups such as phenyl and naphthyl. Also included are the foregoing groups in which at least one hydrogen atom is substituted by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl radical, cyano radical, carbonyl radical, ether bond, ester bond, sulfonic acid ester bond, carbonate bond, lactone ring, sultone ring, carboxylic acid anhydride or haloalkyl radical.

Examples of the onium cation are shown below, but not limited thereto.

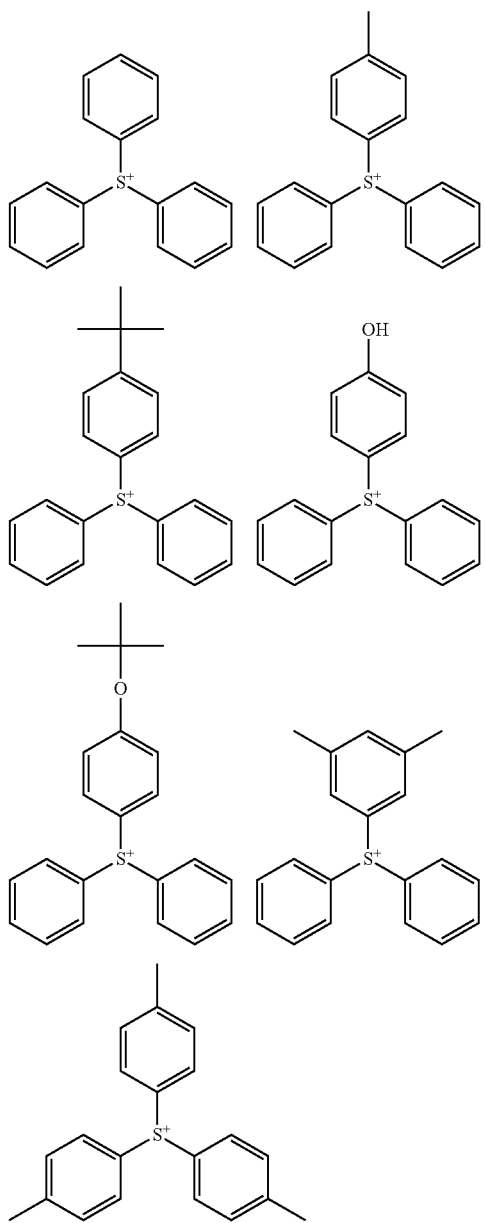

-continued
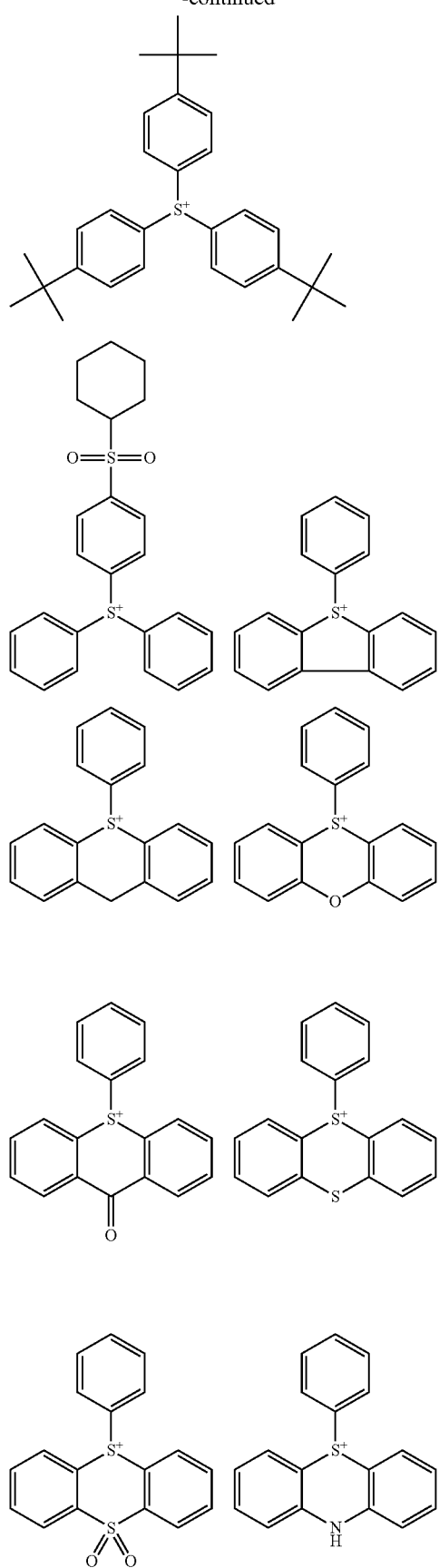
-continued
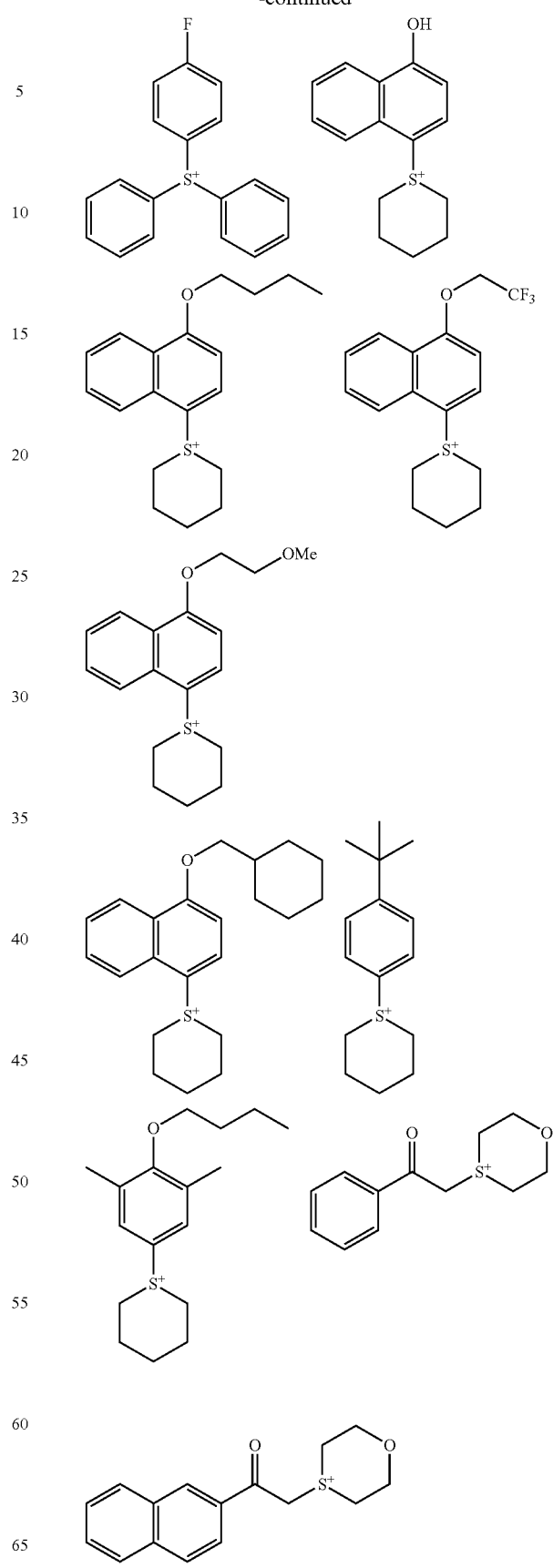

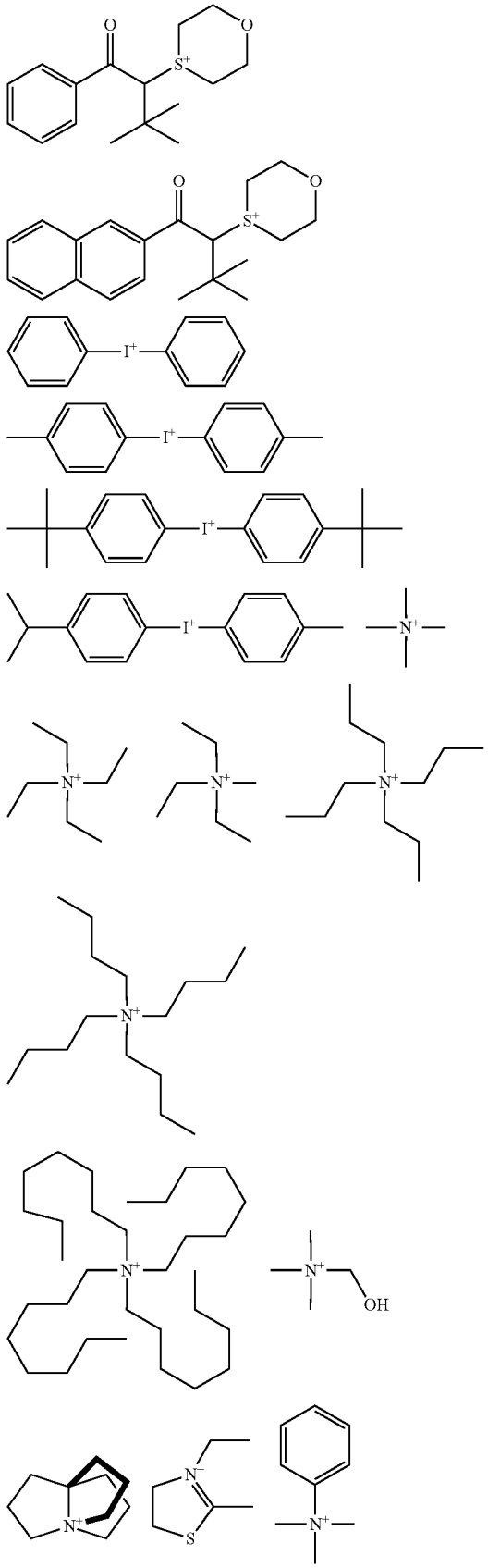
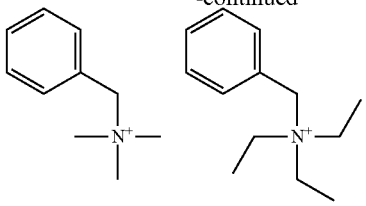
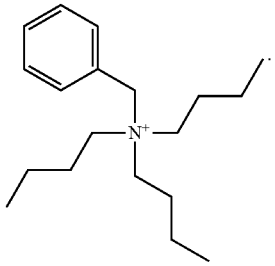
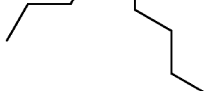

Examples of the onium salt having formula (7) or (8) include any combinations of the foregoing anions and onium cations. Such an onium salt may be readily prepared by ion exchange reaction using any well-known organic chemistry techniques. The ion exchange reaction may be conducted in a standard way, with reference to JP-A 2007-145797, for example.

The onium salt having formula (7) or (8) functions as a quencher since the anion therein is a conjugated base of weak acid. As used herein, the weak acid indicates an acidity insufficient to deprotect an acid labile group from an acid labile group-containing unit in the base resin. The onium salt having formula (7) or (8) functions as a quencher when used in combination with an onium salt type photoacid generator having a conjugated base of a strong acid, typically a sulfonic acid which is fluorinated at α-position as the counter anion. In a system using a mixture of an onium salt capable of generating a strong acid (e.g., α-position fluorinated sulfonic acid) and an onium salt capable of generating a weak acid (e.g., α-position non-fluorinated sulfonic acid or carboxylic acid), if the strong acid generated from the photoacid generator upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion. In this way, the onium salt functions as a quencher.

If a photoacid generator capable of generating a strong acid is an onium salt, an exchange from the strong acid generated upon exposure to high-energy radiation to a weak acid as above can take place, but it rarely happens that the weak acid generated upon exposure to high-energy radiation collides with the unreacted onium salt capable of generating a strong acid to induce a salt exchange. This is because of a likelihood of an onium cation forming an ion pair with a stronger acid anion.

An appropriate amount of the onium salt having formula (7) or (8) is 0 to 40 parts, preferably 0.1 to 40 parts, more preferably 0.1 to 20 parts by weight, per 100 parts by weight of the base resin (B). A larger amount of the onium salt beyond the upper limit may cause degradation of resolution or leave foreign particles after resist development or during stripping. The onium salt having formula (7) or (8) may be used alone or in combination.

As the quencher (E), a photo-degradable onium salt having a nitrogen-containing substituent group may be used in combination with the onium salt having formula (7) or (8), if desired. This compound functions as a quencher in the unexposed region, but as a so-called photo-degradable base in the exposed region because it loses the quencher function in the exposed region due to neutralization thereof with the acid generated by itself. Using a photo-degradable base, the contrast between exposed and unexposed regions can be further enhanced. With respect to the photo-degradable base, reference may be made to JP-A 2009-109595, 2012-046501, and JP-A 2013-209360, for example.

An appropriate amount of the photo-degradable base is 0 to 40 parts, preferably 0.1 to 40 parts, more preferably 0.1 to 20 parts by weight, per 100 parts by weight of the base resin (B). A larger amount of the photo-degradable base beyond the upper limit may cause degradation of resolution or leave foreign particles after resist development or during stripping. The photo-degradable base may be used alone or in admixture.

An amine compound may be added to the resist composition as the quencher. The amine compound is capable of suppressing the rate of diffusion when the acid generated by the PAG diffuses within the resist film. Suitable amine compounds include primary, secondary and tertiary amine compounds, specifically amine compounds having a hydroxyl, ether, ester, lactone, cyano or sulfonate group, as described in JP-A 2008-111103, paragraphs [0146] to [0164] (U.S. Pat. No. 7,537,880), and compounds having primary or secondary amine protected as a carbamate group, as described in JP 3790649.

The amine compound may be used alone or in admixture of two or more. An appropriate amount of the amine compound is 0 to 12 parts, preferably 0.001 to 12 parts, more preferably 0.01 to 8 parts by weight, per 100 parts by weight of the base resin (B). The inclusion of amine compound facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile. The inclusion of amine compound is also effective for improving adhesion to the substrate.

(F) Surfactant

The resist composition may further comprise (F) a surfactant which is insoluble or substantially insoluble in water and soluble in alkaline developer, and/or a surfactant which is insoluble or substantially insoluble in water and alkaline developer (hydrophobic resin). For the surfactant, reference should be made to those compounds described in JP-A 2010-215608 and JP-A 2011-016746.

While many examples of the surfactant which is insoluble or substantially insoluble in water and alkaline developer are described in the patent documents cited herein, preferred examples are FC-4430, Surflon® S-381, Surfynol® E1004, KH-20 and KH-30, which may be used alone or in admixture. Partially fluorinated oxetane ring-opened polymers having the formula (surf-1) are also useful.

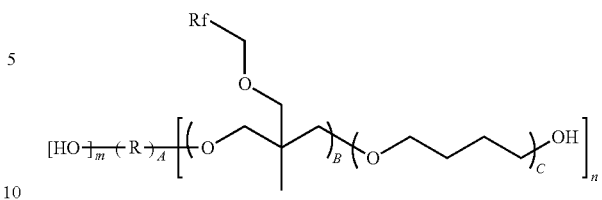

(surf-1)

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

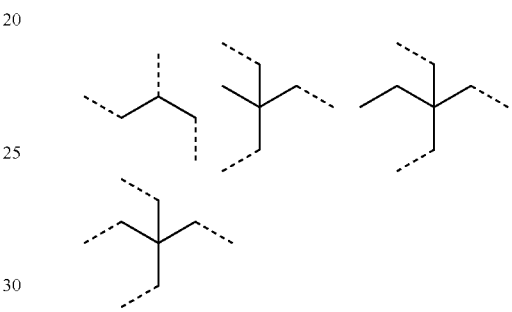

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. A is equal to 1, B is an integer of 2 to 25, and C is an integer of 0 to 10. Preferably, B is an integer of 4 to 20, and C is 0 or 1. Note that the formula (surf-1) does not prescribe the arrangement of respective constituent units while they may be arranged either blockwise or randomly. For the preparation of surfactants in the form of partially fluorinated oxetane ring-opened polymers, reference should be made to U.S. Pat. No. 5,650,483, for example.

The surfactant which is insoluble or substantially insoluble in water and soluble in alkaline developer is useful when ArF immersion lithography is applied to the resist composition in the absence of a resist protective film. In this embodiment, the surfactant has a propensity to segregate on the resist surface after spin coating for achieving a function of minimizing water penetration or leaching. The surfactant is also effective for preventing water-soluble components from being leached out of the resist film for minimizing any damage to the exposure tool. The surfactant becomes solubilized during alkaline development following exposure and PEB, and thus forms few or no foreign particles which become defects. The preferred surfactant is a polymeric surfactant which is insoluble or substantially insoluble in water, but soluble in alkaline developer, also referred to as "hydrophobic resin" in this sense, and especially which is water repellent and enhances water slippege.

Suitable polymeric surfactants are shown below.

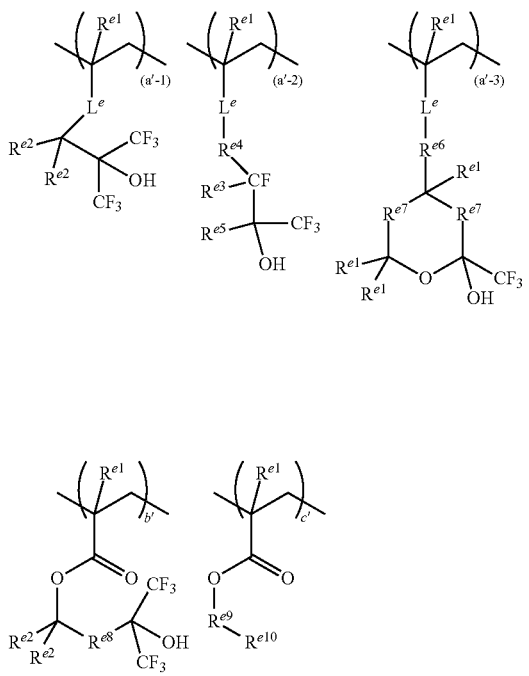

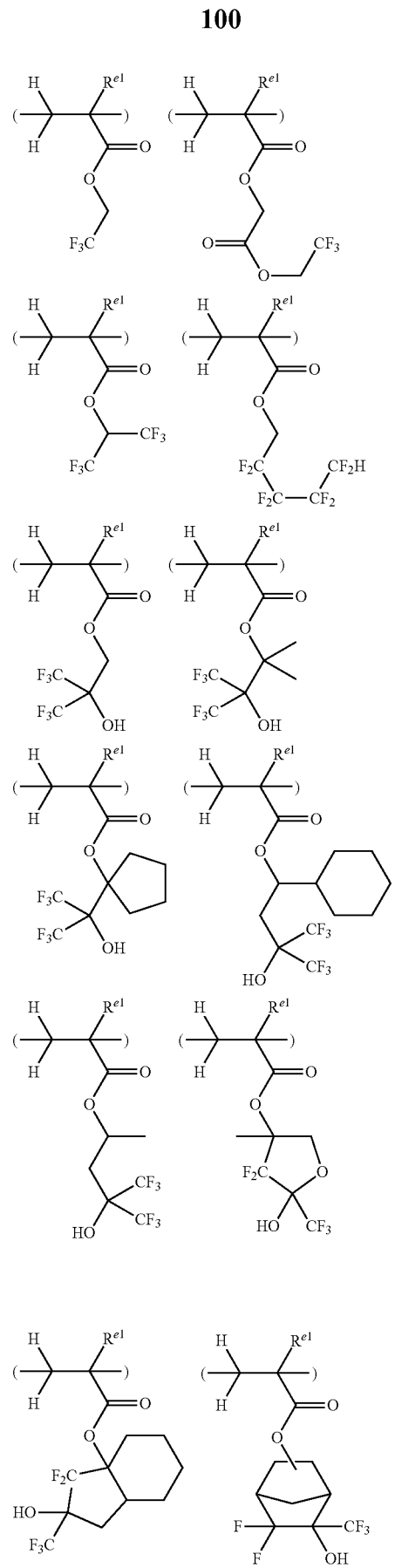

Herein $R^{e1}$ is each independently hydrogen, fluorine, methyl or trifluoromethyl. $R^{e2}$ is each independently hydrogen or a straight, branched or cyclic $C_1$-$C_{20}$ alkyl or fluoroalkyl group, or two $R^{e2}$ in a common unit may bond together to form a ring with the carbon atom to which they are attached, and in this event, they together represent a straight, branched or cyclic $C_2$-$C_{20}$ alkylene or fluoroalkylene group.

$R^{e3}$ is fluorine or hydrogen, or $R^{e3}$ may bond with $R^{e4}$ to form a non-aromatic ring of 3 to 10 carbon atoms in total with the carbon atom to which they are attached. $R^{e4}$ is a straight, branched or cyclic $C_1$-$C_6$ alkylene group in which at least one hydrogen atom may be substituted by a fluorine atom. $R^{e5}$ is a straight or branched $C_1$-$C_{10}$ alkyl group in which at least one hydrogen atom is substituted by a fluorine atom. Alternatively, $R^{e4}$ and $R^{e5}$ may bond together to form a non-aromatic ring with the carbon atoms to which they are attached. In this event, $R^{e4}$, $R^{e5}$ and the carbon atoms to which they are attached together represent a trivalent organic group of 3 to 12 carbon atoms in total. $R^{e6}$ is a single bond or a $C_1$-$C_4$ alkylene.

$R^{e7}$ is each independently a single bond, —O—, or —$CR^{e1}R^{e1}$—. $R^{e8}$ is a straight $C_1$-$C_4$ or branched $C_3$-$C_4$ alkylene group, or may bond with $R^{e2}$ within a common unit to form a $C_3$-$C_6$ non-aromatic ring with the carbon atom to which they are attached. $R^{e9}$ is 1,2-ethylene, 1,3-propylene or 1,4-butylene.

$R^{e10}$ is a $C_3$-$C_6$ linear perfluoroalkyl group, typically 3H-perfluoropropyl, 4H-perfluorobutyl, 5H-perfluoropentyl or 6H-perfluorohexyl. $L^e$ is each independently —C(=O)—O—, —O—, or —C(=O)—$R^{e11}$—C(=O)—O—. $R^{e11}$ is a straight, branched or cyclic $C_1$-$C_{10}$ alkylene group. The subscripts are in the range: $0 \leq (a'-1) \leq 1$, $0 \leq (a'-2) \leq 1$, $0 \leq (a'-3) \leq 1$, $0 \leq b' \leq 1$, $0 \leq c' \leq 1$, and $0 < (a'-1)+(a'-2)+(a'-3)+b'+c' \leq 1$.

Examples of these recurring units are shown below, but not limited thereto. Herein $R^{e1}$ is as defined above.

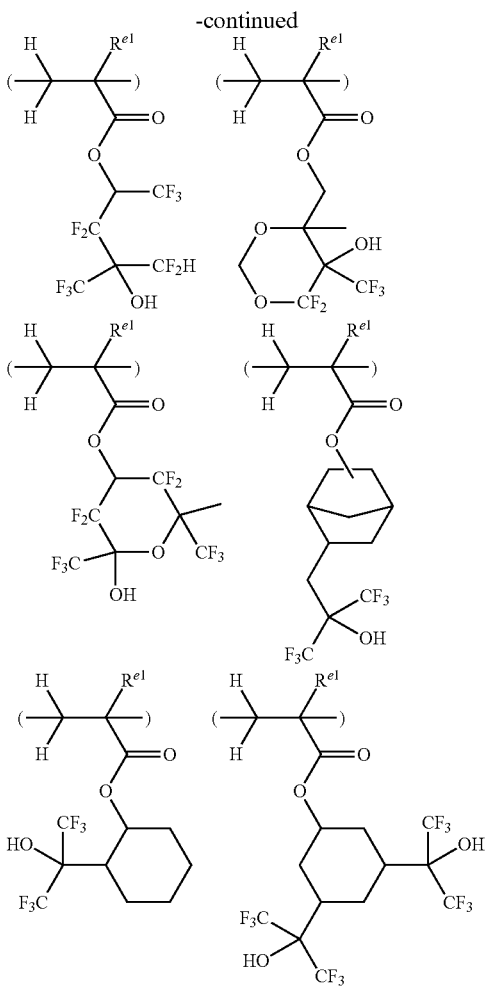

For the surfactant which is insoluble or substantially insoluble in water and soluble in alkaline developer, reference may be made to JP-A 2008-122932, 2009-098638, 2009-191151, 2009-192784, 2009-276363, 2010-107695, 2010-134012, 2010-250105, and 2011-042789.

The polymeric surfactant has a Mw of preferably 1,000 to 50,000, more preferably 2,000 to 20,000 as measured by GPC versus polystyrene standards. A surfactant with a Mw within the range may be effective for surface modification and cause no development defects.

An appropriate amount of component (F) is 0 to 20 parts by weight per 100 parts by weight of the base resin (B). The lower limit is preferably 0.001 part, and more preferably 0.01 part by weight, whereas the upper limit is preferably 15 parts, and more preferably 10 parts by weight, Process A further embodiment of the invention is a pattern forming process using the resist composition defined above. A pattern may be formed from the resist composition using any well-known lithography process. The preferred process includes at least the steps of forming a resist film on a substrate, exposing it to high-energy radiation, and developing it in a developer.

Specifically, the resist composition is applied onto a substrate for integrated circuitry fabrication (e.g., Si, $SiO_2$, SiN, SiON, TiN, WSi, BPSG, SOG, organic antireflective film, etc.) or a substrate for mask circuitry fabrication (e.g., Cr, CrO, CrON, $MoSi_2$, $SiO_2$, etc.) by a suitable coating technique such as spin coating. The coating is prebaked on a hotplate at a temperature of 60 to 150° C. for 1 to 10 minutes, preferably 80 to 140° C. for 1 to 5 minutes. The resulting resist film is generally 0.05 to 2 μm thick.

Through a photomask having a desired pattern disposed over the substrate, the resist film is then exposed to high-energy radiation such as KrF excimer laser, ArF excimer laser or EUV in an exposure dose preferably in the range of 1 to 200 $mJ/cm^2$, more preferably 10 to 100 $mJ/cm^2$. Alternatively, pattern formation may be performed by writing with EB directly in a dose of preferably 1 to 300 $\mu C/cm^2$, more preferably 10 to 200 $\mu C/cm^2$. Light exposure may be done by a conventional lithography process or in some cases, by an immersion lithography process of providing a liquid having a refractive index of at least 1.0 between the projection lens and the resist film. The preferred liquid is water. In the case of immersion lithography, a protective film which is insoluble in water may be formed on the resist film.

The resist film is then baked (PEB) on a hotplate at 60 to 150° C. for 1 to 5 minutes, and preferably at 80 to 140° C. for 1 to 3 minutes. Finally, development is carried out using as the developer an aqueous alkaline solution, such as a 0.1 to 5 wt %, preferably 2 to 3 wt %, aqueous solution of tetramethylammonium hydroxide (TMAH), this being done by a conventional method such as dip, puddle, or spray development for a period of 0.1 to 3 minutes, and preferably 0.5 to 2 minutes. In this way the desired pattern is formed on the substrate.

While the water-insoluble protective film which is used in the immersion lithography serves to prevent any components from being leached out of the resist film and to improve water slippage at the film surface, it is generally divided into two types. The first type is an organic solvent-strippable protective film which must be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

Any desired step may be added to the pattern forming process. For example, after a photoresist film is formed, a step of rinsing with pure water (post-soaking) may be introduced to extract the acid generator or the like from the film surface or wash away particles. After exposure, a step of rinsing (post-soaking) may be introduced to remove any water remaining on the film after exposure.

A pattern may also be formed by a double patterning process. The double patterning process includes a trench process of processing an underlay to a 1:3 trench pattern by a first step of exposure and etching, shifting the position, and forming a 1:3 trench pattern by a second step of exposure for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

In the pattern forming process, an alkaline aqueous solution is often used as the developer. The negative tone development technique using an organic solvent instead is also applicable wherein the unexposed region is developed and dissolved in the organic solvent.

In the organic solvent development, the organic solvent used as the developer is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, butenyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate. These organic solvents may be used alone or in admixture of two or more.

EXAMPLE

Synthesis Examples, Examples and Comparative Examples are given below by way of illustration and not by way of limitation. The abbreviation "pbw" is parts by weight. For all polymers, Mw and Mn are determined by GPC versus polystyrene standards using THF solvent. THF stands for tetrahydrofuran, MEK for methyl ethyl ketone, and MIBK for methyl isobutyl ketone. Analytic instruments are as shown below.

IR: NICOLET 6700 by Thermo Fisher Scientific Inc.
$^1$H-NMR: ECA-500 by JEOL Ltd.
$^{19}$F-NMR ECA-500 by JEOL Ltd.
MALDI-TOF-MS: S3000 by JEOL Ltd.
GC-MS: GC.6890N MS.5973 by Agilent Technologies 1) Synthesis of Sulfonium Compounds Example 1-1

Synthesis of Intermediate A

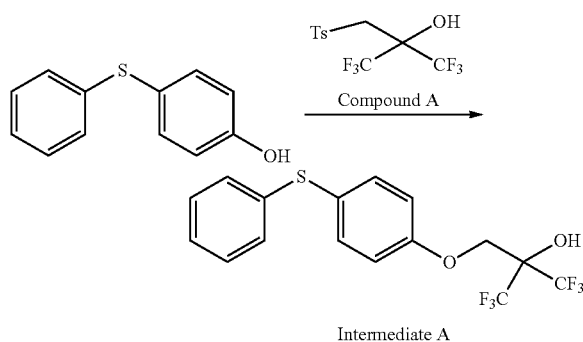

Intermediate A

In a mixture of 550 g of THF and 133 g of water was dissolved 220 g of 4-phenylthiophenyl. At room temperature, 25 wt % caustic soda was added dropwise to the solution, which was aged for 15 minutes. Thereafter, a solution of 352 g of Compound A in 250 g of THF was added dropwise thereto at room temperature. The solution was aged overnight, after which 5 wt % hydrochloric acid was added thereto for quenching. The reaction solution was diluted with 620 g of hexane and 620 g of toluene, and washed with water. 1 wt % caustic soda was added to the organic layer, followed by separation. The organic layer was combined with 2.5 wt % hydrochloric acid and washed with water again, followed by separation. The organic layer was concentrated, obtaining 208 g of the end compound, Intermediate A as colorless oily matter (yield 65%).

Figure 2:
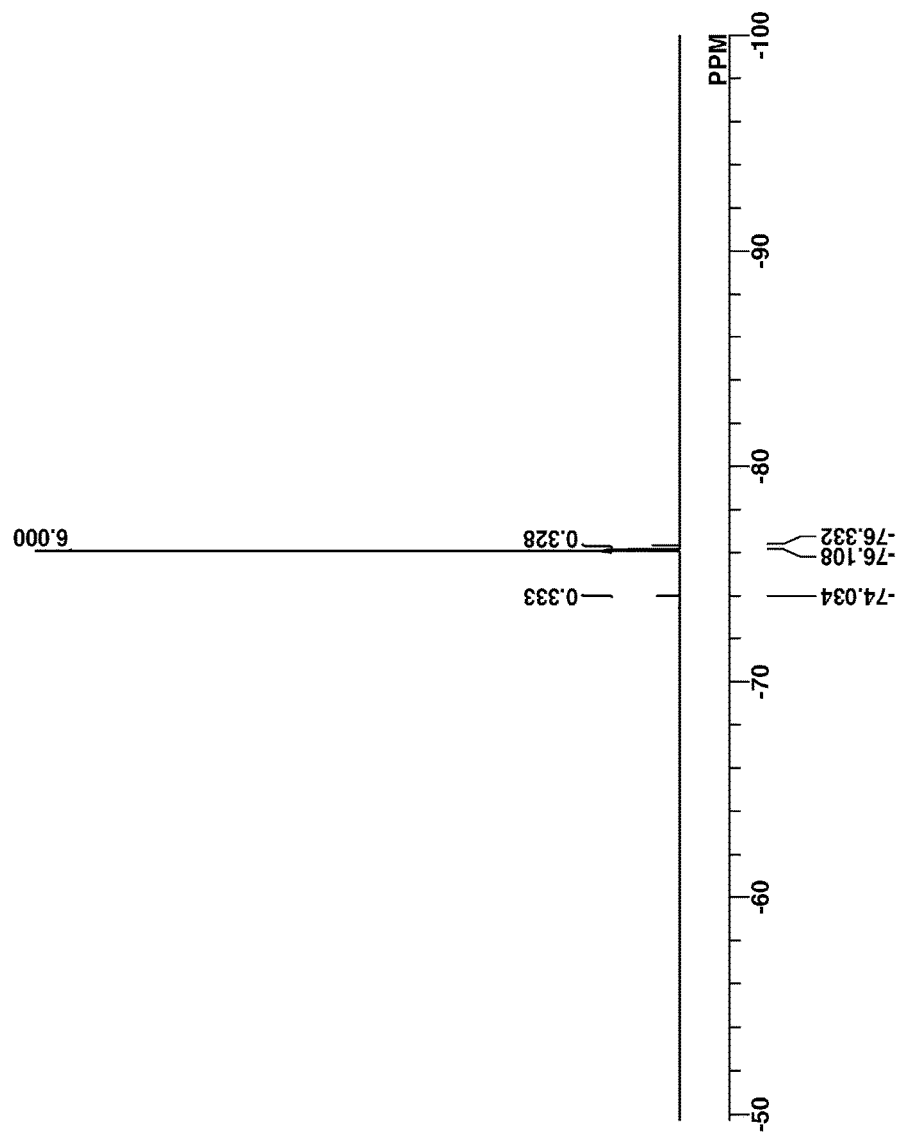

Intermediate A was analyzed by spectroscopy. The NMR spectra, $^1$H- and $^{19}$F-NMR in DMSO-d are shown in FIGS. 1 and 2. In $^1$H-NMR analysis, minute amounts of residual solvents (diisopropyl ether, MIBK, water) were observed.

IR (D-ATR): 3527, 3072, 1594, 1583,1494, 1478, 1440, 1408, 1373, 1320, 1222, 1171, 1084, 1062, 1025, 1011, 983, 918, 828, 741, 729, 690 cm$^{-1}$
GC-MS: [M] 382

Example 1-2

Synthesis of Intermediate B

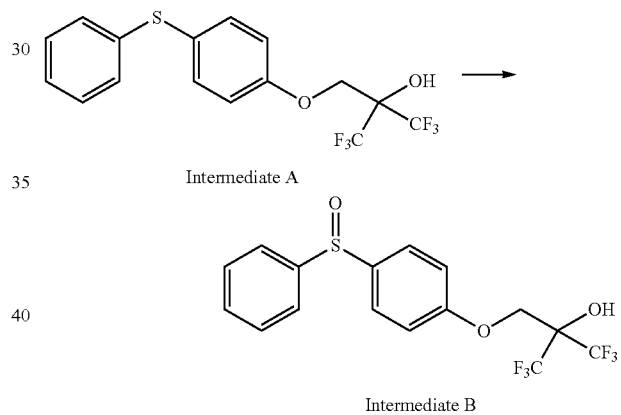

Intermediate B

Intermediate A, 183 g, was dissolved in 1,300 g of acetic acid. Under ice cooling, 51 g of 35 wt % hydrogen peroxide water was added to the solution. The solution was aged overnight at room temperature, after which 25 g of sodium thiosulfate in 120 g of water was added dropwise at room temperature. After 1 hour of stirring, the reaction solution was diluted with 2,000 g of ethyl acetate and 1,000 g of toluene and washed with 1,000 g of water. The organic layer was combined with 1 wt % caustic soda, followed by separation. Once the organic layer was washed with water, the organic layer was combined with 2.5 wt % hydrochloric acid, followed by separation. The organic layer was washed with water and concentrated, after which ethyl acetate was added to the concentrate to form a 50 wt % ethyl acetate solution. The solution was added dropwise to a mixture of n-hexane and toluene (2:1 in weight ratio) for crystallization. The resulting white powder was dried in vacuum, obtaining 118 g of the end compound, Intermediate B.

Figure 3:
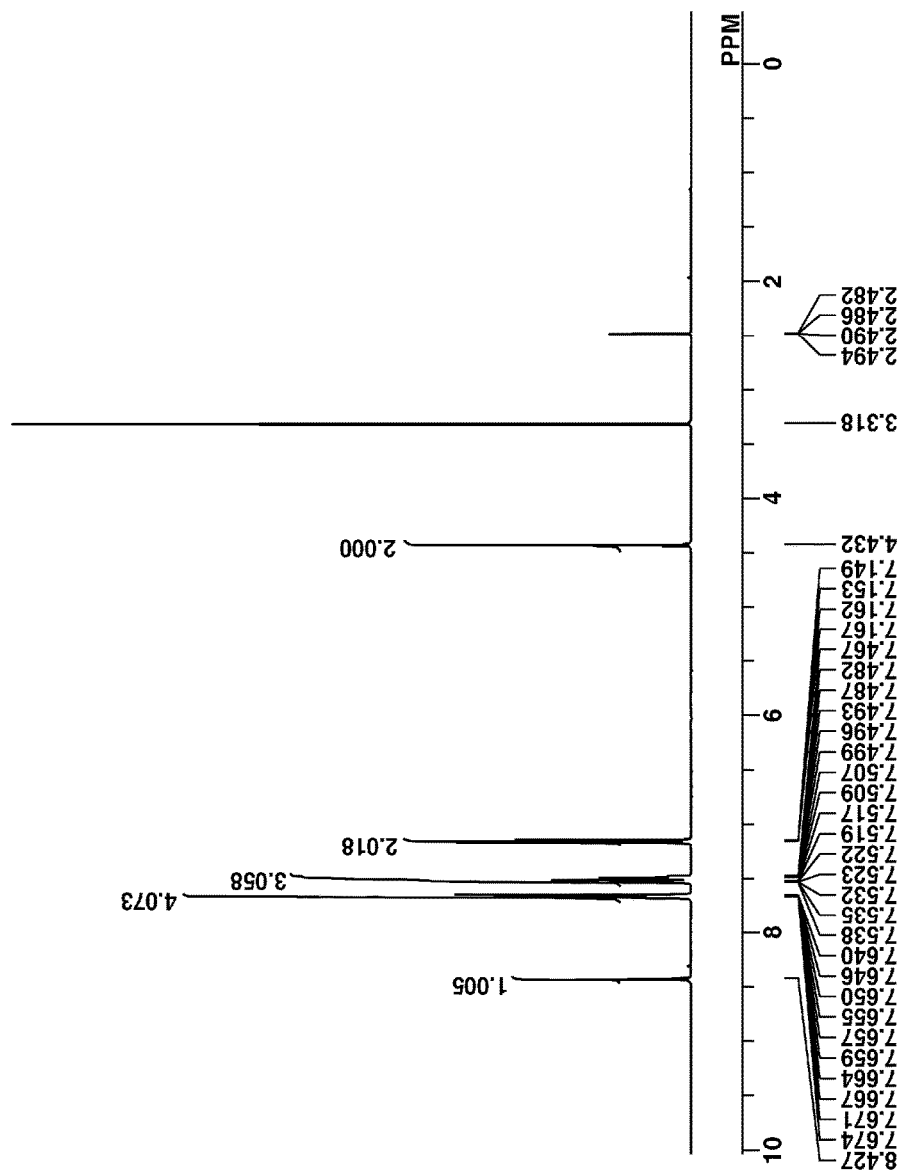
FIGS. 3 and 4 are diagrams showing $^1$H- and $^{19}$F-NMR spectra of the compound of Example 1-2, respectively.
Figure 4:
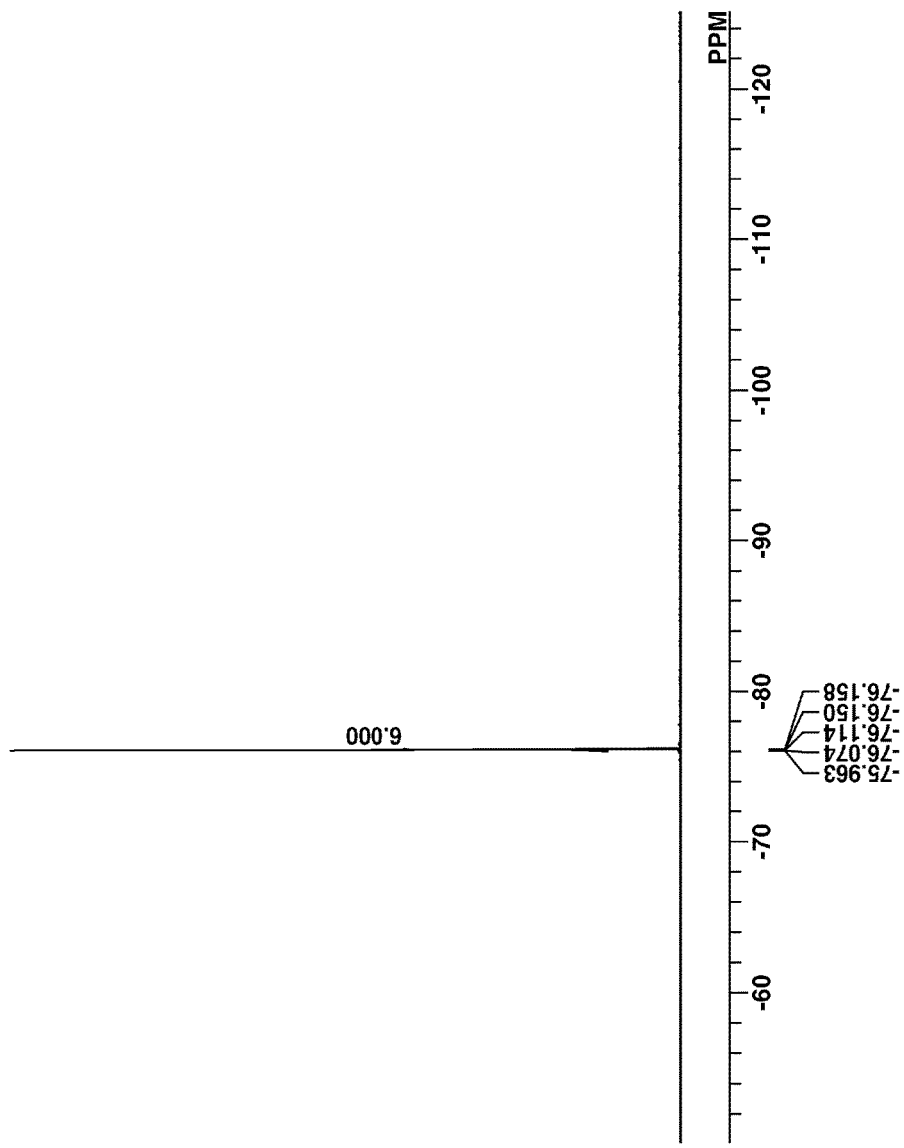

Intermediate B was analyzed by spectroscopy. The NMR spectra, $^1$H- and $^{19}$F-NMR in DMSO-d$_6$ are shown in FIGS. 3 and 4. In $^1$H-NMR analysis, minute amounts of residual solvents (diisopropyl ether, MIBK, water) were observed.

IR (D-ATR): 3091, 3062, 1595, 1579, 1500, 1464, 1445, 1417, 1387, 1316, 1249, 1217, 1185, 1165, 1090, 1068, 1057, 1016, 997, 970, 947, 936, 838, 829, 757, 729, 690, 636, 629, 582, 569, 559 cm$^{-1}$
TOF-MS (MALDI): Positive [M+H]$^+$ 399

Example 1-3

Synthesis of Intermediate C

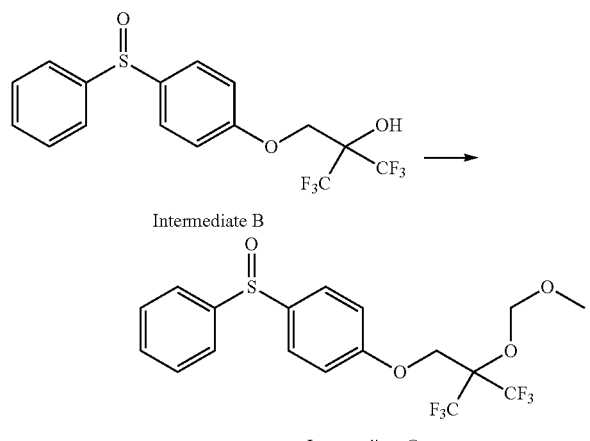

Intermediate B, 117 g, was dissolved in a mixture of 69 g of diisopropylethylamine and 590 g of acetonitrile. Under ice cooling, 36 g of chloromethyl methyl ether was added dropwise to the solution. The solution was aged overnight at room temperature, after which it was combined with 800 g of water and 800 g of toluene, followed by separation. The organic layer was once washed with water, washed with 1 wt % ammonia water, and washed with water again. The solution was further washed with 1 wt % hydrochloric acid and washed with water. The organic layer was taken out and concentrated under reduced pressure. The resulting solid was dried in vacuum, obtaining 127 g of the end compound, Intermediate C as white crystal (yield 82%).

Figure 5:
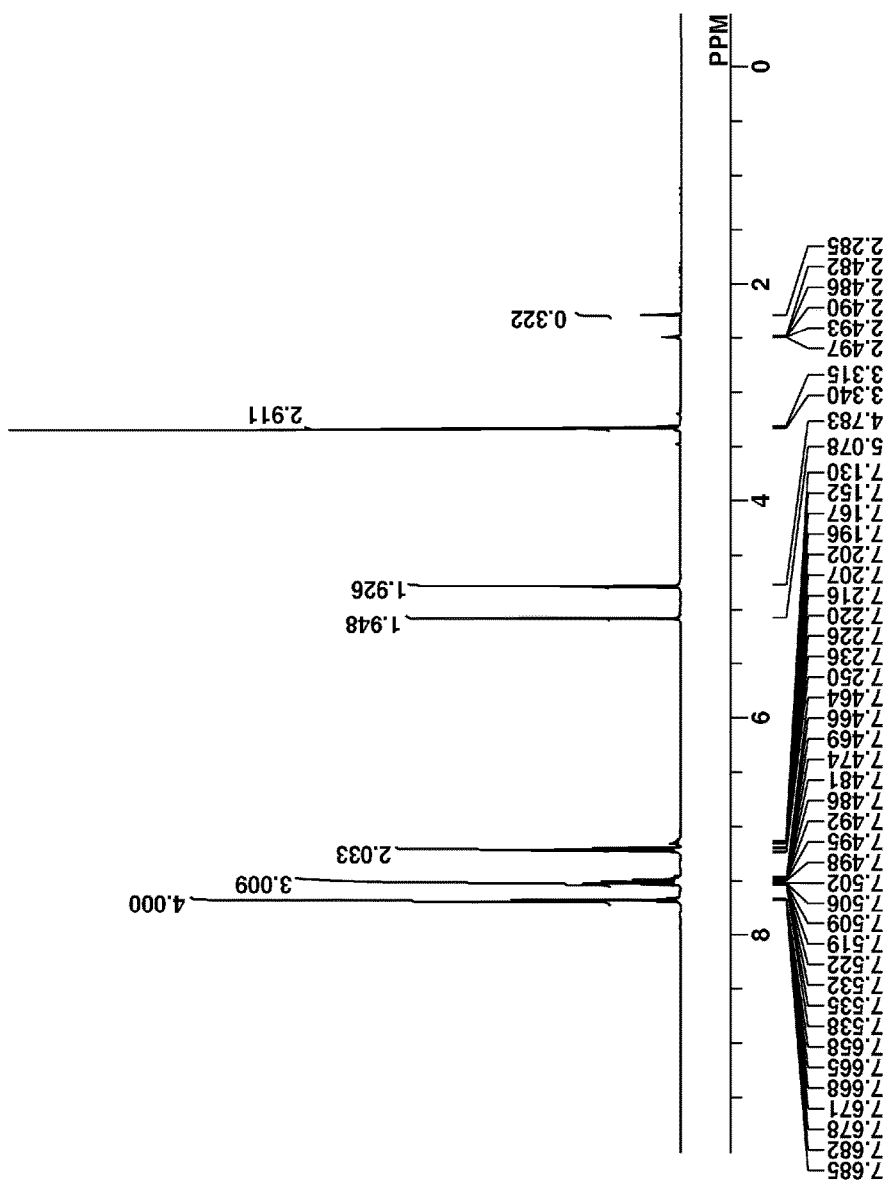
FIGS. 5 and 6 are diagrams showing $^1$H- and $^{19}$F-NMR spectra of the compound of Example 1-3, respectively.
Figure 6:
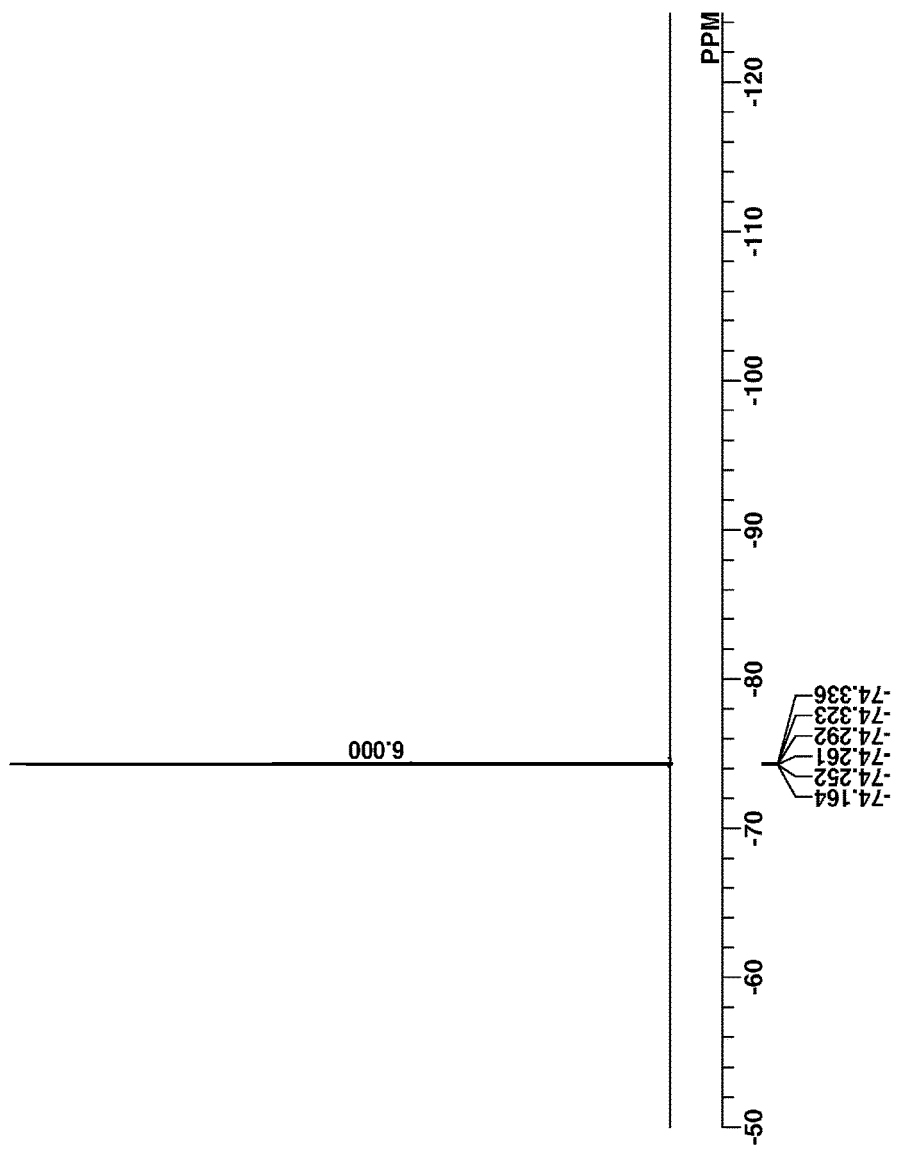

Intermediate C was analyzed by spectroscopy. The NMR spectra, $^1$H- and $^{19}$F-NMR in DMSO-d$_6$ are shown in FIGS. 5 and 6. In $^1$H-NMR analysis, minute amounts of residual solvents (diisopropyl ether, MIBK, water) were observed.

IR (D-ATR): 3467,3065, 2911, 2832, 1593, 1496, 1476, 1444, 1408, 1334, 1284, 1245, 1216, 1152, 1107, 1091, 1079, 1046, 1022, 999, 966, 924, 876, 830, 750, 731, 709, 689, 640, 614, 562 cm$^{-1}$
TOF-MS (MALDI): Positive [M+H]$^+$ 443

Example 1-4

Synthesis of Intermediate D

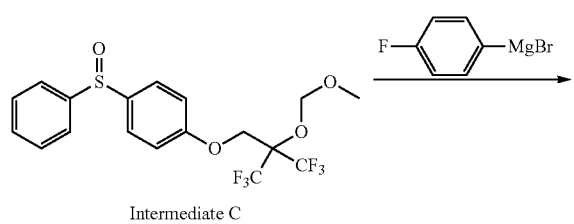

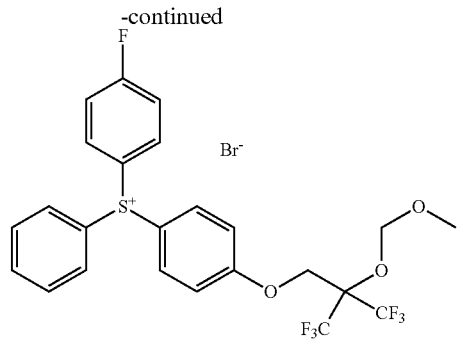

Intermediate C, 127 g, was dissolved in 506 g of THF. To the solution under ice cooling, a Grignard reagent which was separately prepared was added dropwise. Under ice cooling, 93 g of chlorotrimethylsilane was added dropwise to the solution. The solution was aged overnight at room temperature. Under ice cooling, 496 g of 10 wt % ammonium chloride aqueous solution was added to the solution, and 800 g of MIBK and 200 g of water were added thereto. The organic layer containing Intermediate D was separated and transferred to the subsequent reaction.

Example 1-5

Synthesis of Intermediate E

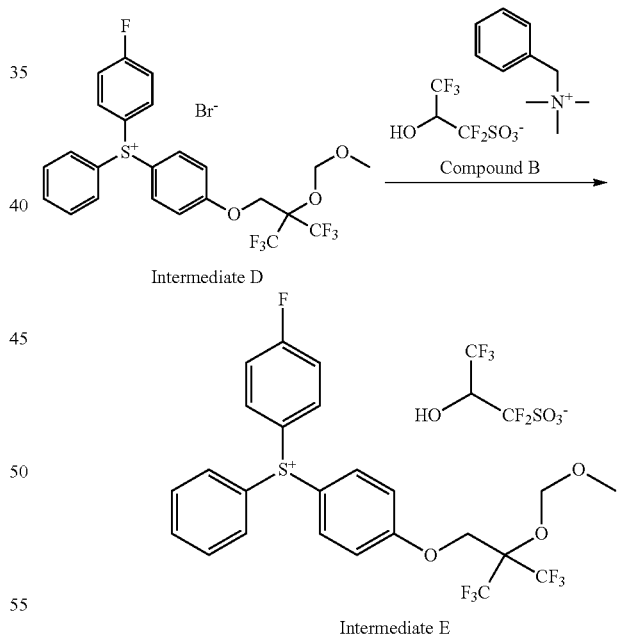

To the organic layer obtained in Example 1-4, 130 g of Compound B and 200 g of water were added, followed by separation. The organic layer was separated, washed 3 times with 2.5 wt % aqueous solution of Compound B, and washed 5 times with deionized water. The organic layer was concentrated under reduced pressure, obtaining an oily product. Diisopropyl ether was added to the product for decantation. This was followed by concentration under reduced pressure, obtaining 204 g of the end compound, Intermediate B (yield 68%).

Figure 7:
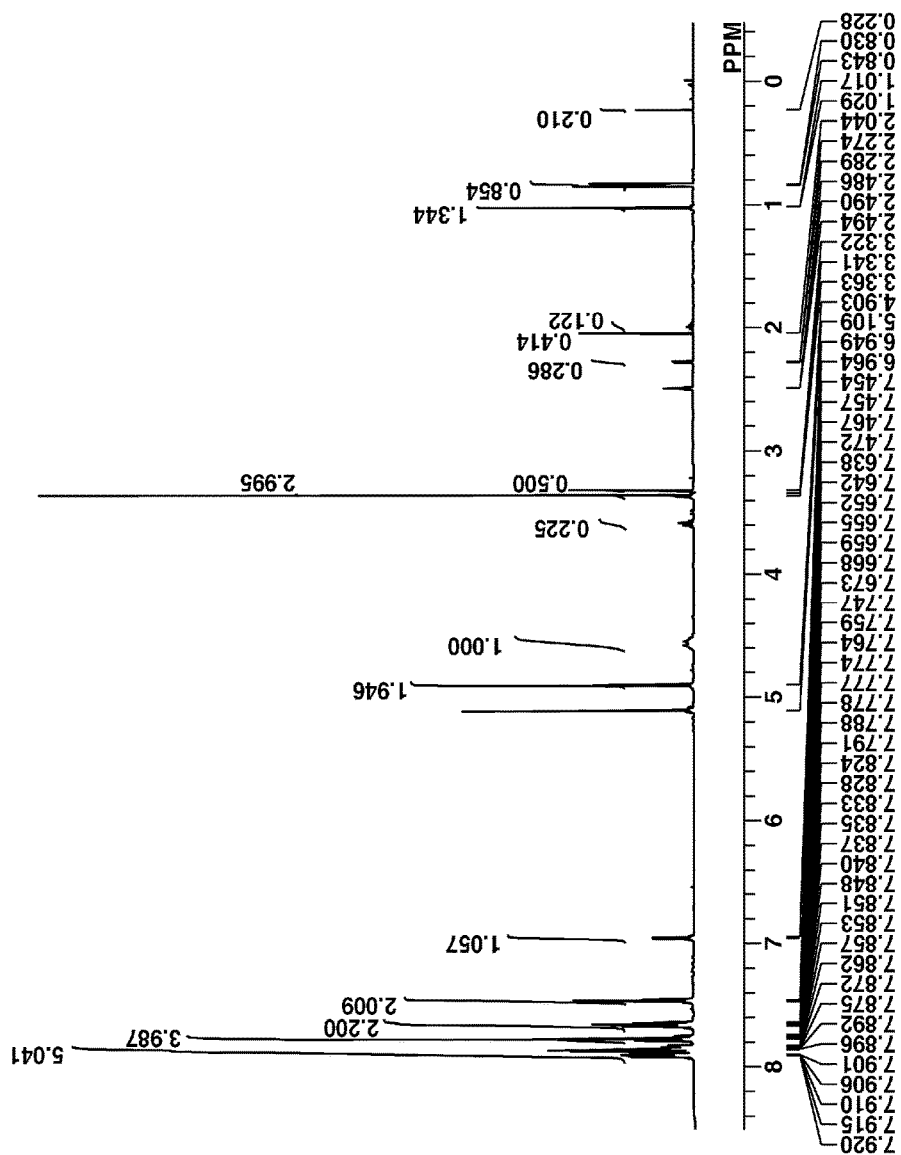
FIGS. 7 and 8 are diagrams showing $^1$H- and $^{19}$F-NMR spectra of the compound of Example 1-5, respectively.
Figure 8:
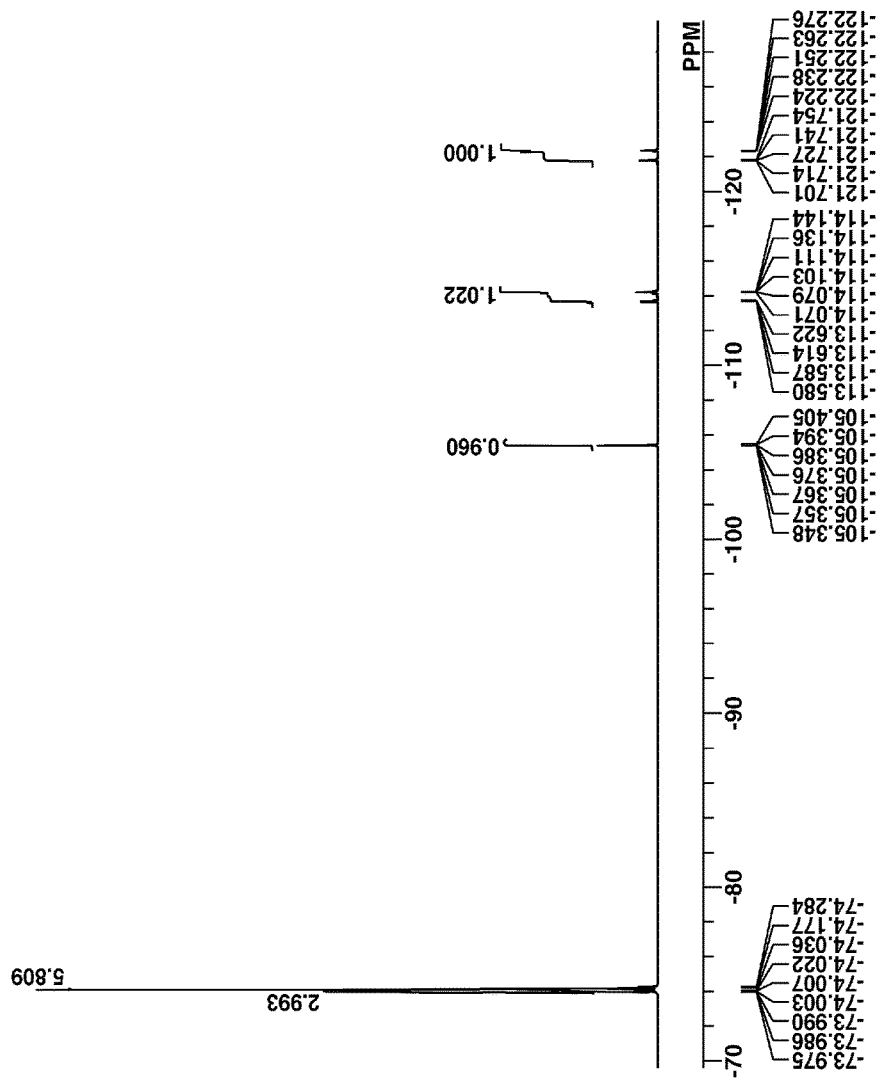

Intermediate E was analyzed by spectroscopy. The NMR spectra, $^1$H- and $^{19}$F-NMR in DMSO-$d_6$ are shown in FIGS. 7 and 8. In $^1$H-NMR analysis, minute amounts of residual solvents (diisopropyl ether, MIBK, water) were observed.

IR (D-ATR): 3280, 3103, 2979, 1589, 1494, 1478, 1448, 1407, 1260, 1228, 1156, 1106, 1072, 989, 966, 924, 836, 750, 732, 685, 644, 560 cm$^{-1}$

TOF-MS (MALDI): Positive M$^+$ 521 (corresponding to $(C_6H_5)(C_4H_4F)(C_6H_4OCH_2CH(CF_3)_2OCH_2OCH_3)S^+$) Negative M$^-$ 229 (corresponding to $CCF_3(OH)CF_2SO_3^-$)

Example 1-6

Synthesis of Sulfonium Compound A

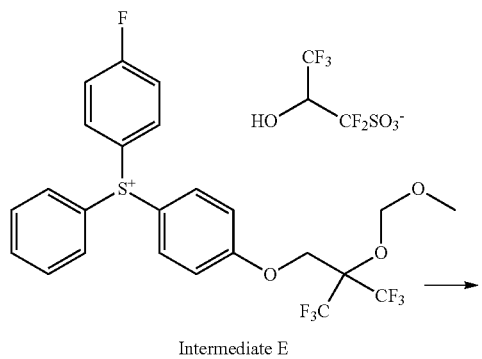

Intermediate E

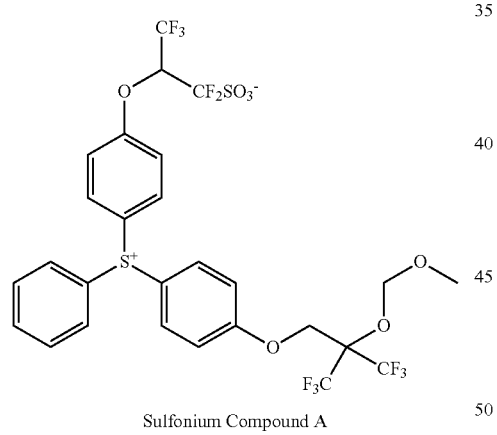

Sulfonium Compound A

A solution of 2.5 g of sodium hydride in 125 g of THF was added dropwise to a solution of 45 g of Intermediate E in 121 g of THF below 5° C. The solution was aged overnight at room temperature, after which water was added below 5° C. MIBK, 300 g was added to the solution, followed by separation. The organic layer was separated and washed with water, then washed with 1 wt % hydrochloric acid, and washed with water again. The organic layer was separated and concentrated under reduced pressure, obtaining an oily product. Diisopropyl ether was added to the product for decantation. The solid was filtered and dried in vacuum, obtaining 39 g of Sulfonium Compound A as white crystal (yield 58%).

Figure 9:
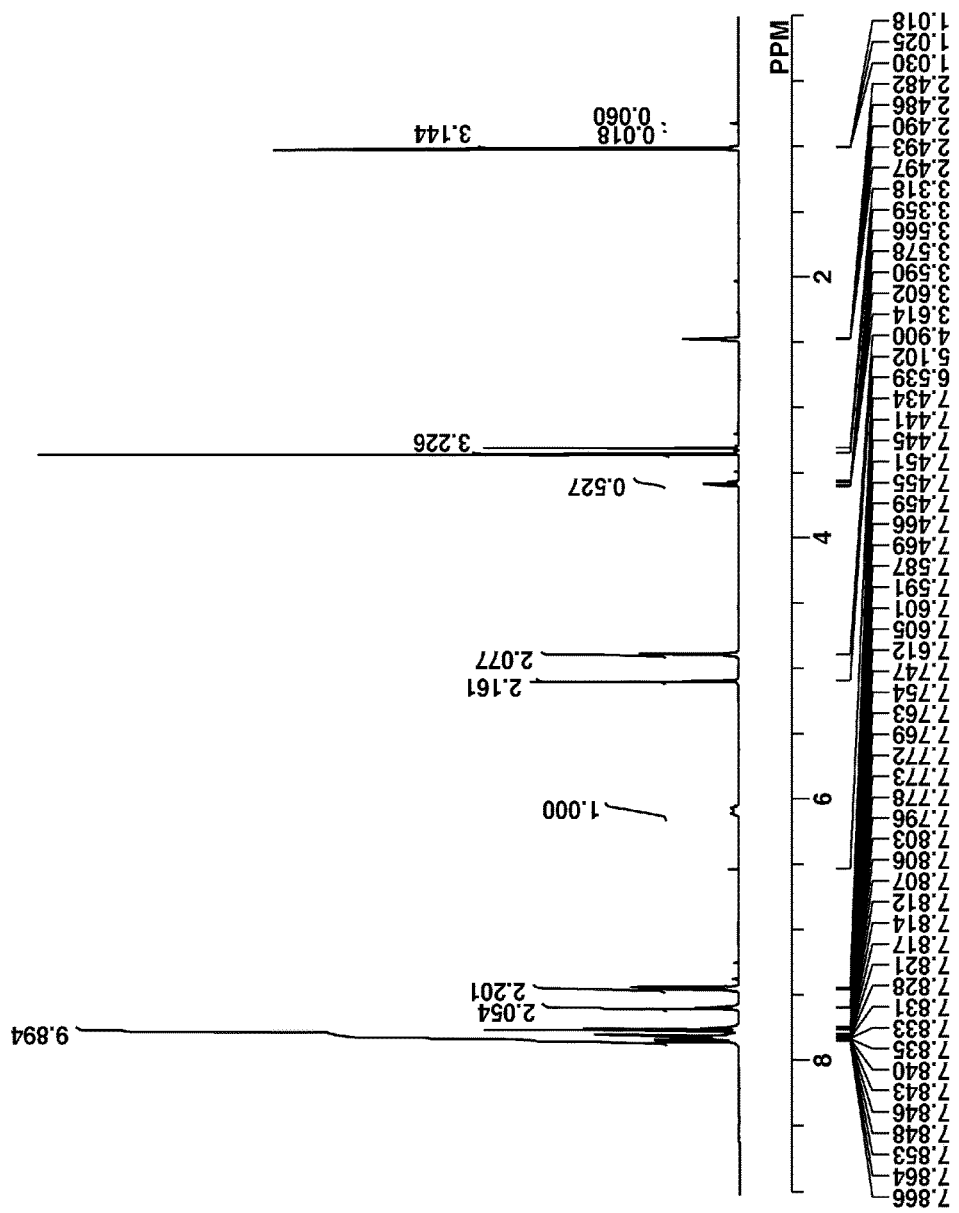
FIGS. 9 and 10 are diagrams showing $^1$H- and $^{19}$F-NMR spectra of the compound of Example 1-6, respectively.
Figure 10:
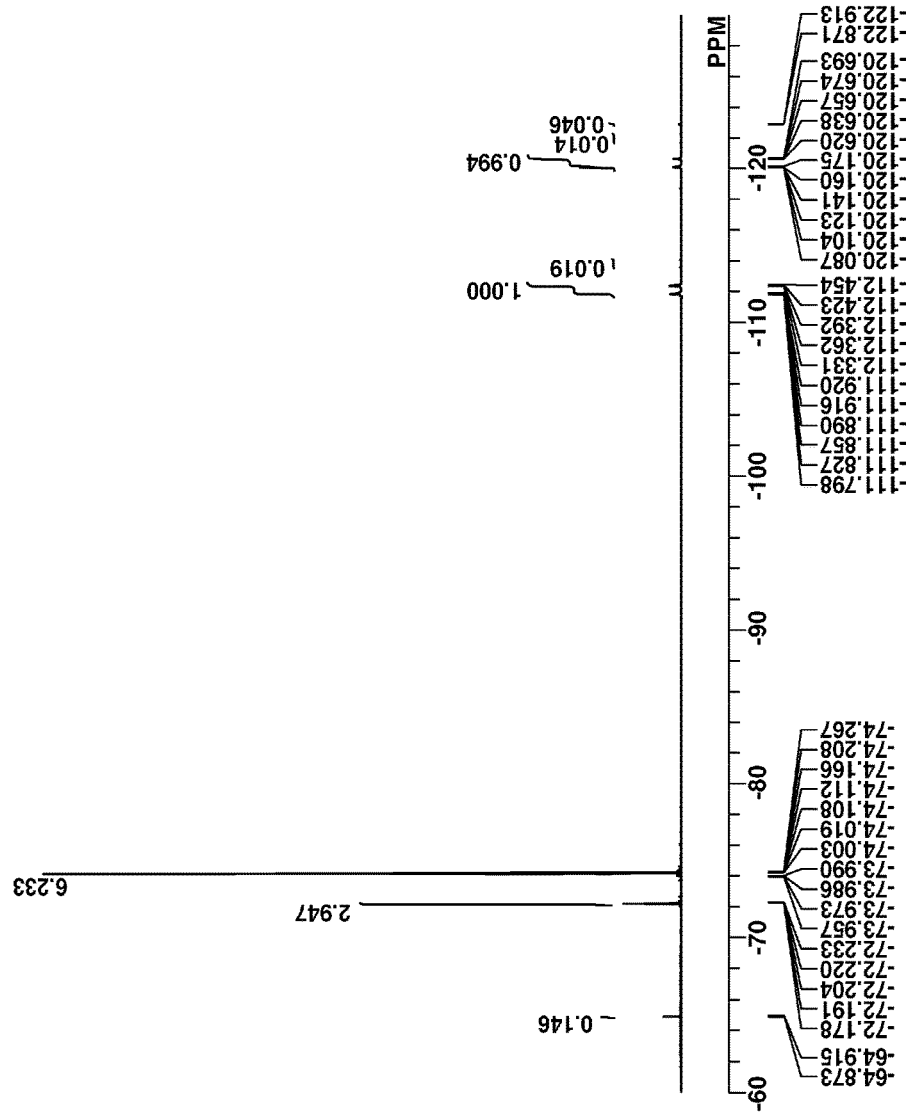

Sulfonium Compound A was analyzed by spectroscopy. The NMR spectra, $^1$H- and $^{19}$F-NMR in DMSO-d6 are shown in FIGS. 9 and 10. In $^1$H-NMR analysis, minute amounts of residual solvents (diisopropyl ether, water) were observed.

IR (D-ATR): 3511, 3100, 2981, 1588, 1494, 1448, 1417, 1248, 1183, 1154, 1106, 1073, 996, 966, 924, 884, 834, 750, 732, 685, 642, 584 cm$^{-1}$

TOF-MS (MALDI): [M] 731

2) Synthesis of Polymers

Polymers for use in resist compositions were synthesized according to the following formulation. Mw is measured by GPC versus polystyrene standards using THF solvent.

Synthesis Example 1

Synthesis of Polymer P1

In a flask under nitrogen atmosphere, 22 g of 1-t-butyl-cyclopentyl methacrylate, 17 g of 2-oxotetrahydrofuran-3-yl methacylate, 0.48 g of dimethyl 2,2'-azobis(2-methylpropionate) (V-601 by Wako Pure Chemical Industries, Ltd.), 0.41 g of 2-mercaptoethanol, and 50 g of MEK were combined to form a monomer/initiator solution. Another flask in nitrogen atmosphere was charged with 23 g of MEK, which was heated at 80° C. with stirring. With stirring, the monomer/initiator solution was added dropwise to the flask over 4 hours. After the completion of dropwise addition, the polymerization solution was continuously stirred for 2 hours while maintaining the temperature of 80° C. The polymerization solution was cooled to room temperature, whereupon it was added dropwise to 640 g of methanol with vigorous stirring. The precipitate was collected by filtration, washed twice with 240 g of methanol, and vacuum dried at 50° C. for 20 hours, obtaining 36 g of a copolymer (Polymer P1) in white powder form (yield 90%). On GPC analysis, Polymer P1 had a Mw of 8,755 and a dispersity Mw/Mn of 1.94.

Polymer P1

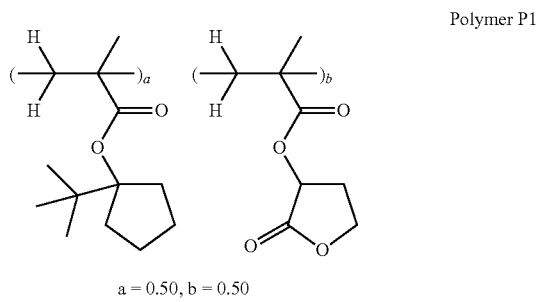

a = 0.50, b = 0.50

Synthesis Examples 2 to 10

Synthesis of Polymers P2 to P10

Polymers were synthesized by the same procedure as in Synthesis Example 1 aside from changing the type and amount of monomers. Table 1 shows the proportion (in molar ratio) of units incorporated in these polymers. The structure of recurring units is shown in Tables 2 and 3.

TABLE 1
| | | Polymer | Unit 1 (molar ratio) | Unit 2 (molar ratio) | Unit 3 (molar ratio) | Unit 4 (molar ratio) | MW | MW/Mn |
|---|---|---|---|---|---|---|---|---|
| Synthetic Example | 1 | P1 | A-1 (0.50) | B-1 (0.50) | — | — | 8,755 | 1.94 |
| | 2 | P2 | A-2 (0.50) | B-1 (0.50) | — | — | 8,100 | 1.90 |
| | 3 | P3 | A-3 (0.50) | B-1 (0,50) | — | — | 7,700 | 1.91 |
| | 4 | P4 | A-2 (0.40) | B-1 (0.50) | B-2 (0.10) | — | 9,000 | 1.85 |
| | 5 | P5 | A-4 (0.40) | B-1 (0.60) | — | — | 7,500 | 1.93 |
| | 6 | P6 | A-4 (0.40) | B-3 (0.60) | — | — | 8,300 | 1.87 |
| | 7 | P7 | A-3 (0.30) | A-4 (0.20) | B-1 (0.40) | B-4 (0.10) | 7,200 | 1.86 |
| | 8 | P8 | A-3 (0.30) | A-4 (0.20) | B-2 (0.40) | B-4 (0.10) | 8,900 | 1.95 |
| | 9 | P9 | A-3 (0.25) | A-6 (0.25) | B-1 (0.35) | B-4 (0.15) | 8,300 | 1.78 |
| | 10 | P10 | A-5 (0.40) | B-3 (0.50) | B-4 (0.10) | — | 6,300 | 2.00 |
TABLE 2
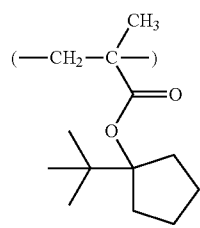
A-1
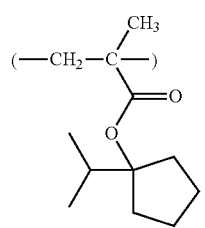
A-2
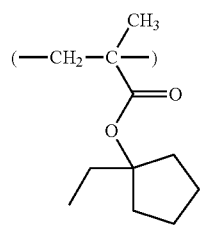
A-3
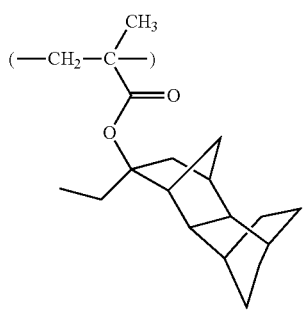
A-4
TABLE 2-continued
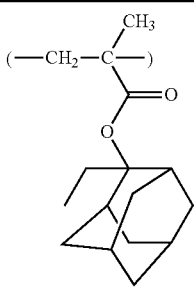
A-5
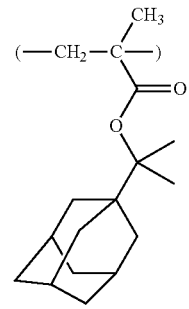
A-6
TABLE 3
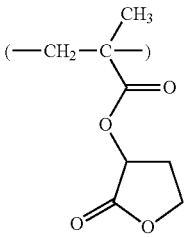
B-1
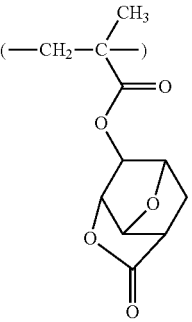
B-2

TABLE 3-continued

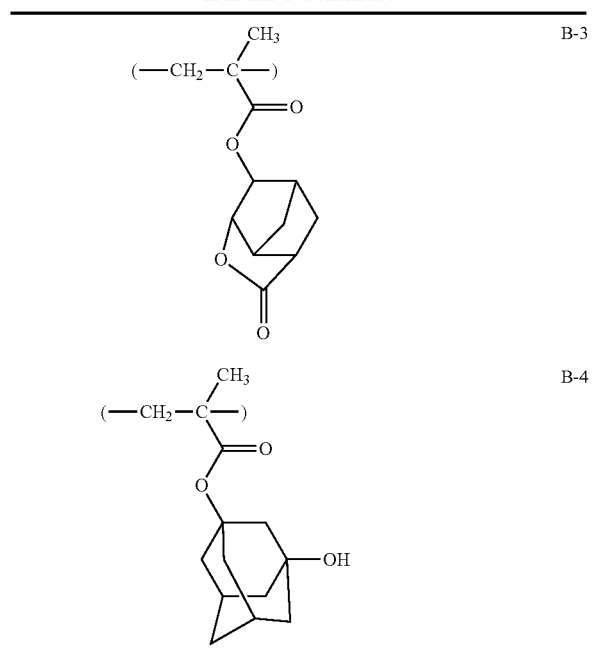

3) Preparation of Resist Composition

Examples 2-1 to 2-12 and Comparative Examples 1-1 to 1-4

Resist compositions in solution form were prepared by dissolving Sulfonium Compound A, polymer, quencher, alkali-soluble surfactant (SF-1), and optionally a second PAG in an organic solvent containing 0.01 wt % of surfactant A in accordance with the formulation shown in Table 4, and filtering through a Teflon® filter with a pore size of 0.2 μm. In Comparative Examples, resist compositions free of Sulfonium Compound A were prepared.

The solvent, quencher, second PAG, alkali-soluble surfactant (SF-1) and surfactant A used herein are identified below.

Solvent:
  POMEA=propylene glycol monomethyl ether acetate
  GBL=γ-butyrolactone Second PAG:
  PAG-X: triphenylsulfonium 2-(adamantane-1-carbonyloxy)-1,1,3,3,3-pentafluoropropane-1-sulfonate
  PAG-Y: compound of the following formula (prepared with reference to Patent Document 5)

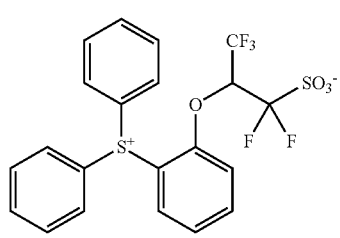
(PAG-Y)

Quencher:
  Q-A: 2-(4-morpholinyl)ethyl laurate
  Q-B: triphenylsulfonium salicylate Alkali-Soluble Surfactant (SF-1):
  compound described in JP-A 2008-122932, poly(3,3,3-trifluoro-2-hydroxy-1,1-dimethyl-2-trifluoromethyl-propyl methacrylate/1,1,1-trifluoro-2-hydroxy-6-methyl-2-trifluoromethylhept-4-yl methacrylate)
  Mw=7,300
  Mw/Mn=1.86

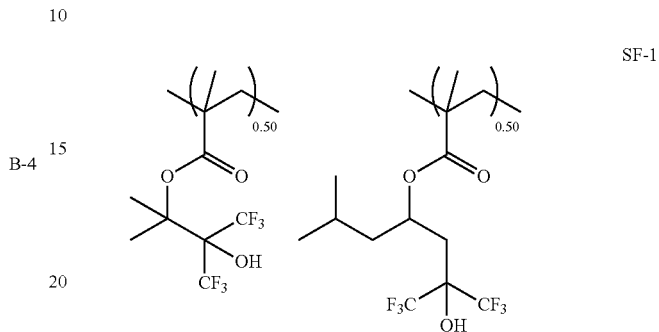
SF-1

Surfactant A:
  3-methyl-3-(2,2,2-trifluoroethoxymethyl)oxetane/tetrahydrofuran/2,2-dimethyl-1,3-propanediol copolymer (Omnova Solutions, Inc.)

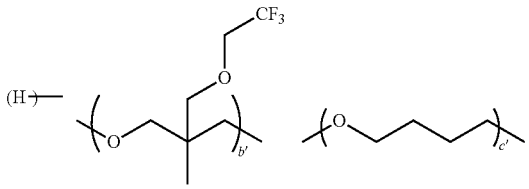

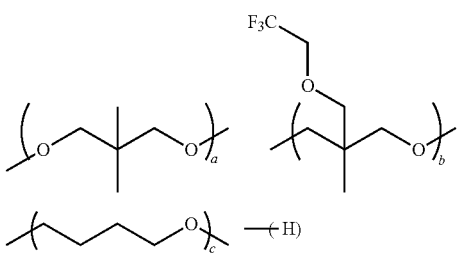

a:(b+b'):(c+c')=1:4-7:0.01-1 (molar ratio)
Mw=1,500

TABLE 4

|  |  | Resist composition | Polymer (pbw) | PAG (pbw) | Quencher (pbw) | Surfactant (pbw) | Solvent 1 (pbw) | Solvent 2 (pbw) |
|---|---|---|---|---|---|---|---|---|
| Example | 2-1 | R1 | P1 (80) | Sulfonium Compound A (11.3) | Q-A (1.3) | SF-1 (3.0) | PGMEA (1,728) | GBL (192) |
|  | 2-2 | R2 | P2 (80) | Sulfonium Compound A (11.3) | Q-A (1.3) | SF-1 (3.0) | PGMEA (1,728) | GBL (192) |
|  | 2-3 | R3 | P3 (80) | Sulfonium Compound A (11.3) | Q-A (1.3) | SF-1 (3.0) | PGMEA (1,728) | GBL (192) |
|  | 2-4 | R4 | P4 (80) | Sulfonium Compound A (11.3) | Q-A (1.3) | SF-1 (3.0) | PGMBA (1,728) | GBL (192) |
|  | 2-5 | R5 | P5 (80) | Sulfonium Compound A (11.3) | Q-A (1.3) | SF-1 (3.0) | PGMEA (1,728) | GBL (192) |
|  | 2-6 | R6 | P6 (80) | Sulfornium Compound A (11.3) | Q-A (1.3) | SF-1 (3.0) | PGMEA (1,728) | GBL (192) |
|  | 2-7 | R7 | P7 (80) | Sulfornum Compound A (11.3) | Q-A (1.3) | SF-1 (3.0) | PGMEA (1,728) | GBL (192) |
|  | 2-8 | R8 | P8 (80) | Sulfonium Compound A (11.3) | Q-A (1.3) | SF-1 (3.0) | PGMEA (1,728) | GBL (192) |
|  | 2-9 | R9 | P9 (80) | Sulfonium Compound A (11.3) | Q-A (1.3) | SF-1 (3.0) | PGMEA (1,728) | GBL (192) |
|  | 2-10 | R10 | P10 (80) | Sulfonium Compound A (11.3) | Q-A (1.3) | SF-1 (3.0) | PGMEA (1,728) | GBL (192) |
|  | 2-11 | R11 | P1 (80) | Sulfonium Compound A (11.3) | Q-B (3.1) | SF-1 (3.0) | PGMEA (1,728) | GBL (192) |
|  | 2-12 | R12 | P1 (80) | Sulfonium Compound A (5.7) PAG-X (5.1) | Q-A (1.3) | SF-1 (3.0) | PGMBA (1,728) | GBL (192) |
| Comparative Example | 1-1 | R13 | P1 (80) | PAG-X (7.6) | Q-A (1.3) | SF-1 (3.0) | PGMEA (1,728) | GEL (192) |
|  | 1-2 | R14 | P1 (80) | PAG-Y (7.6) | Q-A (1.3) | SF-1 (3.0) | PGMEA (1,728) | GEL (192) |
|  | 1-3 | R15 | P2 (80) | PAG-X (7.6) | Q-B (3.1) | SF-1 (3.0) | PGMEA (1,728) | GEL (192) |
|  | 1-4 | R16 | P2 (80) | PAG-Y (7.6) | Q-B (3.1) | SF-1 (3.0) | PGMEA (1,728) | GEL (192) |

4) ArF Lithography Test #1

Examples 3-1 to 3-12 and Comparative Examples 2-1 to 2-4

On a silicon substrate, an antireflective coating solution ARC-29A (Nissan Chemical Industries Ltd.) was coated and baked at 200° C. for 60 seconds to form an ARC film of 100 nm thick. On this substrate, each of the resist compositions (R1 to R16) was spin coated and baked on a hotplate at 100° C. for 60 seconds to form a resist film of 90 nm thick. Using an ArF immersion lithography scanner (NSR-610C by Nikon Corp., NA 1.30, dipole illumination, Cr mask), the resist film was exposed by ArF excimer laser immersion lithography. Water was used as the immersion liquid. The resist film was baked (PEB) at the temperature shown in Table 5 for 60 seconds and developed in a 2.38 wt % TMAH aqueous solution for 60 seconds.

Evaluation of Sensitivity

The 40-nm 1:1 line-and-space pattern was observed under an electron microscope. The optimum dose (Eop) was a dose (mJ/cm$^2$) which provided a line width of 40 nm. The pattern printed at the optimum dose was observed to judge whether or not its profile was acceptable.

Evaluation of line Width Roughness (LWR)

The width of lines of a 40-nm 1:1 line-and-space pattern was measured under SEM to determine a line width variation (30 points measured, 30 value computed), which was reported as LWR. A smaller value of LWR indicates a line pattern with a less fluctuation and of better profile.

Evaluation of Collapse Limit

The collapse limit was a minimum width (nm) of lines which could be resolved without collapse when the line width was reduced by increasing the exposure dose. A smaller value indicates better collapse resistance.

Evaluation of Depth-of-focus (DOF)

A focus range where a IS pattern could be resolved at the optimum dose was determined and reported as depth of focus (DOF, nm). A larger value of DOF indicates a wider permissible margin for focus offset and is preferable.

The results are shown in Table 5.

TABLE 5

|  |  | Resist composition | PEB temp. (° C.) | Eop (mJ/cm$^2$) | LWR (nm) | Collapse limit (nm) | DOF (nm) |
|---|---|---|---|---|---|---|---|
| Example | 3-1 | R1 | 75 | 32 | 2.9 | 30 | 75 |
|  | 3-2 | R2 | 80 | 34 | 2.6 | 29 | 70 |
|  | 3-3 | R3 | 90 | 36 | 2.7 | 31 | 65 |
|  | 3-4 | R4 | 80 | 35 | 2.7 | 32 | 70 |
|  | 3-5 | R5 | 85 | 33 | 2.8 | 33 | 70 |
|  | 3-6 | R6 | 85 | 34 | 2.5 | 32 | 65 |
|  | 3-7 | R7 | 95 | 37 | 2.4 | 31 | 75 |
|  | 3-8 | R8 | 95 | 36 | 2.7 | 29 | 75 |
|  | 3-9 | R9 | 110 | 39 | 2.9 | 34 | 65 |
|  | 3-10 | R10 | 105 | 38 | 2.8 | 34 | 70 |
|  | 3-11 | R11 | 75 | 33 | 2.6 | 28 | 75 |
|  | 3-12 | R12 | 75 | 34 | 2.7 | 29 | 70 |
| Comparative Example | 2-1 | R13 | 75 | 31 | 3.2 | 42 | 45 |
|  | 2-2 | R14 | 75 | 34 | 3.6 | 40 | 30 |
|  | 2-3 | R15 | 80 | 33 | 3.3 | 42 | 40 |
|  | 2-4 | R16 | 80 | 36 | 3.8 | 42 | 35 |

It is evident from Table 5 that the inventive resist composition is suited for the ArF immersion lithography because a pattern with high resolution and reduced LWR is formed.

5) ArF Lithography Test #2

Examples 4-1 to 4-12 and Comparative Examples 3-1 to 3-4

On a substrate, a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, each of the resist compositions (R1 to R16) was spin coated, then baked on a hotplate at 100° C. for 60 seconds to form a resist film of 100 nm thick. Using an ArF excimer laser immersion lithography scanner NSR-610C (Nikon Corp., NA 1.30, σ 0.98/0.78, 4/5 annular illumination), pattern exposure was performed through Mask A or B described below. Water was used as the immersion liquid.

Mask A is a 6% halftone phase shift mask bearing a line pattern with a pitch of 100 nm and a line width of 50 nm (on-wafer size). After exposure through Mask A, the wafer was baked (PEB) at an arbitrary temperature for 60 seconds and developed. Specifically, butyl acetate was injected from a development nozzle while the wafer was spun at 30 rpm for 3 seconds, which was followed by stationary puddle development for 27 seconds. As a result, the unexposed regions which had been masked with Mask A were dissolved in the developer, that is, image reversal took place to form a line-and-space (L/S) pattern with a space width of 50 nm and a pitch of 100 nm.

Mask B is a 6% halftone phase shift mask bearing a line pattern with a pitch of 200 nm and a line width of 45 nm (on-wafer size). After exposure through Mask B, the wafer was baked (PEB) at an arbitrary temperature for 60 seconds and developed. Specifically, butyl acetate was injected from a development nozzle while the wafer was spun at 30 rpm for 3 seconds, which was followed by stationary puddle development for 27 seconds. As a result, the unexposed regions which had been masked with Mask B were dissolved in the developer, that is, image reversal took place to form an isolated space pattern (referred to as "trench pattern", hereinafter) with a space width of 45 nm and a pitch of 200 nm.

Evaluation of Sensitivity

As an index of sensitivity, the optimum dose (Eop, mJ/cm$^2$) which provided an L/S pattern with a space width of 50 nm and a pitch of 100 nm on exposure through Mask A was determined.

Evaluation of LWR

The L/S pattern formed by exposure in the optimum dose (determined in the sensitivity evaluation) through Mask A was observed under TDSEM S-9380 (Hitachi High-Technologies Corp.). The space width was measured at longitudinally spaced apart points, from which a 3-fold value (3σ) of standard deviation (σ) was determined and reported as LWR. A smaller value indicates a pattern having a less roughness and more uniform space width.

Evaluation of DOF Margin

The exposure dose and DOF which ensured to form a trench pattern with a space width of 35 nm on exposure through Mask B were defined as the optimum exposure dose and the optimum DOF, respectively. The depth (μm) over which focus was changed that could form a resist pattern with a space width of 35 nm±10% (i.e., 31.5 nm to 38.5 nm) was determined and reported as DOF. A larger value indicates a smaller change of pattern size with a change of DOF and hence, better DOF margin.

Evaluation of Collapse Limit

In the process of forming a trench pattern using Mask B, as the exposure dose is reduced, the trench size is enlarged and the line size is reduced. The maximum of trench width below which lines can be resolved without collapse is determined and reported as collapse limit (nm). A higher value indicates greater collapse resistance and is preferable.

The results are shown in Table 6.

TABLE 6

| | | Resist composition | PEB temp. (° C.) | Eop (mJ/cm$^2$) | LWR (nm) | Collapse limit (nm) | DOF margin (nm) |
|---|---|---|---|---|---|---|---|
| Example | 4-1 | R1 | 75 | 33 | 3.7 | 56 | 150 |
| | 4-2 | R2 | 80 | 35 | 3.6 | 57 | 140 |
| | 4-3 | R3 | 90 | 36 | 3.9 | 55 | 130 |
| | 4-4 | R4 | 80 | 34 | 3.7 | 57 | 140 |
| | 4-5 | R5 | 85 | 33 | 3.6 | 55 | 130 |
| | 4-6 | R6 | 85 | 33 | 3.8 | 53 | 130 |
| | 4-7 | R7 | 95 | 36 | 3.5 | 56 | 140 |
| | 4-8 | R8 | 95 | 37 | 3.4 | 38 | 150 |
| | 4-9 | R9 | 110 | 39 | 3.8 | 54 | 140 |
| | 4-10 | R10 | 105 | 39 | 3.9 | 54 | 130 |
| | 4-11 | R11 | 75 | 33 | 3.4 | 56 | 150 |
| | 4-12 | R12 | 75 | 35 | 3.3 | 56 | 150 |
| Comparative Example | 3-1 | R13 | 75 | 33 | 5.0 | 36 | 100 |
| | 3-2 | R14 | 75 | 32 | 5.3 | 32 | 90 |
| | 3-3 | R15 | 80 | 35 | 5.2 | 34 | 100 |
| | 3-4 | R16 | 80 | 34 | 5.6 | 31 | 90 |

As seen from the results of Table 6, the resist compositions within the scope of the invention form negative patterns via organic solvent development with the advantages of improved LWR, improved DOF margin of trench patterns, and better collapse limit. That is, resolution is improved. Thus the compositions are advantageously applicable to the organic solvent development process.

Japanese Patent Application No. 2016-169793 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A sulfonium compound having the formula (1A), (1B) or (1C):

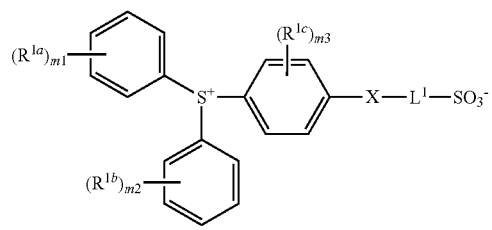

(1A)

-continued (1B)

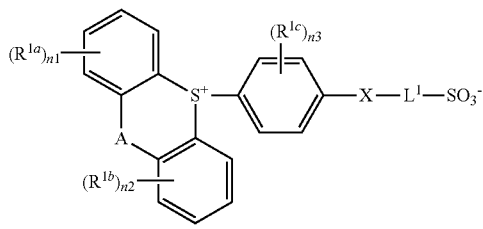

(1C)

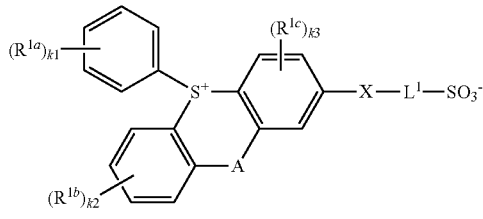

wherein $L^1$ is a $C_1$-$C_{20}$ straight, branched or cyclic divalent hydrocarbon group which may contain a heteroatom-containing radical, X is a divalent linking group, A is a single bond, methylene group, carbonyl group, sulfinyl group, sulfonyl group, amino group, ether bond, thioether bond, ester bond, carbonate bond, carbamate bond or sulfonic acid ester bond, $R^{1a}$ to $R^{1c}$ are each independently a $C_1$-$C_{20}$ straight, branched or cyclic monovalent hydrocarbon group which may contain a heteroatom-containing radical, at least one of $R^{1a}$ to $R^{1c}$ being a group having the formula (2) shown below, with the proviso that where at least two groups $R^{1a}$ are included, two of them may bond together to from a ring with the carbon atoms on the benzene ring to which they are attached, where at least two groups $R^{1b}$ are included, two of them may bond together to from a ring with the carbon atoms on the benzene ring to which they are attached, and where at least two groups $R^{1c}$ are included, two of them may bond together to from a ring with the carbon atoms on the benzene ring to which they are attached, m1, m2 and m3 are integers meeting $0 \leq m1 \leq 5$, $0 \leq m2 \leq 5$, $0 \leq m3 \leq 4$, and $m1+m2+m3 \geq 1$, n1, n2 and n3 are integers meeting $0 \leq n1 \leq 4$, $0 \leq n2 \leq 4$, $0 \leq n3 \leq 4$, and $n1+n2+n3 \geq 1$, k1, k2 and k3 are integers meeting $0 \leq k1 \leq 5$, $0 \leq k2 \leq 4$, $0 \leq k3 \leq 3$, and $k1+k2+k3 \geq 1$, (2)

wherein $L^2$ is a $C_1$-$C_{20}$ straight, branched or cyclic divalent hydrocarbon group which may contain a heteroatom-containing radical, $R^2$ is an acid-eliminatable group, $R^{f1}$ and $R^{f2}$ are each independently hydrogen, $C_1$-$C_{20}$ straight, branched or cyclic alkyl group, fluorine, or $C_1$-$C_{20}$ straight, branched or cyclic fluoroalkyl group, at least one of $R^{f1}$ and $R^{f2}$ being fluorine or fluoroalkyl, and the broken line designates a valence bond.

2. The sulfonium compound of claim 1 wherein $R^{f1}$ and $R^{f2}$ each are trifluoromethyl.

3. The sulfonium compound of claim 1, having the formula (3A), (3B) or (3C):

(3A)

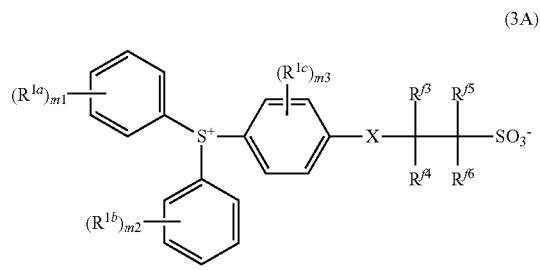

(3B)

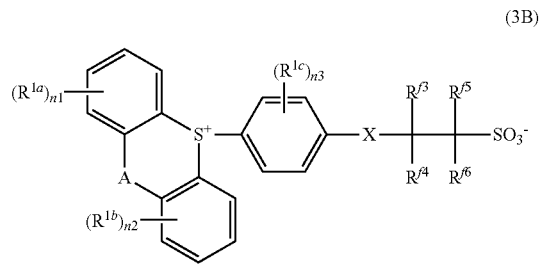

(3C)

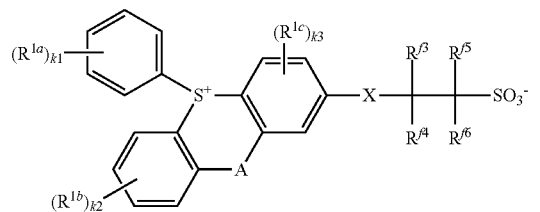

wherein $R^{1a}, R^{1b}, R^{1c}$, X, A, m1, m2, m3, n1, n2, n3, k1, k2, and k3 are as defined above, $R^{f3}, R^{f4}, R^{f5}$ and $R^{f6}$ are each independently hydrogen, fluorine or trifluoromethyl.

4. The sulfonium compound of claim 3 wherein $R^{f5}$ and $R^{f6}$ each are fluorine.

5. A photoacid generator comprising the sulfonium compound of claim 1.

6. A resist composition comprising the photoacid generator of claim 5.

7. The resist composition of claim 6, further comprising a base resin containing a polymer comprising recurring units having the formula (a) and recurring units having the formula (b):

(a)

-continued

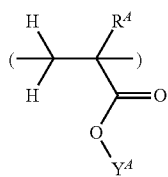
(b)

wherein $R^A$ is hydrogen, fluorine, methyl or trifluoromethyl, $Z^A$ is a single bond, phenylene group, naphthylene group or (backbone)-C(=O)—O—Z'—, Z' is a $C_1$-$C_{10}$ straight, branched or cyclic alkylene group which may contain a hydroxyl radical, ether bond, ester bond or lactone ring, or phenylene group or naphthylene group, $X^A$ is an acid labile group, and $Y^A$ is hydrogen or a polar group having at least one structure selected from the group consisting of hydroxyl, cyano, carbonyl, carboxyl, ether bond, ester bond, sulfonic acid ester bond, carbonate bond, lactone ring, sultone ring and carboxylic anhydride.

8. The resist composition of claim 6, further comprising an organic solvent.

9. The resist composition of claim 6, further comprising other photoacid generator.

10. The resist composition of claim 9 wherein the other photoacid generator has the formula (5) or (6):

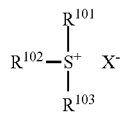
(5)

wherein $R^{101}$, $R^{102}$ and $R^{103}$ are each independently a $C_1$-$C_{20}$ straight, branched or cyclic monovalent hydrocarbon group which may contain a heteroatom, any two of $R^{101}$, $R^{102}$ and $R^{103}$ may bond together to form a ring with the sulfur atom to which they are attached, X⁻ is an anion selected from the formulae (5A) to (5D):

(5A)

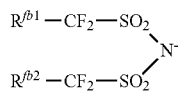
(5B)

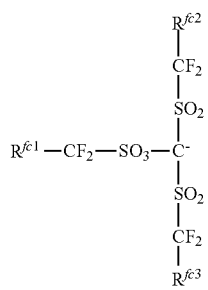
(5C)

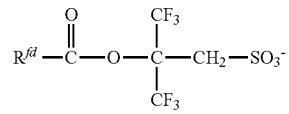
(5D)

wherein $R^{fa}$, $R^{fb1}$, $R^{fb2}$, $R^{fc1}$, $R^{fc2}$ and $R^{fc3}$ are each independently fluorine or a $C_1$-$C_{40}$ straight, branched or cyclic monovalent hydrocarbon group which may contain a heteroatom, or a pair of $R^{fb1}$ and $R^{fb2}$, or $R^{fc1}$ and $R^{fc2}$ may bond together to form a ring with the carbon atoms to which they are attached and any intervening atoms, $R^{fd}$ is a $C_1$-$C_{40}$ straight, branched or cyclic monovalent hydrocarbon group which may contain a heteroatom,

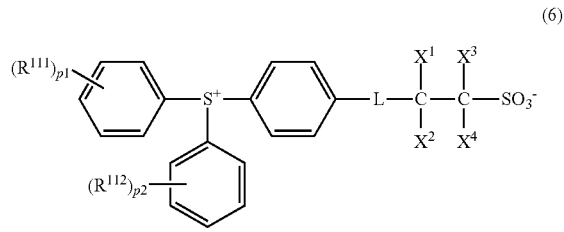
(6)

wherein $R^{111}$ and $R^{112}$ are each independently a $C_1$-$C_{20}$ straight, branched or cyclic alkyl group, p1 and p2 are each independently an integer of 0 to 5, L is a single bond, ether bond, or a $C_1$-$C_{20}$ straight, branched or cyclic divalent hydrocarbon group which may contain a heteroatom, $X^1$, $X^2$, $X^3$ and $X^4$ are each independently hydrogen, fluorine or trifluoromethyl, at least one of $X^1$, $X^2$, $X^3$ and $X^4$ being a substituent group other than hydrogen.

11. The resist composition of claim 6, further comprising an onium salt having the formula (7) or (8):

(7)

(8)

wherein $R^{151}$ and $R^{152}$ are each independently hydrogen or a $C_1$-$C_{40}$ straight, branched or cyclic monovalent hydrocarbon group which may contain a heteroatom, excluding the hydrocarbon group in which the hydrogen atom bonded to the carbon at α-position relative to the sulfo group is substituted by fluorine or fluoroalkyl, and M⁺ is an onium cation.

12. The resist composition of claim 6, further comprising an amine compound.

13. The resist composition of claim 6, further comprising a surfactant which is insoluble or substantially insoluble in water and soluble in alkaline developer, and/or a surfactant which is insoluble or substantially insoluble in water and alkaline developer.

14. A pattern forming process comprising the steps of applying the resist composition of claim 6 onto a substrate, prebaking to form a resist film, exposing a selected region of the resist film to KrF excimer laser, ArF excimer laser, EB or EUV through a photomask, baking, and developing the exposed resist film in a developer.

15. The pattern forming process of claim 14 wherein the developing step uses an alkaline aqueous solution as the developer, thereby forming a positive pattern in which an exposed region of the resist film is dissolved away and an unexposed region of the resist film is not dissolved.

16. The pattern forming process of claim 14 wherein the developing step uses an organic solvent as the developer, thereby forming a negative pattern in which an unexposed region of the resist film is dissolved away and an exposed region of the resist film is not dissolved.

17. The pattern forming process of claim 16 wherein the organic solvent is at least one solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

18. The process of claim 14 wherein the exposure step is carried out by immersion lithography while a liquid having a refractive index of at least 1.0 is held between the resist film and a projection lens.

19. The process of claim 18, further comprising the step of coating a protective film on the resist film prior to the exposure step, wherein immersion lithography is carried out while the liquid is held between the protective film and the projection lens.

* * * * *